United States Patent [19]
Grieve et al.

[11] Patent Number: 5,804,200
[45] Date of Patent: Sep. 8, 1998

[54] PARASITIC NEMATODE PROTEINS AND VACCINES

[75] Inventors: Robert B. Grieve, La Porte; Glenn R. Frank, Fort Collins, both of Colo.

[73] Assignees: Colorado State University Research Foundation; Heska Corporation, both of Ft. Collins, Colo.

[21] Appl. No.: 408,120

[22] Filed: Mar. 20, 1995

Related U.S. Application Data

[63] Continuation of Ser. No. 3,257, Jan. 12, 1993, abandoned, which is a continuation-in-part of Ser. No. 654,226, Feb. 12, 1991, abandoned.

[51] Int. Cl.$^6$ ................. A61K 39/00; A61K 39/002; C07K 14/00; C07K 14/44
[52] U.S. Cl. ................. 424/265.1; 424/184.1; 424/185.1; 424/94.64; 530/350
[58] Field of Search ............. 424/265.1, 266.1, 424/269.1, 184.1, 191.1; 530/300, 350; 435/172.3

[56] References Cited

U.S. PATENT DOCUMENTS 4,842,999  6/1989  Fuller et al. ................. 435/7

FOREIGN PATENT DOCUMENTS

| 8776729 | 2/1988 | Australia . | |
| 0057599 | 3/1988 | Japan ............. | A61K 39/00 |
| WO 90/03433 | 4/1990 | WIPO . | |

OTHER PUBLICATIONS

Diaz–Sanchez et al., *Immunol.*, 72:297–303, 1991.
Rogers et al., *Inf. Immun.*, 59(4):1442–1447, Apr. 1991.
Abraham, et al., "Passive Transfer of Protective Immunity to Larval *Dirofilaria Immitis* from Dogs to Balb/C Mice", pp. 254–257, 1991, *J. Parasitol.*, vol. 77(2).
Abraham, et al., "Genetic Control of Murine Immune Responses to Larval *Dirofilaria Immitis*", pp. 523–528, 1990, *J. Parasitol.*, vol. 76(4).
Abraham, et al., "*Dirofilaria Immitis*: Molting Process of Third–Stage Larvae", pp. 314–322, 1990, *Exp. Parasitol.*, vol. 70.
Abraham, et al., "Active and Passive Immunization of Mice Against Larval *Dirofilaria Immitis*", pp. 275–282, 1988, *J. Parasitol.*, vol. 74(2).
Amiri, et al., "The Schistosomatium Douthitti Cerarial Elastase is Biochemically and Structurally Distinct from that of *Schistosoma Mansoni*," pp. 113–120, 1988, *Mol. Biochem. Parasitol.*, vol. 28.
Awobuluyi, et al., "Immunureactivity of Cloned *Dirofilaria Immitis* Proteins in Dogs Following Vaccination with Irradiated Infective Larvae," p. 139, 1989, 38th Annual Meeting, *Am. J. Trop. Med. Hyg.*, Abstract #150, Dec.
Bianco, et al., "Developmentally Regulated Expression and Secretion of a Polymorphic Antigen by Onchocerca Infective–Stage Larvae", pp. 203–212, 1990, *Mol. Biochem. Parasitol.*, vol. 39.

Blair, et al., "Immunization of Dogs Against *Dirofilaria Immitis* by Means of Chemically Abbreviated Infections", 1982, *Fifth International Congress of Parasitol.*, Toronto, Canada, Aug.
Boyer, et al., "Differential Antigen Content and Isotype Recognition of *O. Volvulvus* Antigens from Nodules Removed from Guatemalan Children", p. 169, 1990, 39th Annual Meeting, *Am. J. Trop. Med. Hyg.*, Abstract #221, Nov.
Chomczynski, et al., "Single–Step Method of RNA Isolation by Acid Guanidinium Thiocyanate–Phenol–Chloroform Extraction", pp. 156–159, 1987, *Anal. Biochem.*, vol. 162.
Coleman, et al., "Use of Implantable Intraperitoneal Diffusion Chambers to Study *Bordetella Pertussis* Pathogenesis: Growth and Toxin Production in Vivo", pp. 33–39, 1986, *J. Infect. Dis.*, vol. 154(1), Jul.
Culpepper, et al., "Molecular Characterization of a *Dirofilaria Immitis* cDNA Encoding a Highly Immunoreactive Antigen", pp. 51–62, 1992, *Mol. Biochem. Parasitol.*, vol. 54.
Dalton, et al., "Thiol Proteases Released in Vitro by *Fasciola Hepatica*", pp. 161–166, 1989, *Mol. Biochem. Parasitol.*, vol. 35.
Davis, et al., "Purification and Biochemical and Immunologic Characterization of a 25KD Glycoprotein from the Surface of *Dirofilaria Immitis* Fourth Stage Larvae", p. 256, 1988, 37th Annual Meeting, *Am. Soc. Trop. Med. Hyg.*, Abstract #404.
Delves, et al., "Neurosecretory–Like Material in 3rd– and 4th–Stage *Dirofilaria Immitis* Larvae (Nematoda: Filarioidea)", pp. 99–104, 1989, *J. Parasitol.*, vol. 99.
Denham, "Vaccination Against Filarial Worms Using Radiation–Attenuated Vaccines", pp. 105–111, 1980, *Inter. J. Nucl. Med. Biol.*, vol. 7.
Frank, et al., "Metabolic Labeling of *Dirofilaria Immitis* Third– and Fourth–Stage Larvae and Their Excretory–Secretory Products", pp. 950–956, 1991, *J. Parasitol.*, vol. 77(6).
Gamble, et al., "Purification of a 44 Kilodalton Protease which Mediates the Ecdysis of Infective *Haemonchus Contortus* Larvae", pp. 49–58 (1989), *Mol. Biochem. Parasitol.*, vol. 33.

(List continued on next page.)

*Primary Examiner*—Hazel F. Sidberry
*Attorney, Agent, or Firm*—Sheridan Ross P.C.

[57] ABSTRACT

Immunogens derived from proteins isolatable from the L3 and L4 larval stages of nematodes parasitic in mammals, and including a protein of about 20.5 kD, are disclosed. The proteins of the invention are identified using biological materials verified to destroy or impair the parasitic nematode in an in vivo incubator. Cells, serum or fractions thereof obtained from immune natural hosts are validated in a method wherein a recoverable implant of the parasitic nematodes is used to assess the protective effect when these materials are provided passively to the animal incubator.

1 Claim, 36 Drawing Sheets

OTHER PUBLICATIONS

Grieve, et al., "Identification of *Dirofilaria Immitis* Larval Antigens with Immunoprophylactic Potential Using Sera from Immune Dogs", pp. 2511–2515, 1992, *J. Immunol.*, vol. 148(8), Apr.

Grieve, "Potential for Immunoprophylaxis Against Heartworm (*Dirofilaria Immitis*) Infection", pp. 187–190, 1989, *Proc. Heartworm Symp.*

Grieve, et al., "Induction of Protective Immunity in Dogs to Infection with *Dirofilaria Immitis* Using Chemically–Abbreviated Infections", pp. 373–379, 1988, *Am. J. Trop. Med. Hyg.*, vol. 39(4).

Grieve, et al., "Epidemiology of Canine Heartworm Infection", pp. 220–246, 1983, *Epidem. Rev.*, vol. 5.

Hewick, et al., "A Gas–Liquid Solid Phase Peptide and Protein Sequenator", pp. 7990–7997, 1981, *J. Biol. Chem.*, vol. 256(15).

Hotez, et al., "Isolation and Characterization of a Proteolytic Enzyme from the Adult Hookworm *Ancylostoma Caninum*", pp. 7343–7348, 1985, *J. Biol. Chem.*, vol. 260(12).

Ibrahim, et al., "Antigen Shedding from the Surface of the Infective Stage Larvae of *Dirofilaria Immitis*", pp. 89–97, 1989, *J. Parasitol.*, vol. 99.

Jwo, et al., "Fractionated Sera from *Schistosoma Mansoni* Infected Patients Confers Passive Protection in Mice", pp. 553–562, 1989, *Am. J. Trop. Med. Hyg.*, vol. 41(5).

Kassis, et al., "Antibody–Dependent Complement–Mediated Killing of Schistosomula in Intraperitoneal Diffusion Chambers in Mice", pp. 1659–5662, 1979, *J. Immunol.*, vol. 123(4), Oct.

Lackey, et al., "Extracellular Proteases Of Onchocerca", pp. 176–185, 1989, *Exp. Parasitol.*, vol. 68.

Lal, et al, "Characterization of Stage–Specific Antigens of Infective of the Filarial Parasite *Brugia Malayi*", pp. 2032–2038, 1988, *J. Immunol.*, vol. 140.

Maki, et al., "Demonstration of Carboxyl and Thiol Protease Activities in Adult *Schistosoma Mansoni, Dirofilaria Immitis, Angiostrongylus Cantonensis* and *Ascaris Suum*", pp. 31–37, 1986, *J. Helminthol.*, vol. 60.

McKerrow, et al., "Proteinases From Invasive Larvae Of The Trematode Parasite *Schistosoma Mansoni* Degrade Connective–Tissue And Basement–Membrane Macromolecules", pp. 47–51, 1985, *Biochem J.*, vol. 231.

McKerrow, et al., "*Schistosoma Mansoni*: Cercarial Degradation of a Radioactively Labeled Collagen Gel", pp. 249–254, 1982, *Exp. Parasitol.*, vol. 53.

McReynolds, et al., "A Large Cuticular Protein from *D. Immitis* that is Also an Excretory or Secretory Product," pp. 173–174, 1989, 38th Annual Meeting, *Am. J. Trop. Med. Hyg.*, Abstract #233, Dec.

McReynolds, et al., "Cloning of a Highly Repeated Protein Located in the Gut of Filarial Parasites," p. 295, 1989, 38th Annual Meeting, *Am. J. Trop. Med. Hyg.*, Abstract #445, Dec.

Mok, et al., "Solubilization of Epicuticular Antigen from *Dirofilaria Immitis* Third–Stage Larvae", pp. 173–182, 1988, *Mol. Biochem. Parasitol.*, vol. 31.

Noble, et al., "*Phylum Nematoda*", pp. 256–322, 1982 (See p. 256), *Parasitol.: The Biology of Animal Parasites*, Section V.

Parab, et al., "Characterization of a Monoclonal Antibody Against Infective Larvae of *Brugia Malayi*", pp. 169–174, 1988, *J. Immunol.*, vol. 64.

Petralanda, et al., "Studies of a Filarial Antigen With Collagenase Activity", pp. 51–59, 1986, *Mol. Biochem. Parasitol.*, vol. 19.

Philipp, et al., "Biochemical and Immunologic Characterization of a Major Surface Antigen of *Dirofilaria Immitis* Infective Larvae", pp. 2621–2627, 1986, *J. Immunol.*, vol. 136(7), Apr.

Richer, et al., "*Dirofilaria Immitis*: Proteases Produced By Third– And Fourth–Stage Larvae", pp. 213–222, 1992, *Exp. Parasitol.*, vol. 75.

Robertson, et al., "*Toxocara Canis*: Proteolytic Enzymes Secreted by the Infective Larvae in Vitro", pp. 30–36, 1989, *Exp. Parasitol.*, vol. 69.

Rogers, "Enzymes in the Exsheathing Fluid of Nematodes and Their Biological Significance," pp. 495–502, 1982, *J. Parasitol.*, vol. 12(6).

Scott, et al., "Surface–Associated Antigens of Second, Third and Fourth Stage Larvae of *Dirofilaria Immitis*", pp. 339–353, 1990, *Acta Tropica*, vol. 47.

Sher, et al., "Passive Transfer of Acquired Resistance to *Schistosoma Mansoni* in Laboratory Mice", pp. 347–357, 1975, *J. Parasitol.*, vol. 70.

Sim, et al., "Immune Response in Human *Brugia Malayi* Infections: Serum Dependent Cell–Mediated Destruction of Infective Larvae in Vitro", pp. 362–370, 1982, *Trans. Roy. Soc. Trop. Med. Hyg.*, vol. 76(3).

Strosberg, et al., "Receptor–Based Assays", pp. 30–36, 1991, *Current Opin. in Biotech.*, vol. 2.

Tamashiro, et al., "Proteolytic Cleavage Of IgG and Other Protein Substrates By *Dirofilaria Immitis* Microfilarial Enzymes", pp. 149–154, 1987, *J. Parasitol.*, vol. 73.

Tanner, et al., "*Dipetalonema Viteae* (Filarioidea): Development of the Infective Larvae in Micropore Chambers Implanted Into Normal, Infected and Immunized Jirds", pp. 173–174, 1981, *Trans. Roy. Soc. Trop. Med. Hyg.*, vol. 75(1).

Wang, et al., "Parenteral Formulations of Proteins and Peptides: Stability and Stabilizers", pp. S3–S26, 1988, *J. Parent. Sci. Tech.*, vol. 42.

Willadsen, et al., "Immunologic Control of a Parasitic Arthropod, Identification of a Protective Antigen from *Boophilus Microplus*", pp. 1346–1351, 1989, *J. Immunol.*, vol. 143, Aug.

Wolff, et al., "Direct Gene Transfer Into Mouse Muscle In Vivo", pp. 1465–1468, 1990, *Science*, vol. 247, Mar.

Wong, et al., "*Dirofilaria Immitis*: Fate and Immunogenicity of Irradiated Infective Stage Larvae in Beagles", pp. 465–474, 1974, *Exp. Parasitol.*, vol. 35.

Young, et al., "Efficient Isolation of Genes by Using Antibody Probes", pp. 1194–1198. 1983, *Proc. Natl. Acad. Sci. USA*, vol. 80, Mar.

Grieve, R.B., et al., "Induction of Protective Immunity in Dogs to Infection with *Dirofilaria Immitis* Using Chemically–Abbreviated Infections", *Am J Trop Med Hyg* (1988) 39(4):373–379.

Abraham, D., et al., "Active and Passive Immunization of Mice Against Larval *Dirofilaria Immitis*", *J Parasit* (1988) 74(2):275–282.

Grieve, R.B., et al., "Epidemiology of Canine Heartworm Infection", *Epidemiologic Reviews* (1983) 5:220–246.

Wong, M.M., et al., "*Dirofilaria immitis*: Fate and Immunogenicity of Irradiated Infective Stage Larvae in Beagles", *Exp Parasitol* (1974) 35:465–474.

Blair, L.S., et al., in *Fifth International Congress of Parasitology*, Toronto, Canada (Aug. 1982).

Grieve, R.B., "Potential for Immunoprophylaxis Against Heartworm (*Dirofilaria Immitis*) Infection", *Proc Heartworm Symp* (1989), pp. 187–190.

Philipp, M., et al., "Biochemical and Immunologic Characterization of a Major Surface Antigen of *Dirofilaria Immitis* Infective Larvae", *J Immunol* (1986) 136(7):2621–2627.

Davis, T.B., et al., Abstract 404, 37th Annual Meeting, Am. Soc. Trop. Med. Hyg. (1988).

Ibrahim, M.S., et al., "Antigen shedding from the surface of the infective stage larvae of *Dirofilaria immitis*", *Parasitol* (1989) 99:89–97.

Scott, A.L., et al., "Surface-associated antigens of second, third and fourth stage larvae of *Dirofilaria immitis*", *Acta Tropica* (1990) 47:339–353.

Tanner, M., et al., "*Dipetalonema viteae* (Filarioidea): development of the infective larvae in micropore chambers implanted into normal, infected and immunized jirds", *Trans Roy Soc Trop Med Hyg* (1981) 75(1):173–174.

Sim, B.K.L. et al., "Immune response in human *Brugia malayi* infections: serum dependent cell-mediated destruction of infective larvae in vitro", *Trans Roy Soc Trop Med Hyg* (1982) 76(3):362–370.

Parab, P.B., et al., "Characterization of a monoclonal antibody against infective larvae of *Brugia malayi*", *Immunol* (1988) 64:169–174.

Sher, A. et al., "Passive transfer of acquired resistance to *Schistosoma mansoni* in laboratory mice", *Parasitol* (1975) 70:347–357.

Jwo, J. et al., "Fractionated Sera From *Schistosoma Mansoni* infected Patients Confers Passive Protection in Mice", *Am J Trop Med Hyg* (1989) 41(5):553–562.

Delves, C.J. et al., "Neurosecretory-like material in 3rd- and 4th-stage *Dirofilaria immitis* larvae (Nematoda: Filarioidea)", *Parasitology* (1989) 99:99–104.

Kassis, A.I. et al., "Antibody-Dependent Complement-Mediated Killing of Schistosomula in Intraperitoneal Diffusion Chambers in Mice", *J. Immunol* (1979) 123(4):1659–1662.

Coleman, A.D. et al., "Use of Implantable Intraperitoneal Diffusion Chambers to Study *Bordetella pertussis* Pathogenesis: Growth and Toxin Production in Vivo", *J Infect Dis* (1986) 154(1):33–39.

Grieve et al Pharmaceutical Biotechnology 6: 737–68 1995 Abstract.

Frank et al J. Parasitol 77: 950–956, 1991.

Houghten et al Vaccines 86 pp. 21–25.

Lal et al The Journal of Immunology 140: 2032–2038, 1987.

Bianco et al Molecule et Biochem Parasitol 39: 203–212, 1988.

Frank Dissertation, Relevant Pages Attached & Abstract.

Lal et al The Jour of Imm 140: 2032–2038 1987.

Boyer et al The 39th Annual Meeting of the American Society of Tropical Medicine & Hygiene, p. 169, Abstractony #221.

Noble et al. Parasitology, The Biology of Animal Parasites 1982 pp. 256–322 See p. 256.

Frank et al, J. Parasitol. 77: 950–6, 1991.

Bianco et al, Molecul. & Biochem. Parasitol 39: 203–212 1988.

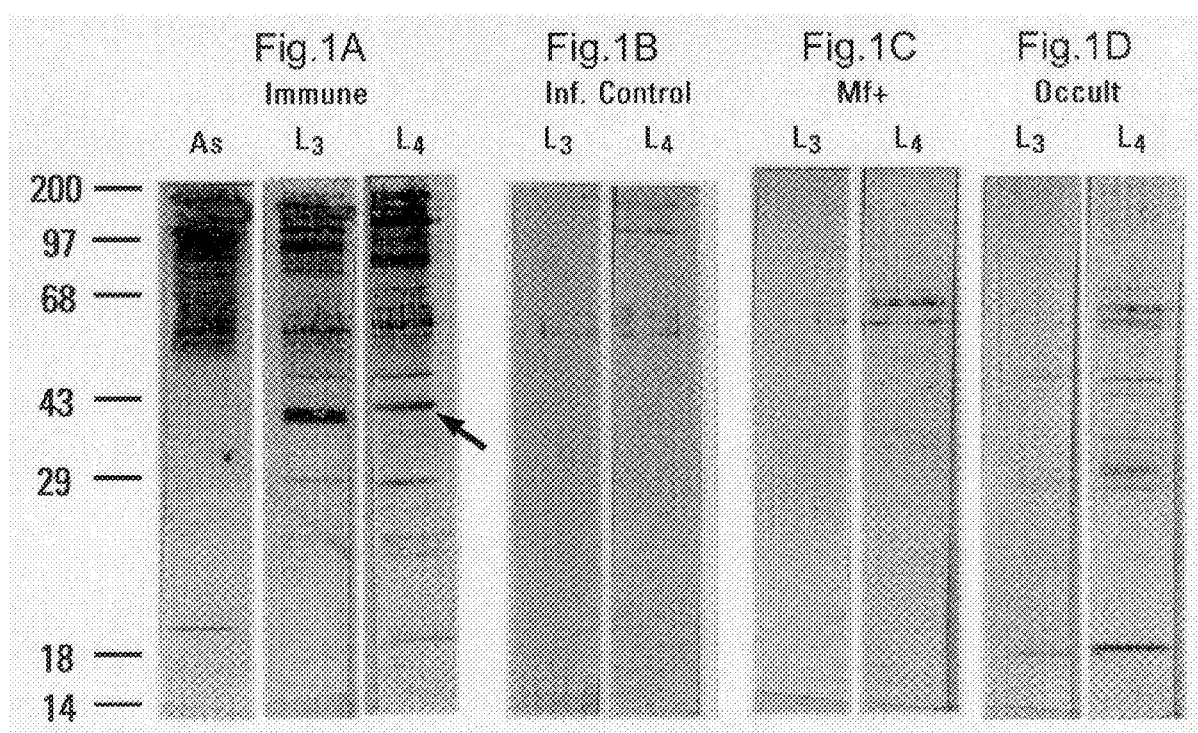

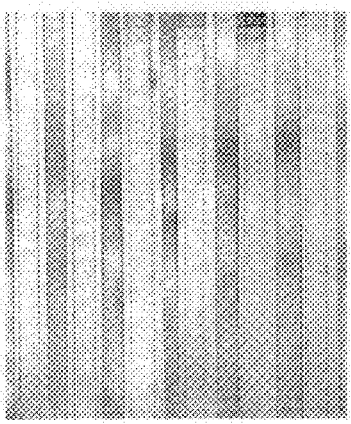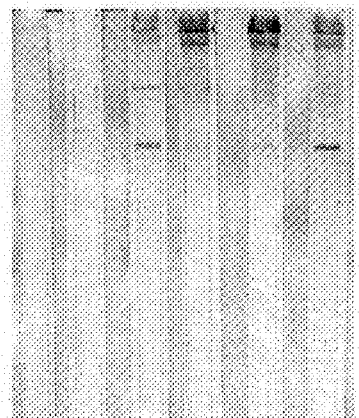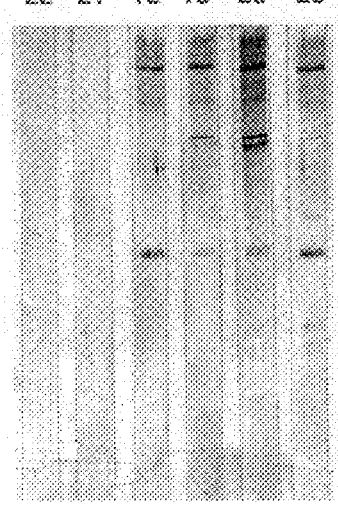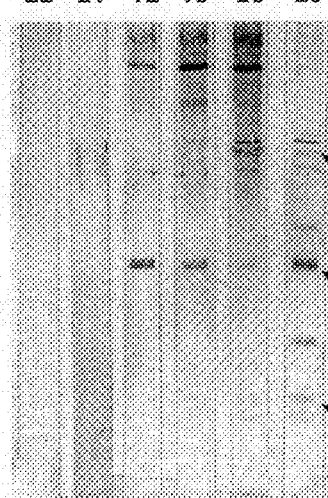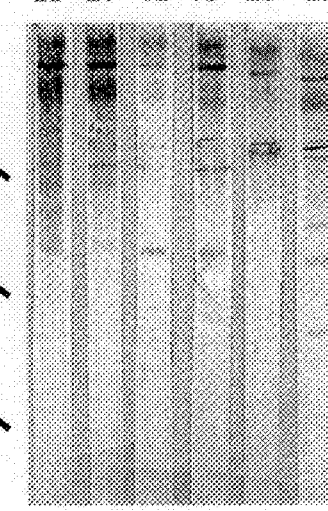

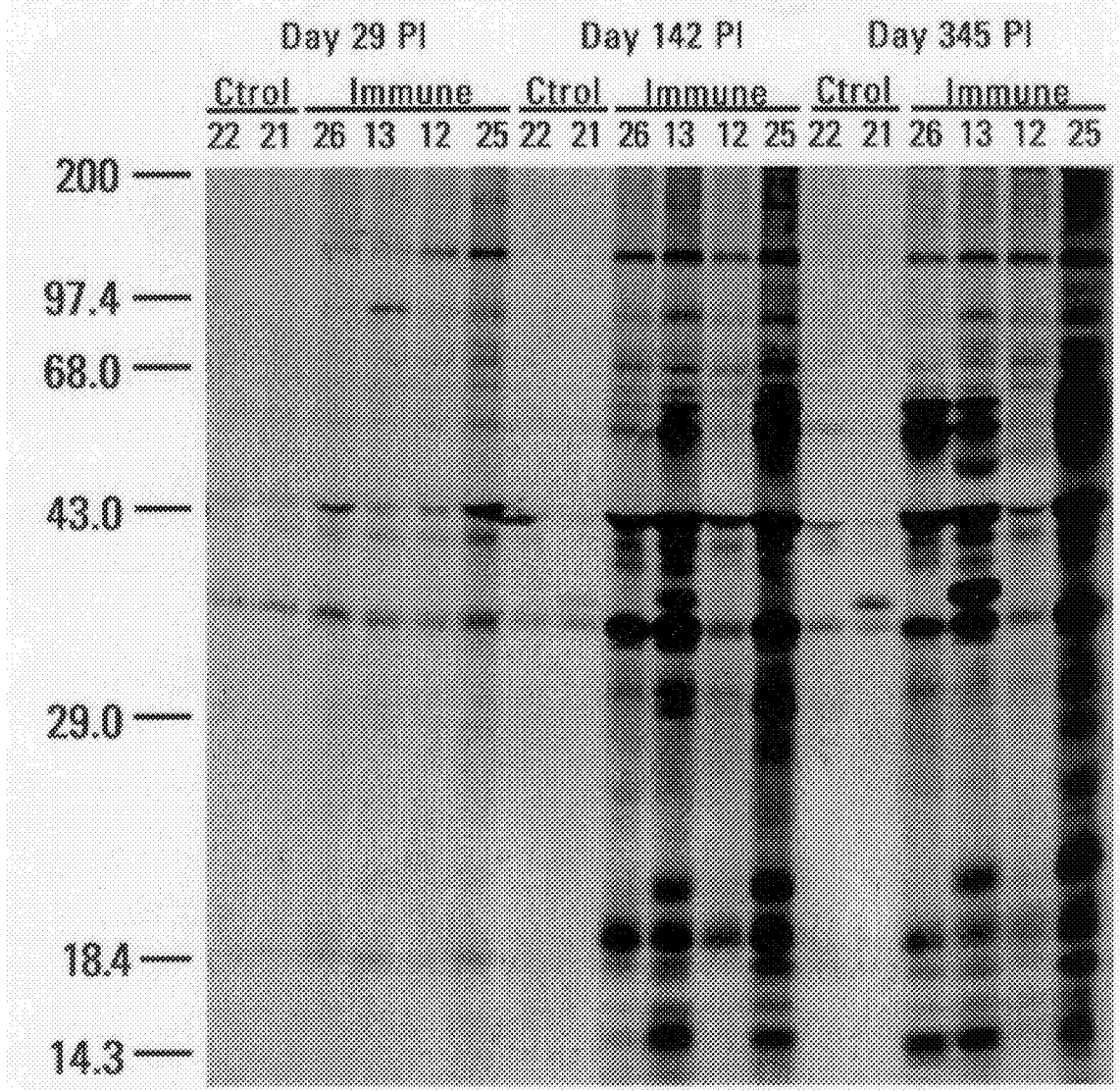

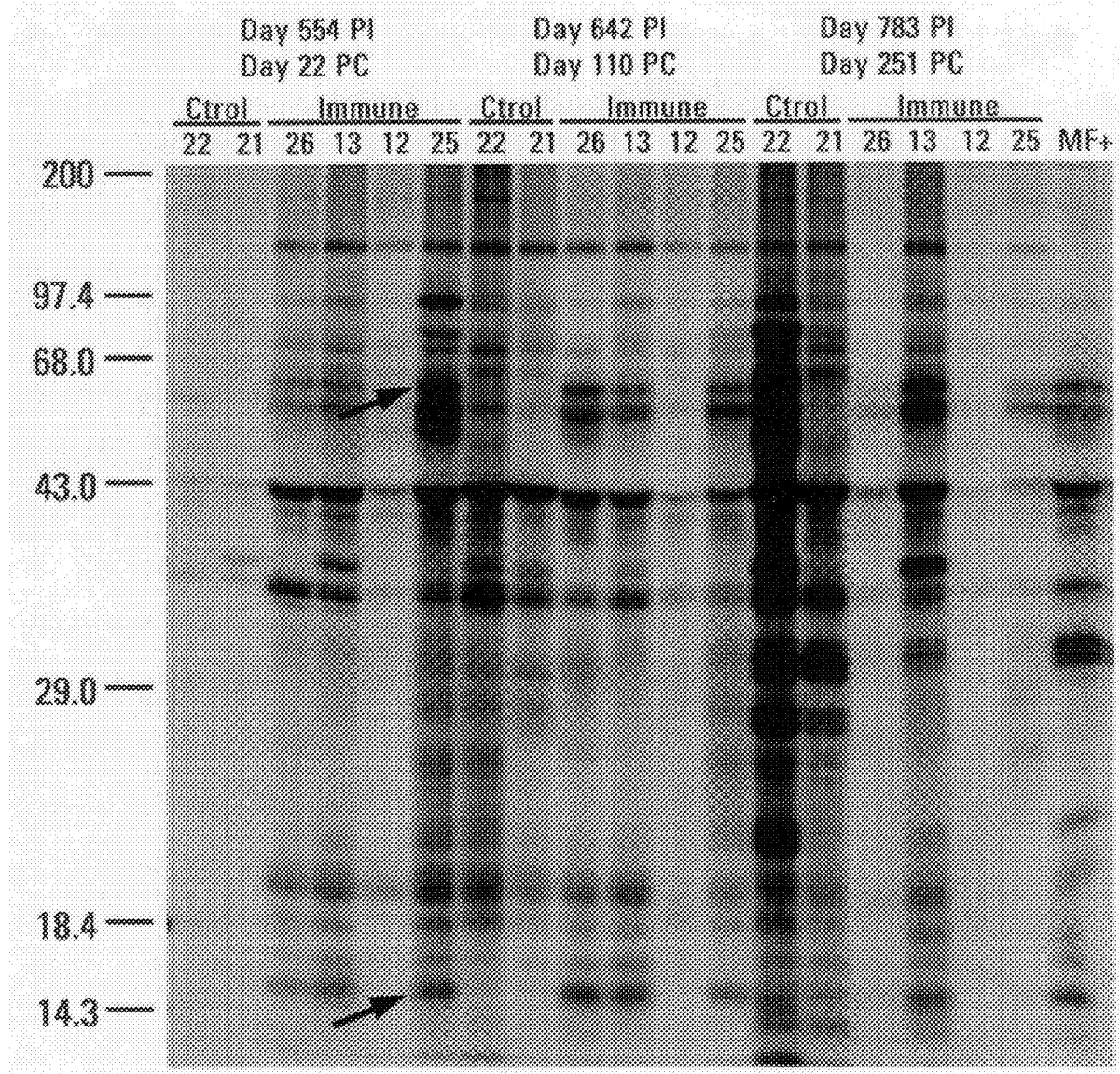

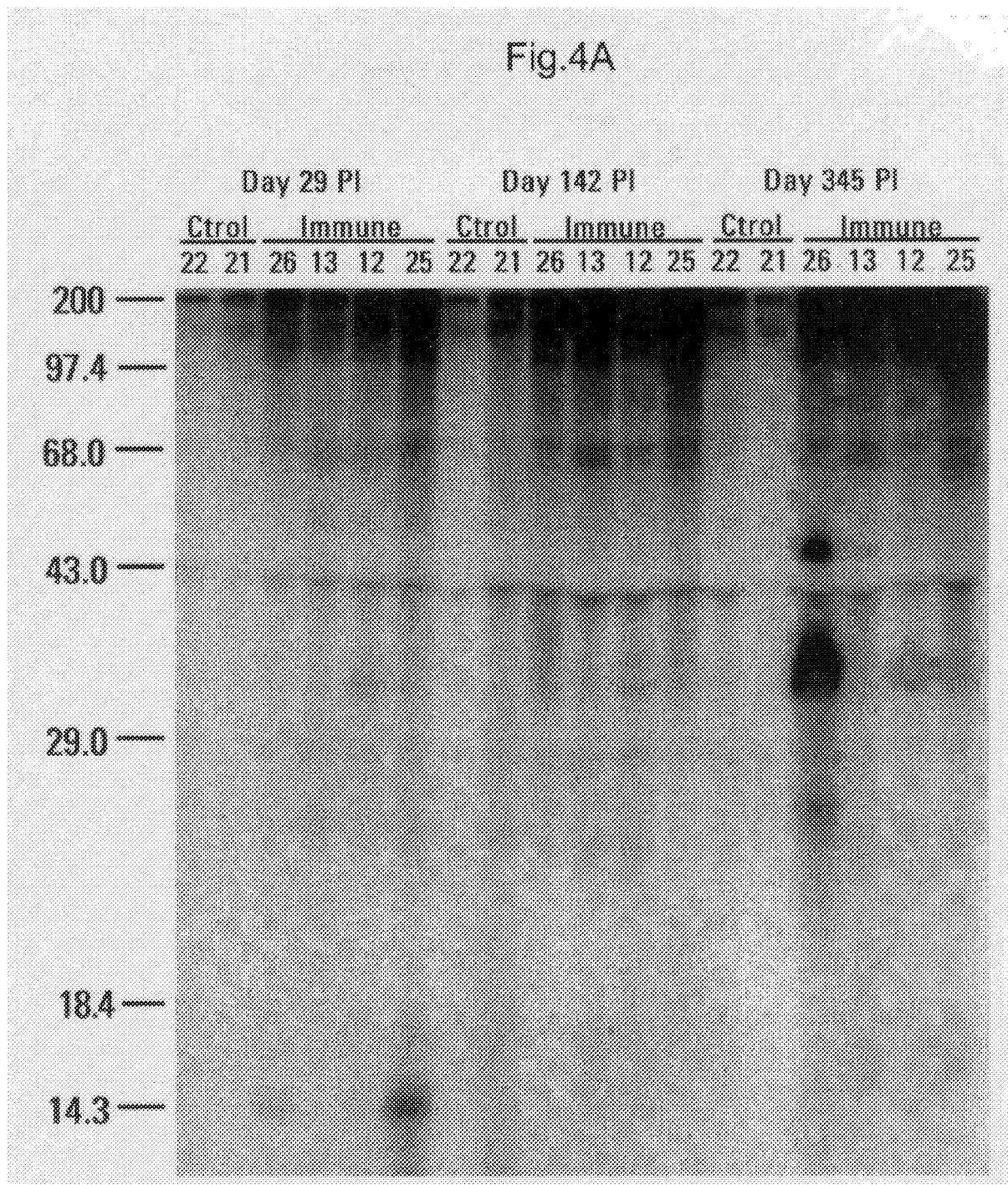

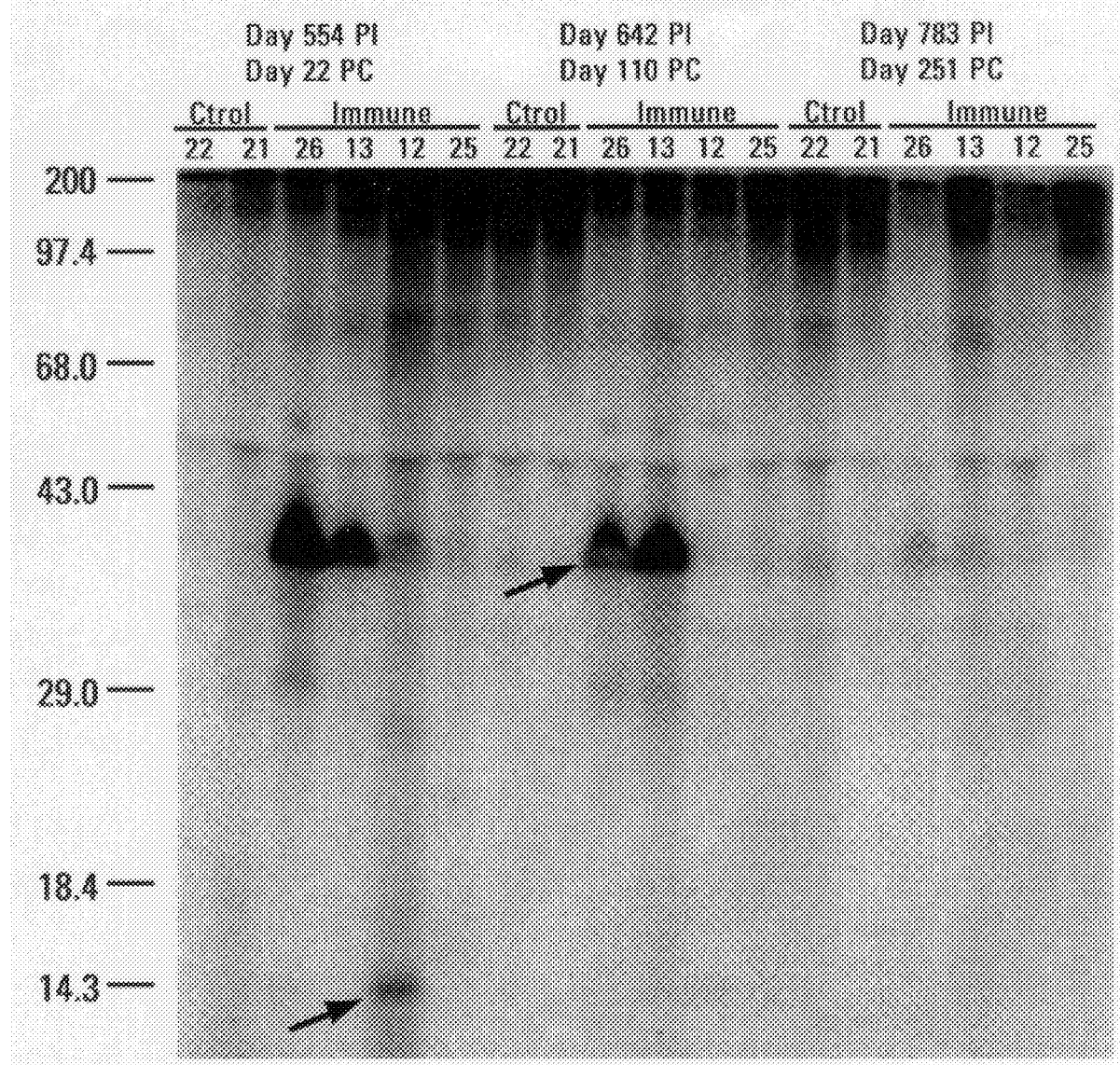

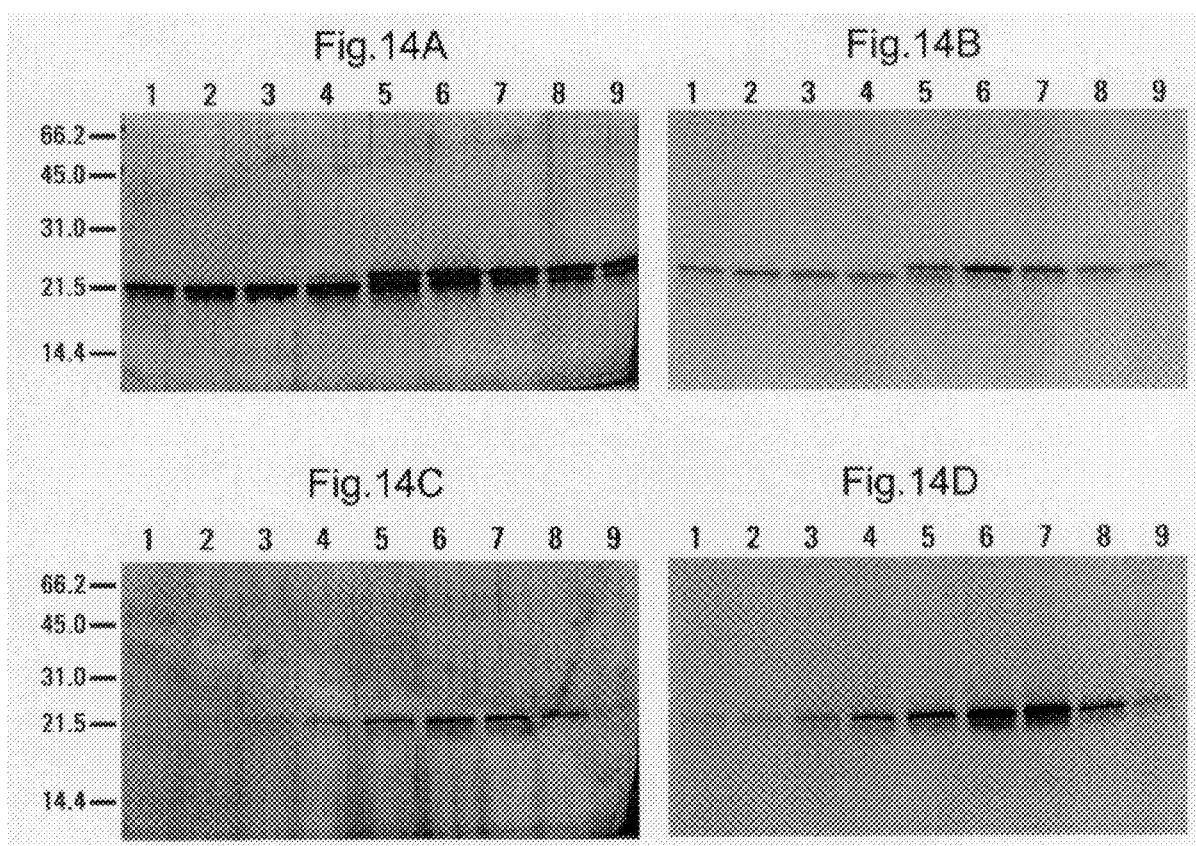

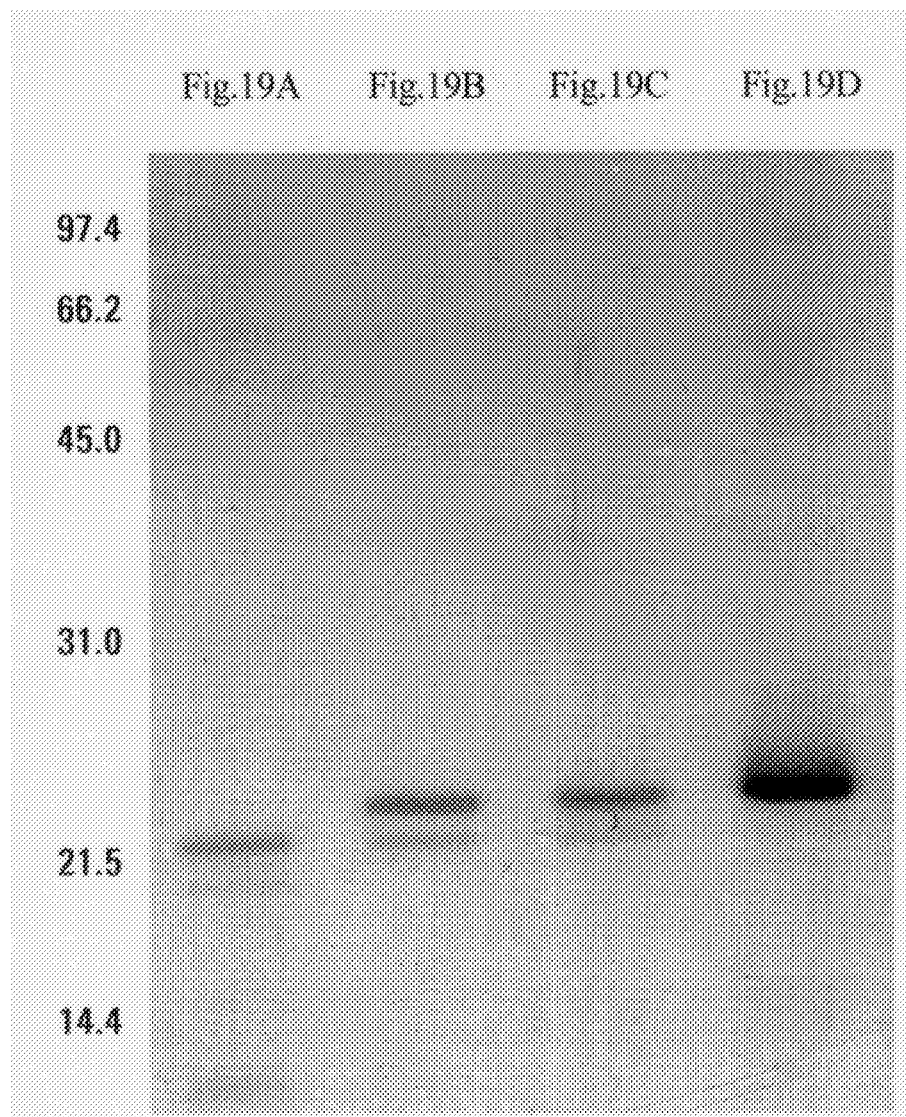

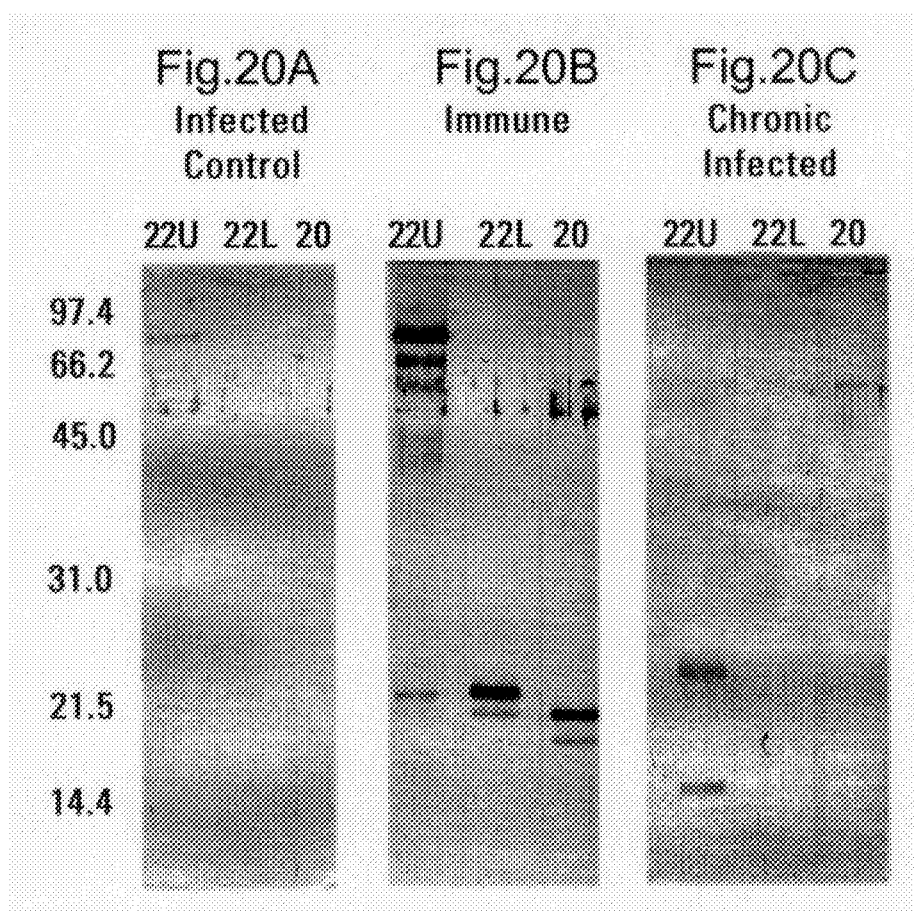

Fig. 21

| Protein | Phase | Source | Sequence |
|---------|-------|--------|----------|
| 20 kD | HPLC | N-term | ETQEETV-FEE-D-D<br>                    P |
| 20 kD | PVDF | N-term | E-QEETV-FEE |
| 20 kD | HPLC | 31 min | FVESDGK |
| 20 kD | HPLC | 32 min | T-EACYDQR |
| 20 kD | HPLC | 42 min | FNWQCSYD<br>ML |
| 22L kD | PVDF | N-term | no sequence |
| 22L kD | HPLC | 35 min | HVETHEACYDQR<br>M GSIG M |
| 22L kD | HPLC | 38 min | GEFVESDGK |
| 22L kD | HPLC | 44 min | N-WQCSYD |
| 22L kD | HPLC | 58 min | EPQSWCILKPHQS-TQR<br>    A          WD |
| 22U kD | HPLC | N-term | no sequence |
| 22U kD | HPLC | N-term | no sequence |
| 22U kD | HPLC | 44 min | MAQDAFPNACAQGEPK<br>        PGERK G |
| 22U kD | HPLC | 58 min | --AIAPCQLTAVQSVLPCADQCQK |
| 22U kD | HPLC | 60 min | -GSCSPDCGLDLPSDNVMVQQV<br>  M  D      WW  W  WS  S |
| 22U kD | HPLC | 60 min | LGSCSPDCGLDLPSDNVMVQDV<br>      V R    R     W |

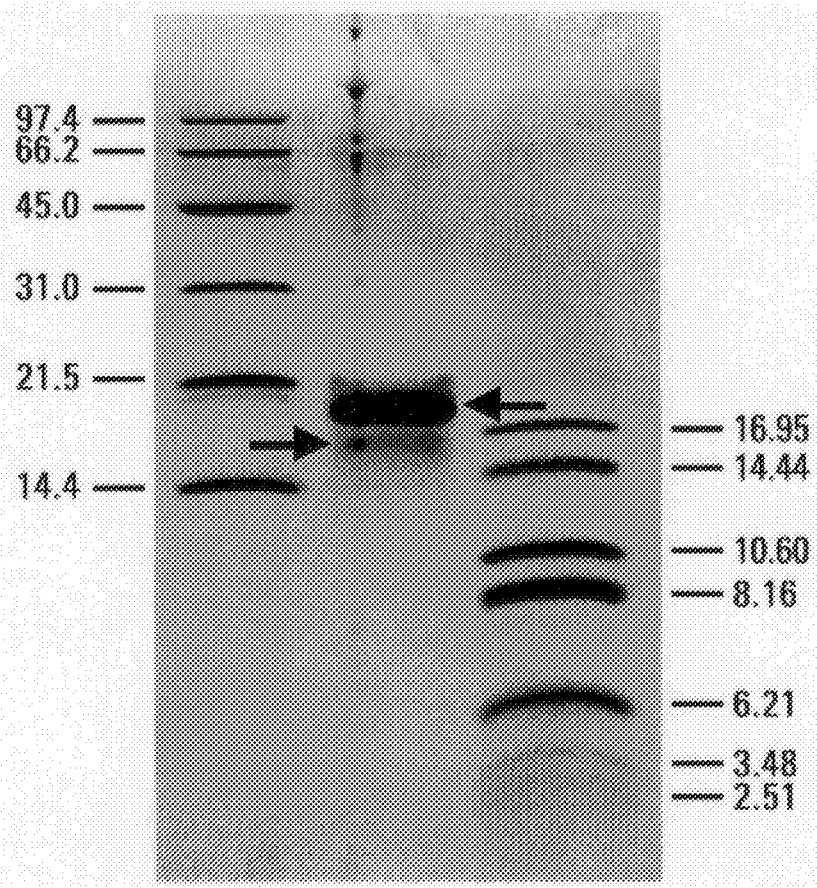

```
  E   K   M   N   K   L   F   I   V   L   G   L   A   L
  gaa aaa atg aac aaa ctt ttc ata gtt ctt ggc tta gcg ctt   42
                                <GRF10
  L   F   V   A   L   P   S   A   S   E   S   Q   E   E
  ctt ttt gtt gca tta cct tcc gca tca gaa tca caa gaa gag   84

T   V   S   F   E   E   S   D   E   D   Y   E   D   D
  act gta tct ttt gaa gaa agc gac gaa gat tat gaa gac gat  126

S   E   D   Q   T   K   E   E   E   H   S   K   E   E
  agt gaa gat caa aca aaa gaa gag gaa cat tca aaa gag gaa  168

D   R   S   E   E   H   D   D   H   S   A   E   D   D
  gat cgt tca gaa gaa cac gac gat cat tca gct gaa gac gat  210
      (a)
  K   F   V   T   K   G   K   F   V   E   S   D   G   K
  aaa ttt gta act aaa gga aaa ttt gtt gaa agt gac ggc aag  252

M   K   H   C   K   T   H   E   A   C   Y   D   Q   R
  atg aag cat tgc aaa acc cat gaa gct tgc tat gat caa cgt  294
                                        GRF6>
  E   P   Q   S   W   C   I   L   K   P   H   Q   S   W
  gaa cca caa tcg tgg tgc ata tta aaa ccg cat cag tca tgg  336
          <GRF13
  T   Q   R   G   C   F   C   E   S   K   K   H   A   C
  aca caa aga ggt tgt ttc tgc gaa tca aaa aaa cat gca tgc  378

V   I   E   R   K   S   G   D   K   L   E   Y   S   Y
  gtt atc gaa cga aaa agc ggc gac aaa ttg gaa tat tcg tat  420

C   S   P   R   K   N   W   Q   C   S   Y   D   *   *
  tgc tca ccc cga aaa aac tgg cag tgt tca tac gat taa taa  462

L   I   I   I   Y   S   F   V   I   S   S   Y   L   A
  ctt ata att atc tat tcc ttc gta att tct tct tat tta gct  504

P   F   N   N   Q   H   F   T   M   F   V   M   Y   S
  cct ttt aat aac caa cat ttt aca atg ttt gtt atg tat tct  546

D   F   S   *   I   Q   S   I   A   I   S   K   K
  gat ttt tct taa ata caa tct att gca atc tca aaa aaa a    586
```

CALCULATED MOLECULAR WEIGHT = 17527.684

ESTIMATED pI = 4.581

AMINO ACID COMPOSITION:

|  |  | NO. | PERCENT |
|---|---|---|---|
| NON-POLAR: | Ala | 6 | 4.00 |
|  | Val | 6 | 4.00 |
|  | Leu | 8 | 5.33 |
|  | Ile | 3 | 2.00 |
|  | Pro | 4 | 2.67 |
|  | Met | 2 | 1.33 |
|  | Phe | 6 | 4.00 |
|  | Trp | 3 | 2.00 |
| POLAR: | Gly | 5 | 3.33 |
|  | Ser | 17 | 11.33 |
|  | Thr | 5 | 3.33 |
|  | Cys | 8 | 5.33 |
|  | Tyr | 5 | 3.33 |
|  | Asn | 2 | 1.33 |
|  | Gln | 7 | 4.67 |
| ACIDIC: | Asp | 14 | 9.33 |
|  | Glu | 22 | 14.67 |
| BASIC: | Lys | 15 | 10.00 |
|  | Arg | 5 | 3.33 |
|  | His | 7 | 4.67 |

Fig. 29B 20 kD

CALCULATED MOLECULAR WEIGHT = 15328.100

ESTIMATED pI = 4.520

AMINO ACID COMPOSITION:

|  |  | NO. | PERCENT |
|---|---|---|---|
| NON-POLAR: | Ala | 3 | 2.33 |
|  | Val | 4 | 3.10 |
|  | Leu | 2 | 1.55 |
|  | Ile | 2 | 1.55 |
|  | Pro | 3 | 2.33 |
|  | Met | 1 | 0.78 |
|  | Phe | 4 | 3.10 |
|  | Trp | 3 | 2.33 |
| POLAR: | Gly | 4 | 3.10 |
|  | Ser | 15 | 11.63 |
|  | Thr | 5 | 3.88 |
|  | Cys | 8 | 6.20 |
|  | Tyr | 5 | 3.88 |
|  | Asn | 1 | 0.78 |
|  | Gln | 7 | 5.43 |
| ACIDIC: | Asp | 14 | 10.85 |
|  | Glu | 22 | 17.05 |
| BASIC: | Lys | 14 | 10.85 |
|  | Arg | 5 | 3.88 |
|  | His | 7 | 5.43 |

Fig. 29C

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i x ) FEATURE:

(A) NAME/KEY: Modified-site
(B) LOCATION: 8
(D) OTHER INFORMATION: /note= "This position is - which is a gap."

(ix) FEATURE:
(A) NAME/KEY: Modified-site
(B) LOCATION: 12
(D) OTHER INFORMATION: /note= "This position is - which is a gap."

(ix) FEATURE:
(A) NAME/KEY: Modified-site
(B) LOCATION: 14
(D) OTHER INFORMATION: /note= "This position is - which is a gap."

(xi) SEQUENCE DESCRIPTION: SEQ ID NO:1:

Glu Thr Gln Glu Glu Thr Val Xaa Phe Glu Glu Xaa Asp Xaa Asp
1               5                   10                  15

(2) INFORMATION FOR SEQ ID NO:2:

(i) SEQUENCE CHARACTERISTICS:
(A) LENGTH: 15 amino acids
(B) TYPE: amino acid
(C) STRANDEDNESS: single
(D) TOPOLOGY: linear (ix) FEATURE:
(A) NAME/KEY: Modified-site
(B) LOCATION: 8
(D) OTHER INFORMATION: /note= "This position is - which is a gap."

(ix) FEATURE:
(A) NAME/KEY: Modified-site
(B) LOCATION: 12
(D) OTHER INFORMATION: /note= "This position is - which is a gap."

(ix) FEATURE:
(A) NAME/KEY: Modified-site
(B) LOCATION: 14
(D) OTHER INFORMATION: /note= "This position is - which is a gap."

(xi) SEQUENCE DESCRIPTION: SEQ ID NO:2:

Glu Thr Gln Glu Glu Thr Val Xaa Phe Glu Pro Xaa Asp Xaa Asp
1               5                   10                  15

(2) INFORMATION FOR SEQ ID NO:3:

(i) SEQUENCE CHARACTERISTICS:
(A) LENGTH: 11 amino acids
(B) TYPE: amino acid
(C) STRANDEDNESS: single
(D) TOPOLOGY: linear (ix) FEATURE:
(A) NAME/KEY: Modified-site
(B) LOCATION: 2
(D) OTHER INFORMATION: /note= "This position is - which is a gap."

(ix) FEATURE:
(A) NAME/KEY: Modified-site
(B) LOCATION: 8
(D) OTHER INFORMATION: /note= "This position is - which is a gap."

(xi) SEQUENCE DESCRIPTION: SEQ ID NO:3:

Glu Xaa Gln Glu Glu Thr Val Xaa Phe Glu Glu
1               5                   10

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

Phe   Val   Glu   Ser   Asp   Gly   Lys
    1                            5

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 2
        ( D ) OTHER INFORMATION: /note= "This position is - which is
            a gap."

( x i ) SEQUENCE DESCRIPTION: SEQ ID NO:5:

Thr   Xaa   Glu   Ala   Cys   Tyr   Asp   Gln   Arg
    1                            5

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

Phe   Asn   Trp   Gln   Cys   Ser   Tyr   Asp
    1                            5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

Phe   Met   Leu   Gln   Cys   Ser   Tyr   Asp
    1                            5

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

His   Val   Glu   Thr   His   Glu   Ala   Cys   Tyr   Asp   Gln   Arg
    1                            5                            10

( 2 ) INFORMATION FOR SEQ ID NO:9:

( i ) SEQUENCE CHARACTERISTICS:

(A) LENGTH: 12 amino acids
(B) TYPE: amino acid
(C) STRANDEDNESS: single
(D) TOPOLOGY: linear (xi) SEQUENCE DESCRIPTION: SEQ ID NO:9:

Met Val Gly Ser Ile Gly Ala Met Tyr Asp Gln Arg
1               5                   10

(2) INFORMATION FOR SEQ ID NO:10:

(i) SEQUENCE CHARACTERISTICS:
(A) LENGTH: 9 amino acids
(B) TYPE: amino acid
(C) STRANDEDNESS: single
(D) TOPOLOGY: linear (xi) SEQUENCE DESCRIPTION: SEQ ID NO:10:

Gly Glu Phe Val Glu Ser Asp Gly Lys
1               5

(2) INFORMATION FOR SEQ ID NO:11:

(i) SEQUENCE CHARACTERISTICS:
(A) LENGTH: 8 amino acids
(B) TYPE: amino acid
(C) STRANDEDNESS: single
(D) TOPOLOGY: linear (ix) FEATURE:
(A) NAME/KEY: Modified-site
(B) LOCATION: 2
(D) OTHER INFORMATION: /note= "This position is - which is
     a gap."

(xi) SEQUENCE DESCRIPTION: SEQ ID NO:11:

Asn Xaa Trp Gln Cys Ser Tyr Asp
1               5

(2) INFORMATION FOR SEQ ID NO:12:

(i) SEQUENCE CHARACTERISTICS:
(A) LENGTH: 17 amino acids
(B) TYPE: amino acid
(C) STRANDEDNESS: single
(D) TOPOLOGY: linear (ix) FEATURE:
(A) NAME/KEY: Modified-site
(B) LOCATION: 14
(D) OTHER INFORMATION: /note= "This position is - which is
     a gap."

(xi) SEQUENCE DESCRIPTION: SEQ ID NO:12:

Glu Pro Gln Ser Trp Cys Ile Leu Lys Pro His Gln Ser Xaa Thr Gln
1               5                   10                  15
Arg (2) INFORMATION FOR SEQ ID NO:13:

(i) SEQUENCE CHARACTERISTICS:
(A) LENGTH: 17 amino acids
(B) TYPE: amino acid
(C) STRANDEDNESS: single
(D) TOPOLOGY: linear (ix) FEATURE:
(A) NAME/KEY: Modified-site
(B) LOCATION: 14
(D) OTHER INFORMATION: /note= "This position is - which is
     a gap."

( x i ) SEQUENCE DESCRIPTION: SEQ ID NO:13:

Glu Pro Gln Ser Ala Cys Ile Leu Lys Pro His Gln Ser Xaa Trp Asp
1               5                   10                  15

Arg ( 2 ) INFORMATION FOR SEQ ID NO:14:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( x i ) SEQUENCE DESCRIPTION: SEQ ID NO:14:

Met Ala Gln Asp Ala Phe Pro Asn Ala Cys Ala Gln Gly Glu Pro Lys
1               5                   10                  15

( 2 ) INFORMATION FOR SEQ ID NO:15:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( x i ) SEQUENCE DESCRIPTION: SEQ ID NO:15:

Met Ala Gln Pro Gly Glu Arg Lys Ala Gly Ala Gln Gly Glu Pro Lys
1               5                   10                  15

( 2 ) INFORMATION FOR SEQ ID NO:16:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( x i ) SEQUENCE DESCRIPTION: SEQ ID NO:16:

Ala Ile Ala Pro Cys Gln Leu Thr Ala Val Gln Ser Val Leu Pro Cys
1               5                   10                  15

Ala Asp Gln Cys Gln Lys
            20

( 2 ) INFORMATION FOR SEQ ID NO:17:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( x i ) SEQUENCE DESCRIPTION: SEQ ID NO:17:

Gly Ser Cys Ser Pro Asp Cys Gly Leu Asp Leu Pro Ser Asp Asn Val
1               5                   10                  15

Met Val Gln Gln Val
            20

( 2 ) INFORMATION FOR SEQ ID NO:18:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( x i ) SEQUENCE DESCRIPTION: SEQ ID NO:18:

```
            Met  Ser  Cys  Asp  Pro  Asp  Cys  Gly  Leu  Trp  Trp  Pro  Ser  Trp  Asn  Val
            1              5                        10                       15

Trp  Ser  Gln  Gln  Ser
                           20
```

( 2 ) INFORMATION FOR SEQ ID NO:19:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( x i ) SEQUENCE DESCRIPTION: SEQ ID NO:19:

```
            Leu  Gly  Ser  Cys  Ser  Pro  Asp  Cys  Gly  Leu  Asp  Leu  Pro  Ser  Asp  Asn
            1              5                        10                       15

Val  Met  Val  Gln  Asp  Val
                           20
```

( 2 ) INFORMATION FOR SEQ ID NO:20:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( x i ) SEQUENCE DESCRIPTION: SEQ ID NO:20:

```
            Leu  Gly  Ser  Val  Ser  Arg  Asp  Cys  Gly  Leu  Asp  Leu  Arg  Ser  Asp  Asn
            1              5                        10                       15

Val  Met  Val  Gln  Trp  Val
                           20
```

( 2 ) INFORMATION FOR SEQ ID NO:21:

( i ) SEQUENCE CHARACTERISTICS:
        ( A ) LENGTH: 586 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: join(1..456, 463..555, 559..585)

( x i ) SEQUENCE DESCRIPTION: SEQ ID NO:21:

```
GAA  AAA  ATG  AAC  AAA  CTT  TTC  ATA  GTT  CTT  GGC  TTA  GCG  CTT  CTT  TTT         48
Glu  Lys  Met  Asn  Lys  Leu  Phe  Ile  Val  Leu  Gly  Leu  Ala  Leu  Leu  Phe
1                   5                        10                       15

GTT  GCA  TTA  CCT  TCC  GCA  TCA  GAA  TCA  CAA  GAA  GAG  ACT  GTA  TCT  TTT         96
Val  Ala  Leu  Pro  Ser  Ala  Ser  Glu  Ser  Gln  Glu  Glu  Thr  Val  Ser  Phe
                    20                       25                       30

GAA  GAA  AGC  GAC  GAA  GAT  TAT  GAA  GAC  GAT  AGT  GAA  GAT  CAA  ACA  AAA        144
Glu  Glu  Ser  Asp  Glu  Asp  Tyr  Glu  Asp  Asp  Ser  Glu  Asp  Gln  Thr  Lys
               35                       40                       45

GAA  GAG  GAA  CAT  TCA  AAA  GAG  GAA  GAT  CGT  TCA  GAA  GAA  CAC  GAC  GAT        192
Glu  Glu  Glu  His  Ser  Lys  Glu  Glu  Asp  Arg  Ser  Glu  Glu  His  Asp  Asp
          50                       55                       60

CAT  TCA  GCT  GAA  GAC  GAT  AAA  TTT  GTA  ACT  AAA  GGA  AAA  TTT  GTT  GAA        240
His  Ser  Ala  Glu  Asp  Asp  Lys  Phe  Val  Thr  Lys  Gly  Lys  Phe  Val  Glu
65                       70                       75                       80

AGT  GAC  GGC  AAG  ATG  AAG  CAT  TGC  AAA  ACC  CAT  GAA  GCT  TGC  TAT  GAT        288
Ser  Asp  Gly  Lys  Met  Lys  His  Cys  Lys  Thr  His  Glu  Ala  Cys  Tyr  Asp
                    85                       90                       95
```

```
CAA  CGT  GAA  CCA  CAA  TCG  TGG  TGC  ATA  TTA  AAA  CCG  CAT  CAG  TCA  TGG        336
Gln  Arg  Glu  Pro  Gln  Ser  Trp  Cys  Ile  Leu  Lys  Pro  His  Gln  Ser  Trp
          100                      105                      110

ACA  CAA  AGA  GGT  TGT  TTC  TGC  GAA  TCA  AAA  AAA  CAT  GCA  TGC  GTT  ATC        384
Thr  Gln  Arg  Gly  Cys  Phe  Cys  Glu  Ser  Lys  Lys  His  Ala  Cys  Val  Ile
          115                      120                      125

GAA  CGA  AAA  AGC  GGC  GAC  AAA  TTG  GAA  TAT  TCG  TAT  TGC  TCA  CCC  CGA        432
Glu  Arg  Lys  Ser  Gly  Asp  Lys  Leu  Glu  Tyr  Ser  Tyr  Cys  Ser  Pro  Arg
          130                      135                      140

AAA  AAC  TGG  CAG  TGT  TCA  TAC  GAT  TAATAA  CTT  ATA  ATT  ATC  TAT  TCC          480
Lys  Asn  Trp  Gln  Cys  Ser  Tyr  Asp          Leu  Ile  Ile  Ile  Tyr  Ser
145                 150                                   155

TTC  GTA  ATT  TCT  TCT  TAT  TTA  GCT  CCT  TTT  AAT  AAC  CAA  CAT  TTT  ACA        528
Phe  Val  Ile  Ser  Ser  Tyr  Leu  Ala  Pro  Phe  Asn  Asn  Gln  His  Phe  Thr
     160                      165                      170

ATG  TTT  GTT  ATG  TAT  TCT  GAT  TTT  TCT  TAA  ATA  CAA  TCT  ATT  GCA  ATC        576
Met  Phe  Val  Met  Tyr  Ser  Asp  Phe  Ser       Ile  Gln  Ser  Ile  Ala  Ile
175                      180                           185

TCA  AAA  AAA  A                                                                      586
Ser  Lys  Lys
190
```

(2) INFORMATION FOR SEQ ID NO:22:

(i) SEQUENCE CHARACTERISTICS:
        (A) LENGTH: 192 amino acids
        (B) TYPE: amino acid
        (D) TOPOLOGY: linear (ii) MOLECULE TYPE: protein (xi) SEQUENCE DESCRIPTION: SEQ ID NO:22:

```
Glu  Lys  Met  Asn  Lys  Leu  Phe  Ile  Val  Leu  Gly  Leu  Ala  Leu  Leu  Phe
 1              5                        10                      15

Val  Ala  Leu  Pro  Ser  Ala  Ser  Glu  Ser  Gln  Glu  Glu  Thr  Val  Ser  Phe
               20                   25                      30

Glu  Glu  Ser  Asp  Glu  Asp  Tyr  Glu  Asp  Ser  Glu  Asp  Gln  Thr  Lys
          35                   40                   45

Glu  Glu  Glu  His  Ser  Lys  Glu  Glu  Asp  Arg  Ser  Glu  Glu  His  Asp  Asp
     50                   55                        60

His  Ser  Ala  Glu  Asp  Asp  Lys  Phe  Val  Thr  Lys  Gly  Lys  Phe  Val  Glu
65                       70                   75                            80

Ser  Asp  Gly  Lys  Met  Lys  His  Cys  Lys  Thr  His  Glu  Ala  Cys  Tyr  Asp
               85                        90                       95

Gln  Arg  Glu  Pro  Gln  Ser  Trp  Cys  Ile  Leu  Lys  Pro  His  Gln  Ser  Trp
          100                      105                      110

Thr  Gln  Arg  Gly  Cys  Phe  Cys  Glu  Ser  Lys  Lys  His  Ala  Cys  Val  Ile
          115                      120                      125

Glu  Arg  Lys  Ser  Gly  Asp  Lys  Leu  Glu  Tyr  Ser  Tyr  Cys  Ser  Pro  Arg
          130                      135                      140

Lys  Asn  Trp  Gln  Cys  Ser  Tyr  Asp  Leu  Ile  Ile  Ile  Tyr  Ser  Phe  Val
145                 150                      155                            160

Ile  Ser  Ser  Tyr  Leu  Ala  Pro  Phe  Asn  Asn  Gln  His  Phe  Thr  Met  Phe
               165                      170                      175

Val  Met  Tyr  Ser  Asp  Phe  Ser  Ile  Gln  Ser  Ile  Ala  Ile  Ser  Lys  Lys
               180                      185                      190
```

(2) INFORMATION FOR SEQ ID NO:23:

(i) SEQUENCE CHARACTERISTICS:

(A) LENGTH: 150 amino acids
(B) TYPE: amino acid
(C) STRANDEDNESS: single
(D) TOPOLOGY: linear (xi) SEQUENCE DESCRIPTION: SEQ ID NO:23:

Met Asn Lys Leu Phe Ile Val Leu Gly Leu Ala Leu Leu Phe Val Ala
1               5                   10                  15

Leu Pro Ser Ala Ser Glu Ser Gln Glu Glu Thr Val Ser Phe Glu Glu
            20              25                  30

Ser Asp Glu Asp Tyr Glu Asp Ser Glu Asp Gln Thr Lys Glu Glu
            35              40              45

Glu His Ser Lys Glu Glu Asp Arg Ser Glu Glu His Asp Asp His Ser
        50              55                  60

Ala Glu Asp Asp Lys Phe Val Thr Lys Gly Lys Phe Val Glu Ser Asp
65                  70              75                      80

Gly Lys Met Lys His Cys Lys Thr His Glu Ala Cys Tyr Asp Gln Arg
                85                  90                  95

Glu Pro Gln Ser Trp Cys Ile Leu Lys Pro His Gln Ser Trp Thr Gln
            100                 105                 110

Arg Gly Cys Phe Cys Glu Ser Lys Lys His Ala Cys Val Ile Glu Arg
            115             120                 125

Lys Ser Gly Asp Lys Leu Glu Tyr Ser Tyr Cys Ser Pro Arg Lys Asn
        130                 135                 140

Trp Gln Cys Ser Tyr Asp
145             150

(2) INFORMATION FOR SEQ ID NO:24:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:24:

CGCTCTAGAA CTAGTGGATC                                   20

(2) INFORMATION FOR SEQ ID NO:25:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:25:

AATACGACTC ACTATAG                                      17

(2) INFORMATION FOR SEQ ID NO:26:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:26:

TATGCACCAC GATTGTGG                                     18

(2) INFORMATION FOR SEQ ID NO:27:

(i) SEQUENCE CHARACTERISTICS:

(A) LENGTH: 129 amino acids
(B) TYPE: amino acid
(C) STRANDEDNESS: single
(D) TOPOLOGY: linear (xi) SEQUENCE DESCRIPTION: SEQ ID NO:27:

| Glu | Ser | Gln | Glu | Glu | Thr | Val | Ser | Phe | Glu | Glu | Ser | Asp | Glu | Asp | Tyr |
|---|---|---|---|---|---|---|---|---|---|---|---|---|---|---|---|
| 1 | | | | 5 | | | | | 10 | | | | | 15 | |

| Glu | Asp | Asp | Ser | Glu | Asp | Gln | Thr | Lys | Glu | Glu | His | Ser | Lys | Glu |
|---|---|---|---|---|---|---|---|---|---|---|---|---|---|---|
| | | | 20 | | | | | 25 | | | | 30 | | |

Glu Asp Arg Ser Glu Glu His Asp Asp His Ser Ala Glu Asp Asp Lys
                35                    40                  45

Phe Val Thr Lys Gly Lys Phe Val Glu Ser Asp Gly Lys Met Lys His
         50                   55                  60

Cys Lys Thr His Glu Ala Cys Tyr Asp Gln Arg Glu Pro Gln Ser Trp
65                       70                   75                  80

Cys Ile Leu Lys Pro His Gln Ser Trp Thr Gln Arg Gly Cys Phe Cys
                 85                    90                  95

Glu Ser Lys Lys His Ala Cys Val Ile Glu Arg Lys Ser Gly Asp Lys
             100                    105                110

Leu Glu Tyr Ser Tyr Cys Ser Pro Arg Lys Asn Trp Gln Cys Ser Tyr
         115                 120                 125

Asp (2) INFORMATION FOR SEQ ID NO:28:

(i) SEQUENCE CHARACTERISTICS:
(A) LENGTH: 21 amino acids
(B) TYPE: amino acid
(C) STRANDEDNESS: single
(D) TOPOLOGY: linear (xi) SEQUENCE DESCRIPTION: SEQ ID NO:28:

Met Asn Lys Leu Phe Ile Val Leu Gly Leu Ala Leu Leu Phe Val Ala
1                5                   10                  15

Leu Pro Ser Ala Ser
             20

(2) INFORMATION FOR SEQ ID NO:29:

(i) SEQUENCE CHARACTERISTICS:
(A) LENGTH: 390 base pairs
(B) TYPE: nucleic acid
(C) STRANDEDNESS: single
(D) TOPOLOGY: linear (xi) SEQUENCE DESCRIPTION: SEQ ID NO:29:

```
GAATCACAAG  AAGAGACTGT  ATCTTTTGAA  GAAAGCGACG  AAGATTATGA  AGACGATAGT     60
GAAGATCAAA  CAAAAGAAGA  GGAACATTCA  AAAGAGGAAG  ATCGTTCAGA  AGAACACGAC    120
GATCATTCAG  CTGAAGACGA  TAAATTTGTA  ACTAAAGGAA  AATTTGTTGA  AAGTGACGGC    180
AAGATGAAGC  ATTGCAAAAC  CCATGAAGCT  TGCTATGATC  AACGTGAACC  ACAATCGTGG    240
TGCATATTAA  AACCGCATCA  GTCATGGACA  CAAAGAGGTT  GTTTCTGCGA  ATCAAAAAAA    300
CATGCATGCG  TTATCGAACG  AAAAAGCGGC  GACAAATTGG  AATATTCGTA  TTGCTCACCC    360
CGAAAAAACT  GGCAGTGTTC  ATACGATTAA                                       390
```

(2) INFORMATION FOR SEQ ID NO:30:

(i) SEQUENCE CHARACTERISTICS:
(A) LENGTH: 63 base pairs

-continued ( B ) TYPE: nucleic acid
( C ) STRANDEDNESS: single
( D ) TOPOLOGY: linear ( x i ) SEQUENCE DESCRIPTION: SEQ ID NO:30:

ATGAACAAAC TTTTCATAGT TCTTGGCTTA GCGCTTCTTT TTGTTGCATT ACCTTCCGCA 60

TCA 63

PARASITIC NEMATODE PROTEINS AND VACCINES

CROSS REFERENCE TO A RELATED APPLICATION

This is a continuation of application Ser. No. 08/003,257, filed on Jan. 12, 1993, now abandoned, and is a continuation-in-part of U.S. patent application Ser. No. 07/654,226, filed Feb. 12, 1991, now abandoned the disclosure of which is incorporated by reference.

TECHNICAL FIELD

The invention is directed to 20.5 kD and 22 kD protein immunogens that characterize the L3 and L4 larval stages of *D. immitis* and related nematodes, and to the isolation, purification and use thereof. The proteins of the invention are identified using biological materials verified to destroy or impair the infective agent in an in vivo incubator. Cells, serum or fractions thereof obtained from exposed natural hosts are used in a method wherein a recoverable implant of infectious agent is used to assess the protective effect when these materials are provided passively to the animal incubator.

BACKGROUND ART

The general method provided by the invention below to obtain suitable immunogens for use in vaccines is applied specifically to heartworm infection in canines and other mammals, which is caused by the nematode *Dirofilaria immitis*. Accordingly, a preliminary discussion of the nature of this infection and the life cycle of the *D. immitis* parasite may be helpful both in reviewing the background literature and in describing the invention. The adult forms of the parasite are quite large (males are 12–20 cm long and 0.7–0.9 mm wide; females are 25–31 cm long and 1.0–1.3 mm wide) and these preferentially inhabit the heart and pulmonary arteries of the dog. The sexually mature adults, after mating, produce as embryos microfilariae which are only 300 $\mu$m long and 7 $\mu$m wide. These traverse capillary beds and circulate in the vascular system of the dog in concentrations of $10^3$–$10^5$ microfilariae per ml of blood. One way of demonstrating infection in the dog is to detect the circulating microfilariae.

If the dog is maintained in an insect-free environment, the life cycle of the parasite cannot progress. However, when microfilariae are ingested by the female mosquito during blood feeding on an infected dog, subsequent development (but not, of course, increase in numbers) occurs in the mosquito. The microfilariae go through two larval stages (L1 and L2) and finally become mature third stage larvae (L3) of about 1.1 mm length, which can then be transmitted back to the dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as that wherein no microfilaremia is demonstrable, but the existence of the adult heartworms can be determined through thoracic examination.

Control of heartworm infection in canines has largely been chemoprophylactic, and no effective vaccine is available for practical immunization of the dog population against this parasite. Further, there appears no generic method to determine suitable immunogens for use as active ingredients in vaccines directed against infectious diseases caused by parasites in general. The invention provides solutions to both of these problems.

As to the general approach to a method to obtain vaccine components, the ability of various components of infectious agents to raise antibodies when injected into animal hosts is well understood not to be determinative of the ability of these components to behave as effective vaccines. A large number of materials are immunogenic and produce sera which test positive in immunoassays for ability to react with the immunizing antigen, but which fail to protect the hosts against infection. Antibodies which neutralize the infective agent in in vitro assays are much more likely to protect against challenge in vivo. Accordingly, the use of "immune" serum simply resulting from "immunization" or from infection by the infectious agent to screen for candidate vaccines does not provide sufficient specificity to identify protective immunogens. On the other hand, serum or other components of blood from immunized animals which is demonstrably protective against infection is assured to contain antibodies, cells, or other factors reactive with an immunogen or infectious agent which will produce responses that protect against challenge.

In most infectious diseases, particularly those such as parasitic infections that have long and complex development courses, it is difficult to verify the protective effect of serum or T-cells from exposed animals for use as a screening reagent. First, verification of protection against challenge is tedious, since the host animal would first have to be challenged with the infectious agent and shown to be protected before it could be shown that antibody components of serum, for example, could be used as a screen. The definition of "protection" under such a regimen is often complex. Second, even if a protective effect against challenge is shown, it is not clear to what components of the immune system the protection is due. The protective effect could be due to antibodies, cells, mediators of the immune system or to combinations thereof. Thus, although this method of obtaining the screening reagent is sometimes used, it is time-consuming and does not permit identification of protective components.

A more useful manner of obtaining blood components and substantiating their protective effects takes advantage of implanted diffusion chambers containing the infectious agents, such as those described by Grieve, R. B., et al. *Am J Trop Med Hyg* (1988) 39:373–379, and by Abraham, D., et al., *J Parasit* (1988) 74:275–282. In the first of these papers, dogs which had been immunized against *Dirofilaria immitis* infection were supplied diffusion chambers containing infective larvae. The larvae in the chambers could then be evaluated for the effect of the previous immunizations. In the second paper referred to, mice were supplied diffusion chambers containing *D. immitis* third-stage larvae, and the effects on these larvae were used to determine the possible immunity of the mice putatively engendered by previous injections with L3. In the context of these papers, the use of the diffusion chamber containing the infectious agent, therefore, gives a convenient assessment of the effectiveness of certain directly administered active immunization protocols, but not of passively transferred protective effects of selected fractions of a target host bloodstream.

The general method of the invention is illustrated specifically below in the context of heartworm infection in dogs, a disease which is identified as one wherein the complexity of the parasitic infection makes the choice of a candidate immunogen for vaccination very difficult. Even naturally conferred immunity cannot be assured to exist, as dogs with previous or existing infections with *D. immitis* can be reinfected (Grieve, R. B., et al. *Epidemiologic Reviews* (1983) 5:220–246). However, this review also reports that there is some evidence of a naturally occurring protective immune response. This evidence is stated to be the apparent limitation on the population of mature worms in infected dogs.

Furthermore, it has been possible to induce protective immunity artificially. Wong, M. M., et al., *Exp Parasitol* (1974) 35:465–474, reported the immunization of dogs with radiation-attenuated infective larvae. The dogs were protected to varying degrees upon challenge. Blair, L. S., et al., in *Fifth International Congress of Parasitology*, Toronto, Canada (August 1982), reported successful immunization by infecting the dogs and terminating the infection at the fourth larval stage by chemotherapy.

Grieve, R. B., *Proc Heartworm Symp* (1989), pp. 187–190, reviewed the status of attempts to produce vaccines against heartworm in dogs. This report summarizes the use of infective larvae implanted in an inert diffusion chamber which permits the influx of cells and/or serum from the host and outflow of parasite material from the chamber to assess the effectiveness of inoculation protocols in both dogs and mice. The use of immunization with infective larvae was demonstrated to be partially effective in protection against subsequent challenge.

An alternative approach to finding a heartworm vaccine has been to attempt to identify prominent antigens in the infective stage of *D. immitis*. Philipp, M., et al., *J Immunol* (1986) 136:2621–2627, reports a 35 kD major surface antigen of *D. immitis* third stage larvae which was capable of immunoprecipitation with sera from dogs carrying an occult experimental *D. immitis* infection or with sera from dogs immunized by irradiated third stage larvae. In addition, this group reported (Davis, T. B., et al., Abstract 404, 37th Annual Meeting, Am. Soc. Trop. Med. Hyg. (1988)) three major surface proteins of the L4 stage of molecular weights 150 kD, 52 kD, and 25 kD. The 25 kD molecule seemed unique to the L4 stage.

Ibrahim, M. S., et al., *Parasitol* (1989) 99:89–97, using *D. immitis* L3s labeled with $^{125}$I, showed that a 35 kD and 6 kD component were shed into the culture medium by developing parasites. They further showed that antibodies from immunized rabbits and infected dogs immunoprecipitated the 35 kD, but not the 6 kD, component.

Scott, A. L., et al, *Acta Tropica* (1990) 47:339–353, reported characterization of the surface-associated molecules of L2, L3, and L4 of *D. immitis* by radiolabeling techniques and SDS-PAGE. They found major labeled components of 35 kD and 6 kD in extracts from iodine-labeled L2 and L3 stages; lactoperoxidase-catalyzed labeling revealed components of apparent molecular weights 66 kD, 48 kD, 25 kD, 16.5 kD, and 12 kD. Iodine labeling of surface-associated molecules of L4 gave molecules of apparent molecular weights of 57 kD, 40 kD, 25 kD, 12 kD, and 10 kD; lactoperoxidase-catalyzed labeling showed additional bands of 45 kD, 43 kD, and 3 kD. However, these were identified using uncharacterized serum sources or without serum identification.

Other approaches to obtaining vaccines against parasites in general have focused on the production of neutralizing antibodies. For example, both in vitro studies by Tanner, M., et al., *Trans Roy Soc Trop Med Hyg* (1981)75:173–174, and by Sim, B. K. L. et al., (ibid.) (1982) 76:362–370, and in vivo by Parab, P. B., et al., *Immunol* (1988) 64:169–174, have demonstrated that anti-bodies are effective alone or with other immune components in killing filarial L3 from *Dipetalonema (Acanthocheilonema) viteae* or *Brugia malayi*. Furthermore, passive immunity to *Schistosoma mansoni* has been transferred from immune rats or humans to normal mice (Sher, A. et al., *Parasitol* (1975) 70:347–357; Jwo, J. et al., *Am J Trop Med Hyg* (1989) 41:553–562). None of these studies involved recovery and evaluation of the infectious agent implanted in an in vivo incubator for the agent treated with candidate protective components.

DISCLOSURE OF THE INVENTION

The method included in the scope of the present invention provides a means to identify immunogens capable of protecting a susceptible host against infestation by nematodes which are parasitic to mammals. This method comprises first validating a reagent, such as serum or cells, which is capable of protecting a susceptible host against nematode parasitism. The reagent is validated by administering candidate cells or serum derived from an immune susceptible host into a neutral, nonsusceptible incubator animal. The incubator animal also contains a diffusion chamber implant containing the parasitic nematode. The effect of the putative protective reagent on the nematodes contained in the chamber can then be observed. Reagents comprising serum and/or cells which cause damage to the entrapped nematodes are then used to screen for candidate immunogens which can then be identified by their ability to bind the successful validated reagent.

Using this method, two related proteins have been isolated from the L3 and L4 larval stages of *Dirofilaria immitis*. These proteins show molecular weights of 22 and 20.5 kD by Tris-glycine gel electrophoresis and are first seen in the third stage larvae between 36 and 48 hr in culture after removal from the mosquito intermediate host. Both first appear in the excretory-secretory products of the larvae between 48 and 60 hr in culture, coincident with the beginning of the cuticular separation during the molt.

These two proteins have been purified, and their encoding cDNAs have been isolated and sequenced. The deduced amino acid sequences obtained from the cDNA clones shows that the 22 kD protein is identical with the 20.5 kD protein but further contains, at the N-terminus, a 21 amino acid hydrophobic leader sequence. The larger protein is processed in vivo yielding the 20.5 kD protein.

The molecular weights of these proteins calculated from the amino acid sequences are 17.5 and 15.3 kD, and Tris-tricine SDS-PAGE has given relative molecular weights of 16.1 and 18.8 kD. Sera from dogs immune to infection by *D. immitis*, validated by the invention method, recognize both proteins, while sera from infected non-immune dogs do not. These proteins are immunologically relevant and stage restricted.

Thus, in one aspect, the invention is directed to a purified protein which may be isolated from the L3 or L4 larval stage of a nematode parasitic in mammals, which protein is immunoreactive with serum or cells from a susceptible host, which is immune to parasitism by said nematode, and which comprises an amino acid sequence having a calculated molecular weight of about 15 kD. The corresponding protein, when produced in said larval stage, has a molecular weight of about 20.5 kD as measured by Tris-glycine SDS-PAGE and about 16 kD when measured by Tris-tricine SDS-PAGE. This amino acid sequence may further be extended by a hydrophobic leader sequence to yield, in the form naturally occurring in the L3 or L4 larval stage, a protein having an apparent molecular weight by Tris-tricine SDS-PAGE of about 19 kD and in Tris-glycine SDS-PAGE of about 22 kD. Preferred sources of these proteins are filarial nematodes, and, most preferably, D. immitis.

For convenience, these immunogens will be referred to as the 20.5 kD and 22 kD proteins, or 22/20.5 kD proteins.

In other aspects, the invention is directed to recombinant nucleic acids encoding the 20.5 kD and 22 kD proteins or immunogenic fragments thereof, to expression systems comprising control sequences operably linked to DNA encoding the 20.5 kD or 22 kD proteins or their fragments, to host cells containing the expression systems, and to methods to prepare these proteins using such host cells.

In still other aspects, the invention is directed to oligonucleotides capable of antisense or triple helix disruption of the expression of the genes encoding the proteins of the invention, and to methods to disrupt such expression.

Other aspects of the invention include vaccines comprising the invention proteins and expression systems, and to methods to elicit an immune response against infection by administering these vaccine compositions.

The invention also includes compositions consisting of antibodies immunoreactive with the proteins of the invention.

BRIEF DESCRIPTION OF THE DRAWINGS

FIG. 1 shows Western blots of D. immitis proteins immunoreacted with canine sera derived from immune and non-immune dogs.

FIG. 2 shows Western blots of D. immitis proteins immunoreacted with canine sera at various time points (days) after immunization.

FIG. 3 shows the results of SDS-PAGE on proteins labeled with S-35 methionine extracted from D. immitis L4 larvae and reacted with control and immune sera at various time points after immunization. Panel A shows protein immunoprecipitated on days 29, 142 and 345 and panel B, days 554, 642 and 783.

FIG. 4 shows the results of proteins analyzed as set forth in FIG. 3, but wherein the larval surface proteins are labeled with I-125. Panel A shows proteins immunoprecipitated on days 29, 142 and 345 and panel B, days 554, 642 and 783.

FIG. 14 shows SDS-PAGE of larval ES proteins eluted from a $C_4$ reverse phase column as shown in FIG. 13. Panels A and C show silver stained SDS-PAGE gels of fractions 99 through 107 of the early eluting peaks (panel A) and fractions 227 through 235 of the late eluting peaks (panel C), while panels B and D are autoradiographs of the same gels.

FIG. 19 A–D shows SDS-PAGE separation of larval ES proteins purified by cation exchange and reverse phase chromatography as shown in FIG. 18.

FIG. 20 shows immunoblot analysis of partially purified larval ES proteins.

FIG. 21 shows the amino acid sequences (SEQ ID NOS:1 through 20) obtained from the 20, 22L and 22U kD proteins of larval ES and adult D. immitis.

FIG. 22 shows Tris-tricine SDS-PAGE of the 20 and 22L kD proteins from larval D. immitis.

FIG. 26 shows the cloned DNA sequence (SEQ ID NO:21 and SEQ ID NO:22) and deduced amino acid sequence for the 20.5 kD and 22 kD proteins from D. immitis.

FIG. 28 shows the deduced amino acid sequence (SEQ ID NO:23) of the 20/22L kD protein in single letter code (upper case).

FIG. 29A–C shows the hydrophilicity plot and protein characteristics calculated for the sequences of the 20 and 22L kD proteins.

MODES OF CARRYING OUT THE INVENTION

Figure 5A:
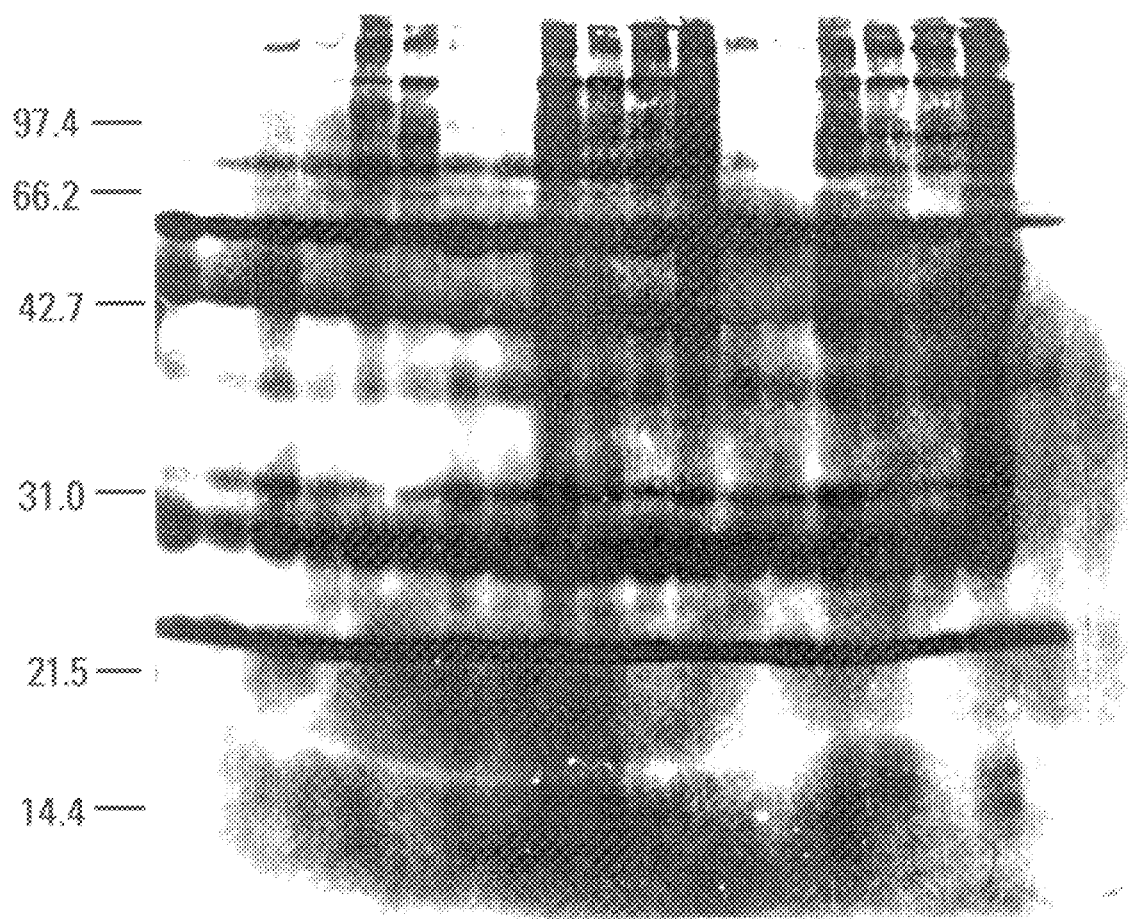
FIG. 5 shows the results of proteins analyzed as in FIG. 3, but wherein the larval surface proteins are labeled using biotin. Panel A shows proteins immunoprecipitated on days 29, 142 and 345 and Panel B, days 554, 642 and 783.

The invention is directed to immunogens which are useful in protecting susceptible mammalian hosts against infestation by parasitic nematodes. The particular immunogens described herein are designated the 22/20.5 kD proteins. Fragments of these proteins may also be included among the immunogens of the invention, provided they contain the requisite epitopes to elicit the desired immune response in the susceptible host.

By "22/20.5 kD protein" is meant proteins of these apparent molecular weights isolatable from the L3 or L4 larval stage of *D. immitis* or from related nematodes which are parasitic in mammals. The 22/20.5 kD proteins isolatable from *D. immitis* have the amino acid sequences shown in FIG. 26. As shown, the 20.5 kD protein is the cleavage product of the 22 kD protein wherein 21 amino acids of a leader sequence are deleted to yield the smaller protein. Although the calculated molecular weights of the *D. immitis* proteins are only 17.5 kD for the larger and 15.3 kD for the smaller protein, apparent molecular weights may be higher, depending on the particular system of measurement used.

The invention provides not only the 22/20.5 kD protein from *D. immitis*, but also the native DNA encoding these proteins. The availability of this DNA permits retrieval of homologous proteins from related nematode species. The DNA, or portions thereof, can be used as a probe under conditions of standard stringency appropriate for the library screened and the length of probe to isolate DNA encoding corresponding proteins in these related species. Suitable conditions of hybridization are set forth in, for example, "Molecular Cloning: A Laboratory Manual", 2nd ed, (1989) J. Sambrook et al, eds Colg Spring Harbor Press, and in "Current Protocols in Molecular Biology" Greene Publishing Associates and Wiley-Interscience, J. Wiley and Sons. Further, the antibodies immunoreactive with the 22/20.5 kD proteins of *D. immitis* may be used as screening tools for expression libraries prepared from these related species. Accordingly, as used herein, the "22/20.5 kD protein" refers not only to the proteins described herein isolatable from the L3 or L4 larval stages of *D. immitis*, but also to the corresponding peptides isolatable from the L3 or L4 larval stages of other nematodes which are parasitic to mammals. These corresponding proteins are encoded by nucleic acids which are capable of hybridizing under standard conditions to the DNA encoding the 22/20.5 kD proteins of *D. immitis*.

The 20.5/22 kD proteins from *D. immitis* are specifically immunoreactive with components of immune dog serum which have been validated as protective by the invention method. Similarly, corresponding proteins in other nematode species parasitic in mammals are specifically immunoreactive with protective components of immune members of the relevant mammalian species, validated by the invention method.

The invention, therefore, provides access to a group of proteins which are contained in the L3 or L4 larval stages of nematodes which are parasitic in mammals and which are useful in preparation of vaccines protective against these parasites.

In addition to the proteins themselves, expression systems which provide these protein in situ are also useful as vaccines. Such vector-based vaccines are generally known in the art and include, for example, vaccines based on Vaccinia vectors.

In addition, the availability of the native nucleic acid sequences encoding the proteins of the invention provides the information required to design oligonucleotides which inhibit the production of the 22/20.5 kD proteins. These oligomers may be "antisense" oligomers which are complementary to the single strand encoding these proteins or to the related regulatory sequences included in the RNA, or may be capable of forming triple helices with the duplex gene either in the coding region or in the regulatory regions thereof.

The availability of the purified 22/20.5 kD proteins also permit the preparation of antibody compositions which consist of antibodies immunoreactive with these proteins. Although such antibodies may exist natively in infected mammals, only the availability of the purified proteins permits isolation of compositions wherein all contained antibodies are immunoreactive with these proteins.

Further, as is understood in the art, only particular immunogenic fragments of the proteins are necessary to elicit an immune response. Accordingly, the invention includes such fragments.

General Description and Definitions

The practice of the present invention will employ, unless otherwise indicated, conventional biochemistry, immunology, molecular biology and recombinant DNA techniques within the skill of the art. Such techniques are explained fully in the literature. See, e.g., Maniatis et al., Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The following terminology will be used in accordance with the definitions set out below in describing the present invention.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" control sequences when expression of the coding sequences is effected when the expression system is contained in an appropriate host cell.

A "host cell" is a cell which has been modified to contain, or is capable of modification to contain, an exogenous DNA sequence.

A "heterologous" region of a DNA construct is an identifiable segment of DNA within or attached to another DNA molecule that is not found in association with the other molecule in nature.

A "nematode parasitic in mammals" refers to a nematode which is capable of a parasitic relationship with a mammalian host. Preferred among nematodes parasitic in mammals are filarial nematodes as described hereinbelow.

The immunogens of the invention, including the 20.5/22 kD protein and their immunogenic fragments, are "specifically immunoreactive with validated components of immune host serum or tissue". "Validated components" are components which have been shown in the method of the invention, as described herein, to exert a deleterious effect on the parasitic nematodes when supplied in a diffusion chamber to a neutral host which has been administered the component. By "specifically immunoreactive" is meant that the immunogen is capable of binding the validated component as derived from an immune susceptible host, but is incapable of binding components found in nonimmune counterparts in this species.

By "susceptible host" is meant a host species that is ordinarily susceptible to infestation by the nematode parasite in question. Individual members of the susceptible host species may have acquired immunity to this infestation.

By "DNA region which effects production" of a protein is meant those portions of genomic DNA which include the genes encoding the protein and regions regulating expression of said encoding gene.

Validation and Identification Method

The 20.5/22 kD proteins of the invention are identified by a method that takes advantage of an in vivo model system. This model system has been used previously to evaluate immunization protocols using the active response of the model susceptible host, but not to ascertain or validate the protective capacity of specific immune reagents generated in the natural target host and passively transferred into the experimental animal system. Thus, the method has not been used to identify suitable reagents which themselves are useful to identify and evaluate vaccine candidates. The active immunization model as applied to heartworm is described in the 1988 papers of Grieve and Abraham cited above.

In the present model, a neutral, nonsusceptible host is used as an incubator for a diffusion chamber containing the parasitic nematodes against which protection is desired and is also administered candidate components derived from immune, susceptible hosts for evaluation of these components. Successfully protective components are capable of exerting deleterious effects on the caged parasitic nematodes. The diffusion chamber can be removed to evaluate these effects. Thus, components which are truly protective against the parasitic nematode can be validated. The validated components can then be used to test their specific immunoreactivity with respect to the immunogen to be identified. Immunogens which bind the validated components are successful vaccine candidates.

In one embodiment of this validation system, the parasitic nematodes are *D. immitis*. The parasitic nematodes, third-stage larvae, were first obtained as follows. *D. immitis* was maintained in a dog infected with parasites which had been passed once from an infection obtained through the U.S.-Japan Cooperative Medical Sciences Program, National Institutes of Health. *Aedes aegypti* mosquitos Liverpool (blackeye strain) were infected with the parasite by feeding on microfilaremic blood using the artificial feeding apparatus described by Rutledge, L. L., et al., *Mosq News* (1964) 24:407–419. Fifteen days after infection, the mosquitoes were cold-anesthetized and surface sterilized by immersion in 95% ethanol followed by a 3 min wash in 1% benzalkonium chloride in 0.01M phosphate-buffered saline, pH 7.2. The mosquitoes were washed three times in PBS and incubated over a 60 mesh screen inside a funnel filled with medium (the medium was described in Abraham, D. et al., *J Parasitol* (1987) 73:377–383) and the larvae were collected 90 min after incubation.

The recovered L3 larvae were then placed in diffusion chambers and implanted subcutaneously. For implantation in dogs, chambers were composed of two 14 mm Lucite rings sealed with 5.0 μm hydrophilic Durapore membranes (Millipore, Bedford, Mass.). The larvae were inserted through a hole in one of the Lucite rings which was subsequently sealed with nylon thread. The dogs were anaesthetized and a subcutaneous pocket was formed in the dorsal skin of the neck; the chamber was implanted in the pocket and the wound closed with suture.

For implantation in mice using the invention method, similar chambers were used and implanted into a subcutaneous pocket formed laterally to the lumbar spine. The chambers can be removed at the desired time for evaluation of the contained larvae. A variety of chamber designs can be used, and the porosity of the diffusion membrane was chosen according to the nature of the infectious agent and desired limitation on the nature of the inward diffusion.

In the use of the method to prepare screening reagents or to evaluate samples from target animal hosts, the diffusion chambers are allowed to remain in vivo in an irrelevant host which has not been actively immunized and a portion of serum or other component believed to be capable of conferring protective immunity is administered to the irrelevant host. A portion is retained for use in the invention method to screen immunogens if destruction or impairment of infectious agent is shown. For the previous work in dogs, for example, about 0.5 ml of serum, for example, was administered by placing the serum in the pocket along with the diffusion chamber. For mice, similar amounts but fewer chambers were used as compared to the previous work in dogs. The chamber containing the parasitic nematodes is allowed to remain in place for a time sufficient to evaluate the protective effects of the serum or other component generally obtained from an immune natural target host. This time is determined by the nature of the infection and the protective capacity of the test sample.

After the required experimental time has lapsed, the chamber is removed and the parasitic nematodes are retrieved. The protective capacity of the passively transferred components from the natural target host is evaluated by any deleterious effects seen in the parasitic nematodes. These effects may include, but are not limited to, such parameters as killing, stunting, alterations in normal morphology, alterations in measurable metabolism, failure to mature in in vitro culture, and failure to infect conventional target hosts.

A fraction of the sample which has been retained during the evaluation is then used to screen candidate immunogens. Any technique which results in the complexation of the validated component with the candidate immunogen can be used. For example, an extract of the nematode is subjected to resolution using a variety of chromatographic techniques, including size separation using gel permeation chromatography, electrophoresis on polyacrylamide gels, ion exchange chromatography, affinity chromatography, and the like. The whole extract or resolved extract is then tested for reactive effect with the protective component. If serum is the protective component, a complex will be formed. If the component is a cell subfraction with receptor for antigen, the antigen will be bound. The complex is recovered, and the immunogen recovered from the complex.

In applying the method to screen crude extracts for immunogens, the protective serum or cells can be used as an affinity ligand in chromatographic techniques to isolate immunoreactive components. Alternatively, as set forth above, the extract can first be resolved and the appropriate fractions identified by complexation with the protective cells or serum.

In an alternative approach, the protective cells or serum can be used as a screening reagent for a cDNA library prepared from the infectious stage or later stage of the parasitic nematode which is constructed in expression vectors. A commonly used and convenient such library is the λgt11 library described by Young, R. A., and Davis, R. W., *Proc Natl Acad Sci USA* (1983) 80:1194–1198. The expression library is plated and screened with the protective cells or serum to identify colonies which produce immunoreactive components. The positive colonies are then purified, and the cDNA inserts in the expression vectors recovered and sequenced to identify the encoded proteins.

The cDNA inserts identified as expressing immunogens using the reagent of the invention can then be ligated into alternative conventional expression systems for production of the proteins useful as vaccines. Alternatively, the inserts may be ligated into expression systems which are live recombinant carriers such as Sindbis virus, vaccinia virus or other pox viruses, Herpes viruses, Adenoviruses, Salmonella or Mycobacteria. These infectious agents can then be used directly to immunize the target hosts by generation of immunogen in situ.

The foregoing approach is applicable to the discovery of suitable immunogens for any disease wherein the parasitic nematodes can conveniently be used in the animal model. In general, such diseases are those caused by organisms of sufficient size to be retained in a diffusion chamber. Thus, in general, the method is applicable to a variety of parasitic diseases including those caused by other filarial nematodes, such as *Dipetalonema perstans, Dipetalonema streptocerca, Wuchereria bancrofti, B. malayi, Mansonella ozzardi, Loa loa*, and *O volvulus.*

Other parasitic mammalian nematodes to which the method is applicable include Strongyloides spp., Strongylus spp., Haemonchus spp., Trichostrongylus spp., Ostertagia spp., Cooperia spp., Dictyocaulus spp., Nematodirus spp., Cyathostominae (small strongyles of horses), Oesophagostomum spp., *Chabertia ovina*, Ancylostoma spp., Uncinaria spp., Bunostomum spp., Filaroides spp., *Aelurostrongylus abstrusus*, those nematodes of the Order Ascaridida (Ascarids), *Trichinella spiralis*, Trichuris spp., Angiostrongylus spp., *Enterobius vermicularis*. In applying the method, the infectious stage of the agent is determined, if applicable, for identification of the form to be enclosed in the chamber. Protocols are adjusted to take account of the time required for exertion of the protective effect of the target animal-derived component, such as cells or serum.

Preparation of the 20.5/22 kD Protein

Using the invention reagent, several immunogens associated with *D. immitis* were obtained. One class of such immunogens have molecular weights of 66 kD, 65 kD, 59 kD, 39 kD, 33 kD, 23/24 kD, 22/20.5 kD and 14 kD. The foregoing proteins are produced by L3 and/or L4 larvae. DNAs encoding these proteins can be recovered from cDNA expression libraries prepared from the mRNA of these larval stages by screening for expression with the reagent of the invention. The appropriate cDNA inserts can then be used to produce recombinant immunogen in a suitable expression system which yields practical amounts of the protein or can be ligated into recombinant systems which generate the immunogen in situ, such as the vaccinia virus system. Oligopeptides containing immunogenic epitopes can also be prepared synthetically by known techniques. See, e.g., U.S. Pat. No. 4,735,896.

As the 20.5/22 kD proteins are produced by L3 and/or L4 larvae, DNAs encoding these proteins can be recovered from cDNA expression libraries prepared from the mRNA of these larval stages by screening for expression with the reagent of the invention. The appropriate cDNA inserts can then be used to produce recombinant immunogen in a suitable expression system which yields practical amounts of the protein or can be ligated into recombinant systems which generate the immunogen in situ, such as the vaccinia virus system.

The DNA encoding the 20.5/22 kD *D. immitis* protein has been obtained as described in the examples herein below. The availability of the native coding sequence makes possible the screening and retrieval of the corresponding proteins of approximately 20.5/22 kD from L3/L4 larval stages of related nematodes which are parasitic in mammals. The retrieved *D. immitis* DNA or a fragment thereof of at least about 11 bases may be used as a probe under standard hybridization conditions to identify DNA encoding the corresponding protein in these related larvae using genomic or cDNA libraries. The DNA encoding the *D. immitis* or corresponding proteins may be prepared using standard biochemical synthesis techniques and may, of course, contain modifications consistent with the degeneracy of the genetic code. The sequence obtained may be amplified using cloning vectors or PCR techniques. The prepared and amplified DNA encoding the immunogen or suitable immunogenic fraction thereof may be included in expression systems for production of the protein wherein any degenerate form may be used, or the DNA, as naturally occurring, can be used for the design of antisense sequences useful for regulating the expression of the gene or for the design as oligomers which bind to the duplex responsible for the production of the protein.

Recombinant larval immunogens, and, in particular, the 22/20.5 kD proteins, can be produced by constructing an expression system and modifying a host cell to contain this system to provide a cell line or culture capable of expressing DNA encoding the desired protein. DNA encoding the desired proteins or fragments can either be prepared directly by synthetic methods based on the native sequence (or equivalent sequences encoding the same amino acids), or by using the native sequence to design oligonucleotide probes to clone coding sequence using known techniques. See, e.g., Mayfield et al, *J Virol* (1983) 4:259–264. The coding sequence can be comprised entirely of protein-encoding sequences, or such sequences can be fused to other sequences (e.g., leader sequences) so that a fusion protein is encoded. See, e.g., U.S. Pat. Nos. 4,431,739; 4,425,437; 4,338,397. Synthetic coding sequences will also allow for the convenient construction of coding sequences which express protein analogs or "muteins". Alternatively, coding sequences for muteins can be prepared by site-directed mutagenesis of native nucleotide sequences. The techniques of site-directed mutagenesis are known in the art. The coding sequence for the *D. immitis* 20.5 kD or 22 kD proteins shown in FIGS. 25 and 27 may be prepared by biochemical synthesis or isolated from the L3 and L4 larvae as described above. The DNA can be amplified in a cloning vector or by PCR.

To complete construction of an expression system, the coding sequence as described above for the larval immunogens is then operably linked to control sequences (e.g., a promoter, etc.), so that the DNA sequence encoding the subunit antigen is transcribed into messenger RNA in the host cell transformed by the expression system.

For expression in a procaryotic or yeast cell, the promoter and other control sequences are necessarily heterologous to the subunit antigen coding sequence. For expression in a mammalian cell, the control sequences can be homologous larval immunogen sequences, or preferably heterologous mammalian control sequences. The expression system is constructed as a discrete molecular entity flanked by convenient restriction sites; alternatively, it is constructed by inserting the coding sequence into a previously constructed expression vector with an appropriate insertion site.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Publication Nos. GB2,121,054; GB2,008,123; GB2,007,675; and European Publication No. 103,395. The preferred procaryotic expression vectors are those for *E. coli*. Other preferred expression vectors are those for use in eucaryotic systems. Yeast expression vectors are also known in the art. See, e.g., U.S. Pat. Nos. 4,446,235; 4,443,539; 4,430,428; see also European Publication Nos. 103,409; 100,561; 96,491.

A preferred expression host for the present invention is mammalian cells. Appropriate mammalian expression hosts include kidney cell lines (e.g., CV-1 monkey kidney cell lines), fibroblast cell lines (e.g., human, murine or chicken embryo fibroblast cell lines), Chinese hamster ovary (CHO) cells, HeLa cells, mouse NIH/3T3 and/or $LMTK^{31}$ cells. Alternatively, the larval immunogens may be expressed as heterologous protein in myeloma cell lines employing immunoglobulin promoters. See, e.g., Banerjle et al. *Cell* (1983) 33:729–740; U.S. Pat. No. 4,663,281. Mammalian expression vectors employing viral promoters (e.g., SV40 early region promoter, Rous sarcoma virus, LTR promoter, etc.) are also well known in the art. See, e.g., Pachl et. al., *J Virol* (1987) 61:315–325; Gorman et. al., *Proc Natl Acad Sci USA* (1982) 79:6777–6781; Southern et. al., *J Mol App Genet* (1982) 1:327–341; PCT Publication No. WO87/02062. Preferred eucaryotic expression vectors employ the vaccinia virus, the SV40 virus, or the Rous sarcoma virus. See, e.g., Mackett et al., *J Virol* (1984) 49:857; DNA Cloning, vol. II, pp. 191–211, supra; PCT Publication No. WO086/07593; Chakrabarty et al., *Mol Cell Biol* (1985) 5:403.

A host cell that has been stably transformed by an expression system for the subunit antigen is then selected to produce the recombinant polypeptide.

In general, techniques for construction of expression system, modification of cells to contain these systems, culture of such cells in retrieval and isolation and purification of the protein produced are understood in the art. The protein can be purified from lysate or medium as appropriate. The resulting 20.5/22 kD proteins or fragments thereof which are immunogenic may then be used for preparation of protective vaccines or for purification of antibodies which are immunoreactive with these immunogens. Compositions of these antibodies are useful in diagnostic tests.

Regulation of Expression

It may be desirable to interrupt the life cycle of the parasitic nematode by inhibiting the expression of the gene encoding the 20.5/22 kD protein. As described above, the invention provides the native DNA sequence encoding the 20.5/22 kD protein of *D. immitis*, which can, in turn, be used as a probe to retrieve corresponding native sequences from related species. Such retrieval involves the use of hybridization of the probe to the cDNA or genomic libraries of these related nematodes under standard hybridization conditions. Thus, the disclosure of the invention makes available the native DNA sequences encoding the 20.5/22 kD protein of nematodes parasitic in mammals in general.

The availability of these native sequences also makes possible the design of suitable antisense and triple helix-forming oligonucleotides which can interrupt the expression of the gene.

Antisense oligonucleotides are generally designed as complements to the messenger RNA encoding the desired protein. The complement binds through Watson-Crick base-pairing to the mRNA interfering with translation either by enhancing mRNA degradation by RNAse H, by preventing or inhibiting processing to mature RNA, or by preventing translation. The oligonucleotide may bind either to the translated region or to control sequences in the mRNA.

Similarly, as the transcription of DNA involves partial disassembly of the double helix, antisense oligonucleotides may also bind to transcribed or nontranscribed regions of the DNA to inhibit transcription. Absolute homology between the target and the antisense sequences is preferred but not required for the inhibition. Holt, J. T. et al., *Proc Natl Acad Sci* (1986) 83:4794.

Oligonucleotides may also be designed to form a triplex DNA structure with the intact duplex gene according to certain binding rules. Moffat, A. S., *Science* (1991) 252:1374–1375. When this triplex structure is formed in the promoter region of a gene, it has been shown to disrupt transcription of that gene. Orson, F. M. et al., *Nuc Acids Res* (1991) 19:3435–3441. Again, the oligomer designed to form a triplex can be designed to bind the duplex gene in either regulatory or transcribed regions or both.

The invention, therefore, also includes methods to interfere with the production of the 20.5/22 kD protein by use of the antisense or triple helix-forming techniques. The relevant oligomers may be administered to a host harboring the parasite in order to effect this control.

Preparation of Antibodies

The availability of purified 20.5/22 kD protein makes possible the production of compositions of antibodies consisting of antibodies which bind these proteins. Standard immunoaffinity chromatography techniques can be employed for this purpose. The resulting compositions are useful in quality control assays for preparation of the immunogens, as well as in diagnosis.

Additionally, the production of monoclonal antibodies reactive with a purified immunogen is within the skill of the art. A mammal, such as a mouse, is immunized with the 20.5/22 kD nematode larval protein, or fragments containing the relevant epitopes can be employed. Antibody-producing B lymphocytes are recovered from the animal and immortalized by, for example, fusion with a continuous cell line to produce an immortal antibody-producing cell line; i.e., a hybridoma, trioma, etc. Immortal, antibody-producing cell lines can also be created by techniques other than fusion, such as direct transformation of B-lymphocytes with oncogenic DNA, or transfection with Epstein-Barr virus. See, e.g., M. Schreier et al., Hybridoma Techniques (1980); Hammerling et al., Monoclonal Antibodies and T-Cell Hybridomas (1981); Kennett et al., Monoclonal Antibodies (1980); see also U.S. Pat. Nos. 4,341,761; 4,399,121; 4,427,783; 4,444,887; 4,451,570, 4,466,917; 4,472,500; 4,491,632; 4,493,890. After screening, monoclonal antibody is harvested from the immortalized cell lines utilizing conventional separation and purification techniques.

Vaccines

The larval immunogens may also be formulated into a vaccine composition comprising a pharmaceutically acceptable vehicle and, optionally, an adjuvant. Such formulations are well within the skill of the art. In general, the formulations will be particularly adapted for intramuscular injection, since intravenous injection is usually not practical for large-scale application to domestic animals. Alternatively, the vaccines are given orally, and the subunits formulated with a suitable oral carrier. It may be preferred to administer the vaccines of the present invention orally to raise mucosal immunity, as well as intramuscularly for systemic immunity.

A pharmaceutically acceptable vehicle, suitable for parenteral injection, is usually nontoxic and nontherapeutic. Examples of such vehicles are water, saline, Ringer's solution, dextrose solution, and Hank's solution. Nonaqueous vehicles, such as fixed oils, sesame oil, ethyl oleate, or triglycerides may also be used. Parenteral vehicles may also take the form of suspensions containing viscosity enhancing agents, such as sodium carboxymethylcellulose, sorbitol, or dextran. The vehicle will also usually contain minor amounts of additives, such as substances that enhance isotonicity and chemical stability. Examples of buffers include phosphate buffer, bicarbonate buffer and Tris buffer, while examples of preservatives include thimerosal, m or o-cresol, formalin and benzyl alcohol. Standard formulations will either be liquid injectables or solids which can be taken up in a suitable liquid as a suspension or solution for injection. Thus, in a non-liquid formulation, the vehicle may comprise dextrose, human serum albumin, preservatives, etc., to which sterile water or saline could be added prior to administration.

Adjuvants are known in the art which can also be employed at an appropriate concentration in the vaccine formulations of the present invention; e.g., Freund's adjuvant, avridine, aluminum salts [$Al(OH)_3$, $AlPO_4$, $Al_2(SO_4)_8$], $Ca_3(PO_4)_2$, saponin, DDA, Plusonics, oil-in-water emulsions (containing, e.g., avridin, dextran sulfate or vitamin E) and water-in-oil emulsions (containing, e.g., polysorbate 80).

Many protocols for administering the vaccine composition of the present invention to animals are within the skill of the art. The preferred route to administration is parenteral, particularly intramuscular. The concentration of the subunit antigen(s) in the vaccine composition is selected so that an effective dose is presented in the host to elicit antibodies to the polypeptide neutralizing epitopes. Within wide limits, the dosage is not believed to be critical. Typically, the vaccine composition is administered in a manner which will deliver between about 1 to about 1,000 ug of the larval immunogen in a convenient volume of vehicle (e.g., about 1–10 ml). Preferably, the dosage in a single immunization will deliver from about 1 to about 500 $\mu$g of larval immunogen, more preferably about 5–10 to about 100–200 $\mu$g (e.g., 10–100 $\mu$g). It may also be preferred, although optional, to administer a second, booster immunization to the animal several weeks to several months after the initial immunization. To insure sustained high levels of protection against disease, it may be helpful to readminister a booster immunization to the animals once every year.

The vaccines of the invention are administered in a manner consistent with the nature of the vaccine and the nature of the disease and subject. If the recombinantly produced or native immunogens are administered as proteins, they are formulated with conventional excipients for injection or other systemic administration to the host. In addition to injection, formulations may be prepared for other administration methods which include transmucosal or transdermal delivery into the bloodstream.

The recombinant expression systems described herein may be included in infectious agents to provide the vaccine which will produce the protein in situ. Such vaccines have been constructed, for example, using the vaccinia virus. If the immunogens are administered in the form of recombinant DNA expression systems in infectious agents, administration is typically by injection or other mode of conventionally administering the infective agent.

The following examples are intended to illustrate but not to limit the invention.

EXAMPLE 1

Production of Sera for Passive Transfer

Four dogs were immunized with chemically-abbreviated infections, and two dogs served as chemically-treated controls. The dogs were housed in indoor mosquito-free individual cages at a temperature of 22° C. and 40–65% humidity. On day 532, post initial immunization, each dog was challenged with 100 L3 *D. immitis* larvae contained in 5 diffusion chambers, described above. Concomitant with chamber implantation, the dogs were injected subcutaneously with 50 L3 and the infection was allowed to proceed beyond the anticipated pre-patent period. Challenge infections were repeated on day 588 with 100 larvae within diffusion chambers and 30 L3 inoculated subcutaneously. Serum was collected at numerous time points from the immunized dogs, including 554, 588, 602 and 642 days after initial immunization which corresponded to days 22, 56, 77 and 117 after initial challenge. The isolation of serum provides a source of immunoglobulins and soluble factors, but not of cells. Antibody levels were measured to L3 and L4 surface antigens using an indirect fluorescent antibody assay and to L3 and L4 soluble antigens and an excretory-secretory antigen fraction by an indirect ELISA, as described by Grieve et al., (1988) (supra). The sera were pooled and validated as a significant factor in the protective effect in the mouse incubator as described in Example 2.

EXAMPLE 2

Validation in Mouse

A subcutaneous pocket was formed in male Balb/C BYJ mice approximately 10 weeks old and 20 L3 inoculated into diffusion chambers as described above were implanted into the pocket, along with 0.5 ml of the demonstrated protective serum to be tested. Serum samples were retained for future use. The diffusion chambers were re-covered two or three weeks later. Living larvae in the chambers were counted and placed into glacial acetic acid followed by 70% ethanol containing 5% glycerin. The ethanol was allowed to evaporate leaving the larvae in glycerin; the larvae were measured using projected images in the Macmeasure image analysis system on a Macintosh computer.

Three groups were used: experiment 1 used equal portions of serum from individual dogs at each of the three collection points described in Example 1 (days 56, 77 and 117). In experiments 2 and 3 only sera from immune dogs 117 days after initial challenge were used. Control sera were used in all cases; in experiment 2 this was a pool from 12 naive dogs; in experiment 3 from an individual dog. These groups also contained controls which received no serum.

In experiment 1, chambers were recovered two weeks post-inoculation. The survival rate of larvae in chambers from mice receiving serum from immune dogs were lower than those from mice receiving normal dog serum, but the difference was not statistically significant. Also, no difference was seen between the length of larvae in each case.

In experiments 2 and 3, the chambers were recovered three weeks after infection. There were significant differences in the larval recoveries between those receiving serum from naive dogs and those from immune dogs—about 34–33%. The lengths of the larvae were also significantly shorter in those chambers receiving sera from immune dogs.

EXAMPLE 3

Identification of Antigens

Crude extracts of L3 and L4 larvae were prepared as follows:

All procedures are performed at 4° C. or on ice. The worms were collected and washed twice with wash buffer (PBS/0.1% Triton X-100) and then with extraction buffer (0.05M Tris/HCl, pH 6.8; 2% CHAPSO; 1 mM PMSF; 1 mM EDTA; 1 mg/l leupeptin; 1 mg/l pepstatin). (Other detergents may be used in place of CHAPSO, including 0.5% Triton X-100, 0.5% CTAB, 2% DOC, or 2% SDS/5% 2-ME/8M urea.)

The worms are then homogenized 5× for 1 minute each, with 1 minute rest periods, using 250 to 500 $\mu$l for 10,000–20,000 worms (~500 μg). This volume is transferred to an additional tube, and the homogenizer washed with a clean 100–250 μl of extraction buffer and the wash pooled with the homogenate. The tube is rocked 4 hours-overnight and centrifuged at 12,000 g for 10 minutes. The supernate is harvested and the pellet is washed once with extraction buffer and saved for additional extractions if desired. The combined total volume of extract is less than 1 ml and about 20 ng of protein is solubilized per L4 larva used.

The procedure for L3 is identical, except that the wash buffer is PBS without detergent.

The extracts were subjected to polyacrylamide gel electrophoresis and tested with portions of the serum shown to be protective in the murine model. When pooled canine sera which had been shown to stunt larval growth as described in Example 2 were used as the immunoreactant in the Western blots, the results were as shown in FIG. 1. The 39 kD band shown in FIG. 1 is separated from a 45 kD band when a second dimension is added to the electrophoresis. This 45 kD protein is not immunoreactive. As seen, the serum is specifically immunoreactive with a 39 kD protein present in the L4 larval stage. This protein has a pI of about 5. Control serum shows no immunoreactivity with this protein. Reactivity to the 39 kD molecule is present in immune dogs, but not in control dogs. Sera from dogs with microfilaremic infection or amicrofilaremic infection do not recognize this molecule.

In addition, bands were present at 66 kD, 24/23 kD, and 14 kD, as shown in FIG. 2.

The proteins associated with the larval stages were also metabolically labeled using S-35 methionine; or the surfaces were labeled, prior to extraction, with I-125 or with biotin. For labeling with S-35 methionine, the radiolabeled amino acid was added to the parasites after 48 hrs in culture according to the method of Abraham, D., et al., *J Parasitol* (1987) 73:377–383. For labeling with I-125, the method of Mok, M., et al., *Molec Biochem Parasitol* (1988) 31:173–182, was used. For biotinylation, a modification of the method of Alvarez, R. M., et al., *Molec Biochem Parasitol* (1989) 33:183–190, was employed. In the modified procedure, NHS-longchain biotin was substituted for biotin per se.

Thus, additional identification could be had using these prelabeled proteins which immunoprecipitated with the successfully validated immune serum. These results are shown in FIGS. 3, 4 and 5. As shown in FIG. 3 in which panel A shows labeled proteins immunoprecipitated on days 29, 142 and 345 and panel B, days 554, 642 and 783, additional candidates are found at 59 kD and 16 kD, as indicated by the arrows. The radioactive iodine-labeled material shows a candidate at about 33 kD with a higher molecular weight smear at 35.8–34.5 kD. This was present beginning at day 345 and persisting until day 642 in some, but not all, immune dogs. An additional band was present at 14.5 kD. This is indicated in FIG. 4 in which panel A shows labeled proteins immunoprecipitated on days 29, 142 and 345 and panel B, days 554, 642 and 783.

FIG. 5 shows the results when the proteins were labeled by biotinylation in an enhanced chemiluminescence assay. Panel A shows protein immunoprecipitated on days 29, 142 and 345 and panel B, days 554, 642 and 783. A transient band represented by 65.3 kD was recognized by 3 of 4 immune dogs.

In addition, passive transfer of the earliest immune dog serum which showed uniform responses to the 39 kD protein (i.e., the day-142 immune serum shown in FIG. 3) was able to effect killing of the entrapped larvae; recoveries of intact larvae were only 58.3% in the case of immune serum compared to 65.8% for controls.

To summarize, the following antigen candidates were obtained:

A 39 kD protein which reacted with sera from all immune dogs but not with sera from naive cohorts. The protein is shown to be present in Western blots obtained from L4 soluble antigen and solubilized L4 larval pellets and is shown to be present, although apparently to a lesser degree, in L3. This protein appears to be absent from adult *D. immitis* and the microfilariae. It is clearly a distinct protein from the p35 protein described by Scott, A. L., et al., *Acta Tropica* (1990) (supra), and is relatively acidic, having a pI of approximately 5.

A 14 kD immunogen is detected with immune dog serum using Western blots and immunoprecipitation employing S-35 and iodine-labeled components. The protein is detected with immune dog serum, but not by serum from controls.

Additional proteins detected are of 66 kD and 23/24 kD.

Figure 6:
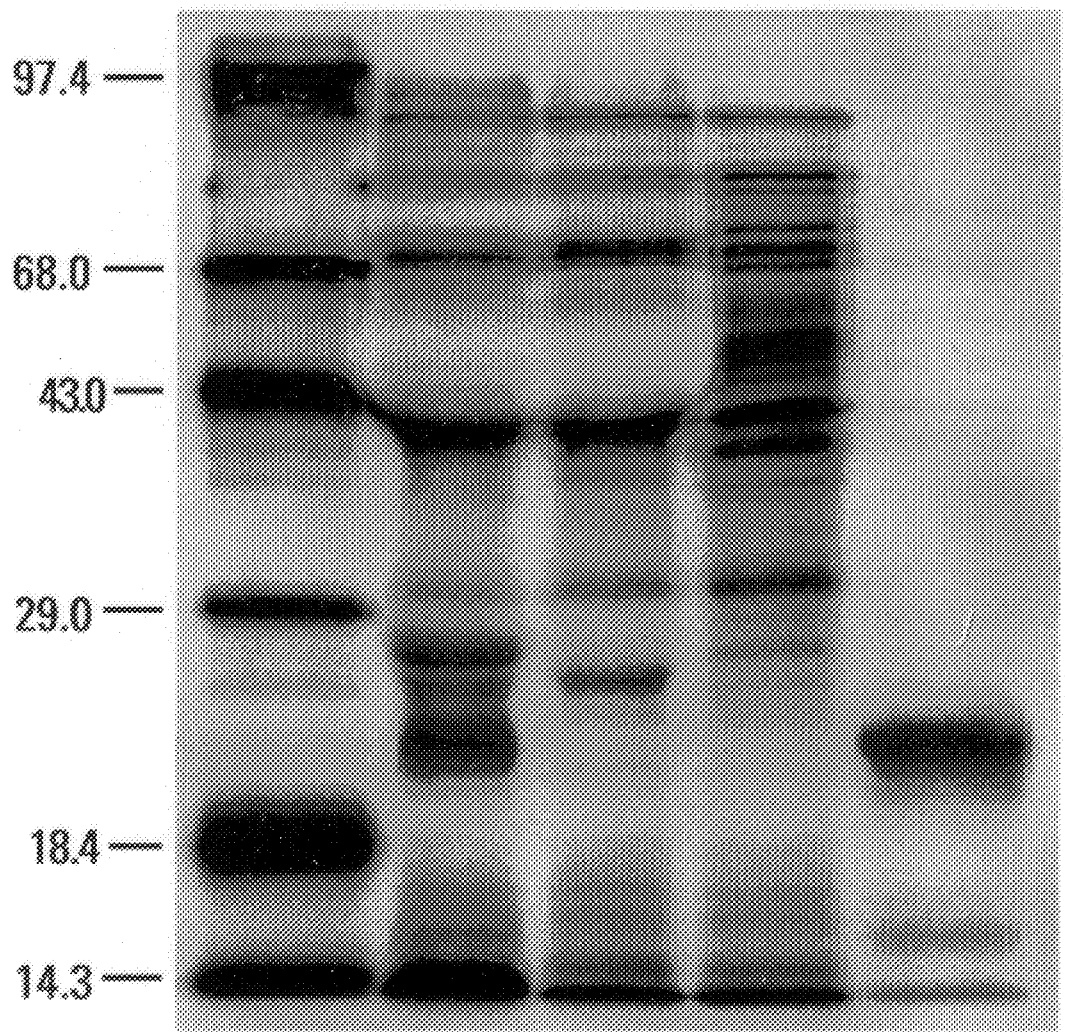
FIG. 6 shows the results of analysis of proteins present in the excretory/secretory material which characterizes the transition from L3 to L4 and maintenance of L4's for 3–4 days thereafter.

Another potential source of protective antigens in parasitic diseases are excretory/secretory products which are associated with various stages of the parasite. The transition between L3 and L4 involves excretion/secretion of a number of proteins which are harvested as follows: Larvae are cultured at 250–400 /ml, washed at 48 hr and cultured an additional 4 days. The worms are then settled out and the supernate collected. This is filtered through a 0.45 μm filter and protease inhibitors added as in L4 solubilization. The ES is then concentrated and buffer exchanged by ultrafiltration over a 10 kD membrane (Amicon Centriprep-10 and/or Centricon-10). The final buffer is 0.05M Tris/HCl pH 6.8 with protease inhibitors. Yields may be app. 5 ng/larvae. Final volume frequently 150–250 μl. This extract, referred to as DILEX, was prepared using larvae which were metabolically labeled with S-35 methionine and tested with respect to immune and control sera from dogs. The immune serum was that obtained on day 554 post immunization as set forth in Example 3. Immunoprecipitation with respect to the immune serum was obtained at 22/20.5 kD and 14.3 kD, as shown in FIG. 6. In FIG. 6, lane 1 shows molecular weight standards; lane 2, the immunoprecipitates from immune dog; lane 3, from control dog; lane 4, bead control; and lane 5, DILEX itself.

EXAMPLE 4

Isolation of cDNA's and Genes Encoding Potential *D. immitis* Protective Immunogens Genomic and cDNA expression libraries in λZapII (Short, J. M., et al., *Nucleic Acids Res* (1988) 16:7583–7600), a derivative of λgt11, were prepared from total genomic DNA, or L4 or L3 larval stage mRNA's, respectively, using standard procedures (*Short Protocols in Molecular Biology* (1989) Ausubel, M. F., et al., eds.) Screening of these libraries with pooled immune dog sera permits identification of clones which contain candidate antigens. The clones identified as immunoreactive with the immune serum provide a source of DNA encoding desired proteins which can conveniently be produced as fusion proteins in *E. coli*.

EXAMPLE 5

Construction of GST Fusion Proteins

The DNA inserts are recovered from the λZapII phagemid by digesting with EcoRI and XhoI and purified using agarose gel electrophoresis. The purified DNA is ligated into the expression vector pGEX-3x such that when the plasmid is expressed in *E. coli* the protein encoded by the DNA insert produces a fusion protein with glutathione-S-transferase. This procedure is described in detail by Smith, D. B., et al., *Gene* (1988) 67:31–40. Plasmids containing the DNA inserts are transformed into *E. coli* and successful transformants are grown in the presence of IPTG. The induced fusion protein is purified from the lysate by affinity chromatography with glutathione-beads as described by Smith et al. (supra).

EXAMPLE 6

Metabolic Labeling of *D. Immitis* Larvae

Larvae and ES proteins were pulse chase labeled as described by Frank, G. R. and Greive, R. B., *J Parasitol* (1991) 77:950–956, incorporated herein by reference. A master culture was initiated in Seru-Max™ supplemented NI and larvae were removed at 0, 12, 24, 36, 48 and 60 hr. After removal the larvae were labeled with Translabel™ in Seru-Max™ supplemented NI at 150 µCi/ml. Labeling was allowed to proceed for 12 hr, after which the larvae were washed three times with NI and placed into wells of a 48-well plate in 1 ml of Seru-Max™ supplemented NI, 100 larvae/well. The larvae and media of one well from each labeling group was harvested immediately and then every 12 hr through the 96th hr of culture and filtered through a 0.22 µm centrifugal filter (Ultrafree-MC, Millipore, Bedford, Mass.). Forty µl of each sample of filtered media containing labeled ES were diluted with 160 µl of SDS-PAGE sample buffer and evaluated by SDS-PAGE. The larvae were washed twice with 400 µl of Tris buffered saline (50 mM Tris pH 6.8, 150 mM NaCl), recovered in 50 µl of SDS-PAGE sample buffer and heated at 95° C. for 10 min. Labeled proteins were collected after centrifugation at 12,000 g for 5 min and 50,000 cpm of each sample were evaluated by SDS-PAGE.

Figure 7:
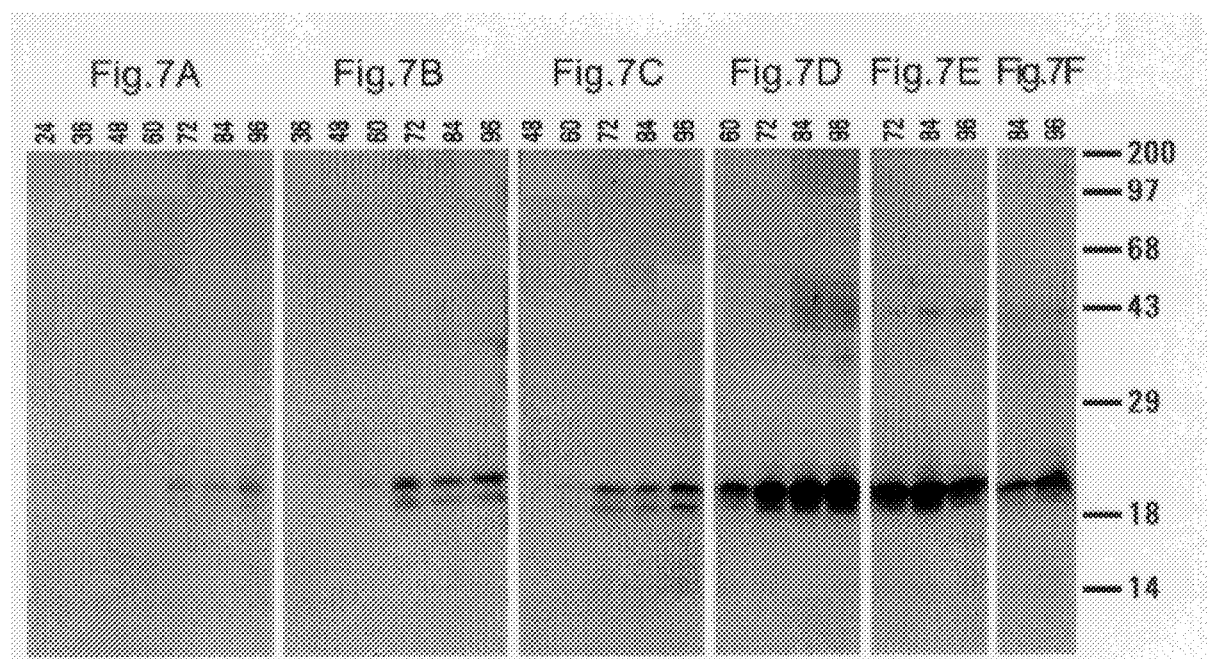
FIG. 7 shows the results of pulse-chase labeling larval excretory-secretory product. Letters at the top indicate groups labeled during the following hours in culture: A, 0–12; B, 12–24; C, 24–36; D, 36–48; E, 48–60; F, 60–72.

FIG. 7 shows the results of pulse-chase labeling of excretory-secretory product. Letters at the top indicate the groups labeled during the following hours in culture: A, 0–12; B, 12–24; C, 24–36; D, 36–48; E, 48–60; F, 60–72. Numbers under the group letters are the last hour of the 12 hr collection periods following the labeling. Molecular weight markers (kD) are as indicated at the right.

Figure 8:
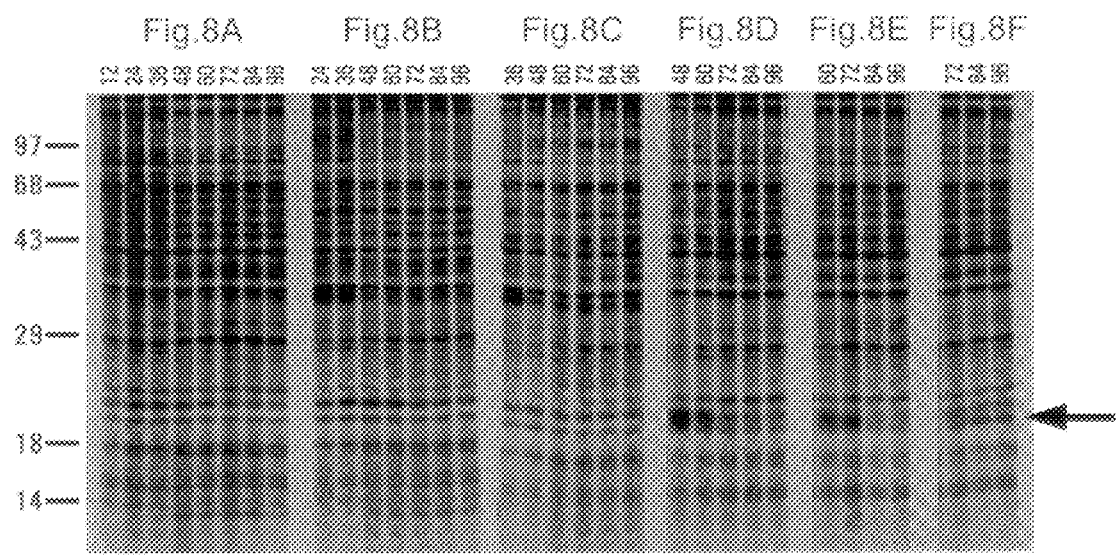
FIGS. 8A–F shows the results of pulse-chase labeling of Dirofilaria immitis larvae.

FIG. 8 shows the results of SDS-PAGE of larvae from each labeling group and harvest time. Letters at the top indicate the groups labeled during the following hours in culture: A, 0–12; B, 12–24; C, 24–36; D, 36–48; E, 48–60; F, 60–72. Numbers under the group letters are the last hour of the 12 hr collection periods following the labeling. Molecular weight markers (kD) are as indicated at the left. The arrow indicates the region where the 22/20.5 kD proteins appear.

Both proteins were seen in the ES in all labeling groups, but not until the 48–60 hr harvest. The proteins were most prominent in the media collected from the larvae labeled from 36–48 hr. Although the resolution of the larval gels was poor, a diffuse appearing band of the appropriate size was seen first in the 36 to 48 hour labeling group and in every group thereafter. This labeling was only evident in two lanes of these groups representing a time of 24 hours.

A radioimmunoprecipitation of ES labeled in the pulse chase experiment described above was performed using the same sera and basic protocol described by Frank and Grieve, 1991 (supra). Two hundred and fifty µl of media (approximately 2.2×10$^4$ cpm total after decay subtraction) collected between 84 and 96 hours from the larvae labeled from 36 to 48 hours in culture (FIG. 7, lane D-96) was mixed with 250 µl of pre-swollen protein A agarose beads and rocked 4 hr at 4° C. One hundred µl of this pre-cleared media was then mixed with 75 µl of protein A agarose pre-incubated for 4 hr at 4° C. with 2.5 µl of either the pooled immune dog sera or the pooled sera from their infected non-immune cohorts. The samples were then treated and evaluated as described.

Figure 9:
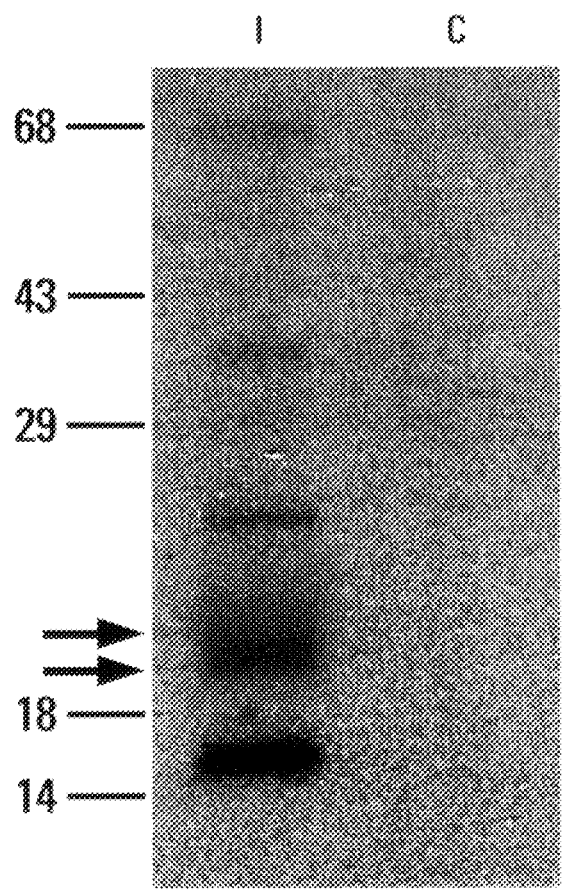
FIG. 9 shows radioimmunoprecipitation of metabolically labeled excretory-secretory product collected from 84 to 96 hours from larvae labeled from 36 to 48 hours.

This sample was chosen for the relative prominence of labeled 20 and 22 kD proteins and the relative lack of other labeled molecules. FIG. 9 shows radioimmunoprecipitation of metabolically labeled excretory-secretory product collected from 84 to 96 hours from larvae labeled from 36 to 48 hours. As seen in FIG. 9, the 22- and 20.5-kD proteins (arrows) are recognized by immune dog sera (I) but not their infected non-immune cohorts (C). A 16 kD protein was also specifically recognized by the immune sera. Molecular weight markers (kD) are as indicated at the left.

Approximately two hundred *Aedes aegypti* mosquitoes were blood fed as usual except that the infected blood meal contained 190 µCi Translabel™ per ml and they were allowed access to blood meal for 3 hours. Infective L3 were harvested on day 11 and placed into wells of a 48 well plate at 100 L3 per well in 1 ml of Seru-Max™ supplemented NI. One well was harvested every 12 hours starting at 0 hr and ending at 72 hr in culture. The larvae and media were processed as described in the pulse-chase labeling section above. Forty µl of media and all of the solubilized larval proteins were evaluated by SDS-PAGE. No labeled proteins were observed in any of the ES samples even after a 25 day exposure of ES gels to film.

Figure 10:
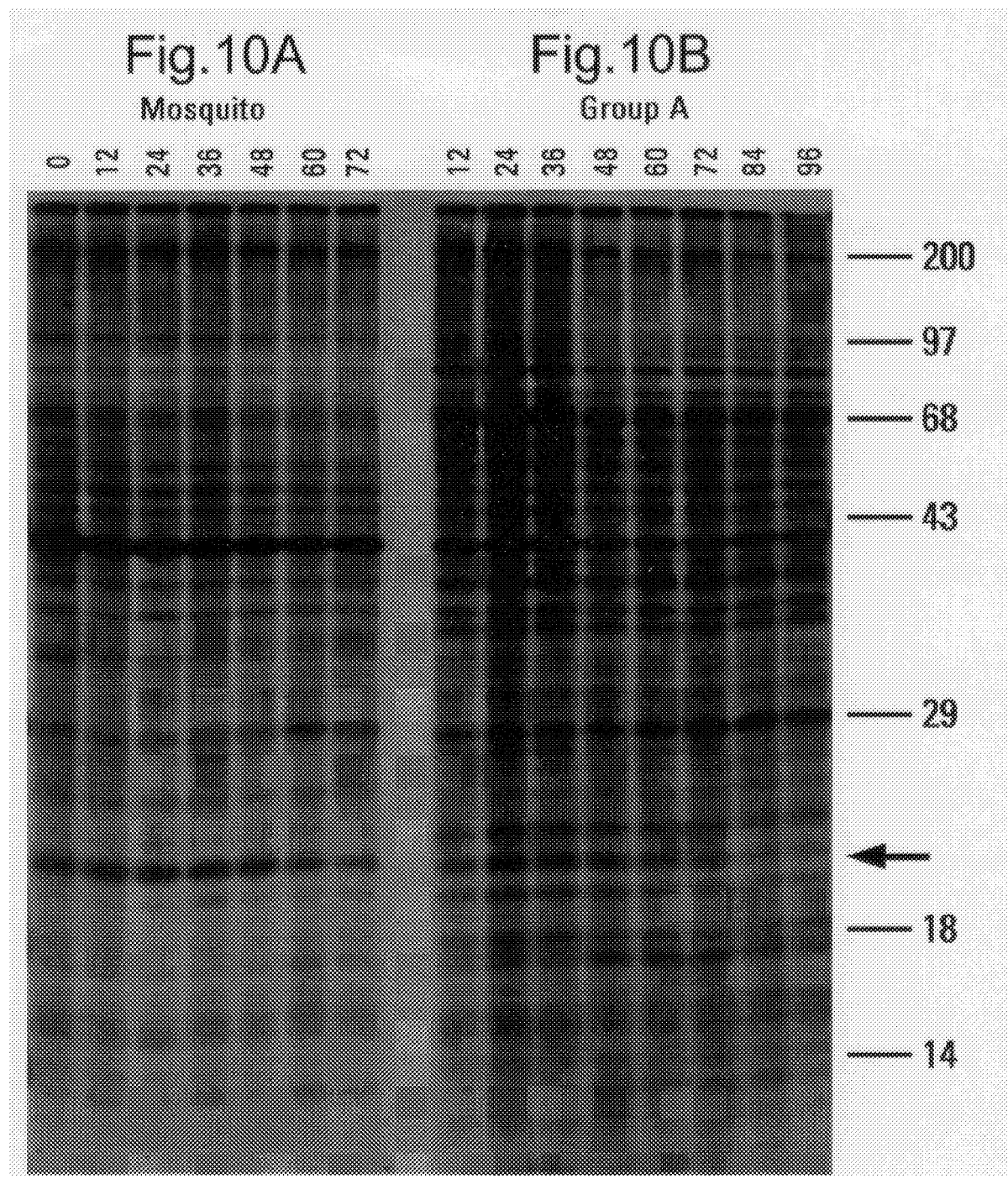
FIG. 10 shows proteins from larvae labeled within the mosquito.

The proteins labeled within the mosquito are shown in FIG. 10. The group labeled Mosquito represents larval proteins labeled with Translabel™ being added to the infected blood meal. The group labeled Group A represents larval proteins labeled from a pulse from 0 to 12 hours in culture, and are the same samples as group A in FIG. 8. Numbers under the group are the last hour of the 12 hr collection periods following removal from the mosquito. Molecular weight markers (kD) are as indicated at the right. The arrow indicates the region where the 22/20.5 kD proteins appeared in FIG. 8. Neither of the molecules were observed in any of the samples.

EXAMPLE 7

Purification, Trypsin Digestion and Partial Amino Acid Sequencing of the 20 and 22 kD Proteins Third stage larvae were collected and cultured in vitro as described (Frank and Grieve (1992) supra). The larvae were washed free of serum proteins at 48 hr, placed back into culture and the serum-free media containing larval ES products was collected from 48 to 144 hr in culture. Each week's yield of ES was collected, filtered through a 0.45 µm filter (Acrodisc™, Gelman Sciences, Ann Arbor, Mich.) and frozen at −70° C. until further processing. Processing was conducted at 4° C. or on ice and consisted of thawing the ES and adding 0.5M EDTA.Na$_2$, pH 8.0, to a final concentration of 5 mM. EDTA was the only protease inhibitor used since only metalloprotease activity has been found in larval ES (Richer et al., *Exp Parasit* (1992) 75:213–222). The ES was concentrated and the buffer was exchanged using Centriprep-10 and Centricon-10 (Amicon, Beverly, Mass.); the final buffer was 20 mM Tris, 1 mM EDTA.Na$_2$, pH 7.2.

All chromatography was performed on a Beckman 338 binary system using System Gold version 3.10 chromatography software (Beckman Instruments, Inc., San Ramon, Calif.). The separations and fraction collections were conducted at room temperature and the fractions placed at 4° C. immediately after each run. When portions of the samples were metabolically labeled, aliquots of the collected fractions were assayed in scintillation fluid by a Beckman Model LS 1801 liquid scintillation counter (Beckman Instruments, Inc.).

Figure 11:
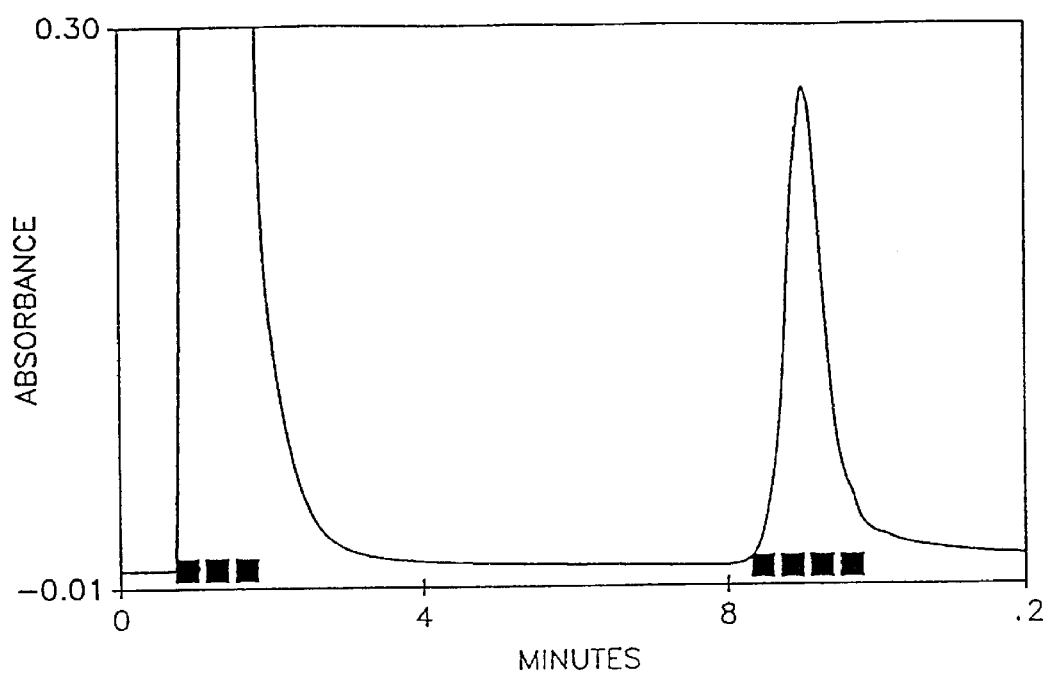
FIG. 11 shows the chromatogram of the first separation of larval ES by cation exchange chromatography.

The first purification was from approximately 38,650 larvae, 3,550 of which had been metabolically labeled with Translabel™ from 48 to 144 hr. The ES products were concentrated to 175 $\mu$l in 20 mM Tris, 1 mM EDTA.Na$_2$, pH 7.2 (Buffer A) and contained 1.3 $\mu$g/$\mu$l protein with an [$^{35}$S] incorporation of 7,450 cpm/$\mu$l. Cation exchange chromatography was used as the first step in purification. A SynChropak CM300-GRD 4.6×50 mm column (Synchrom, Inc., Lafayette, Ind.) was used. The sample was diluted with 300 $\mu$l buffer A, centrifuged at 12,000 g and the supernate injected onto the column at 0.5 ml/min Buffer A. After a 5 min wash, the adsorbed proteins were eluted with a steep gradient to 100% Buffer B (1M KCl in Buffer A) over 0.1 min while 200 $\mu$l fractions were collected throughout. Detection of proteins was at 280 nm. FIG. 11 shows the resultant chromatogram. Boxes are fractions evaluated by SDS-PAGE.

Figure 12:
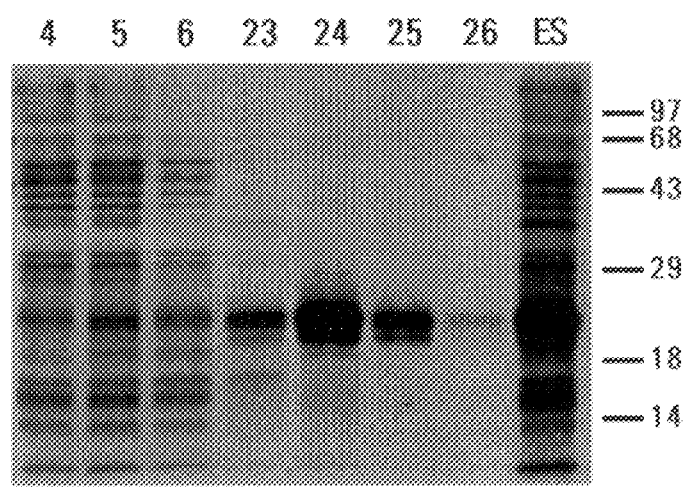
FIG. 12 shows SDS-PAGE of larval ES separated by cation exchange chromatography.

FIG. 12 is an autoradiograph of 2 $\mu$l of fractions 4 through 6 collected from the void peak and fractions 23 through 26 collected from the eluted peak, subjected to SDS-PAGE. The lane labeled ES represents 2 $\mu$l of the starting material. Molecular weights (kD) are as indicated on the right. The vast majority of contaminating proteins are eliminated with this first step. Also of interest was that the 22 kD protein was actually two bands when purer preparations and shorter exposure times were used. The proteins of interest were subsequently designated the 20 kD, the 22L kD (lower band) and the 22U kD (upper band) proteins.

Reverse phase chromatography using a Vydac C$_4$ 0.21×25 cm, 5 $\mu$m particle size column (Vydac 214TP52, The Separations Group, Hesperia, Calif.) was the second step in purification. Buffer C consisted of 0.1% trifluoroacetic acid (TFA), 0.085% triethylamine (TEA) in Milli-Q water produced by processing 18 megaohm water through a Milli-Q Plus water system (Millipore Corp., Bedford Mass.), while Buffer D consisted of 0.085% TFA, 0.085% TEA, 80% CH$_3$CN in Milli-Q water. Detection of proteins was at 220 nm. Fractions 23 and 24 from the cation exchange run were injected onto the column followed by fractions 25 and 26 two min later. The initial flow rate was 0.25 ml/min at 12.5% D, 87.5% C. The flow rate was reduced to 0.17 ml/min at 4 min and a gradient to 62.5% D over 200 min was started at 6 min. Fractions of 0.75 min were collected.

FIG. 13 is the chromatogram of the C$_4$ reverse phase separation of larval ES proteins eluted from the cation exchange column shown in FIG. 11. Areas marked in the upper panel by dotted lines are enlarged in the lower panels. Boxes are fractions evaluated by SDS-PAGE.

FIG. 14 shows the silver stained SDS-PAGE gels and their autoradiographs of 5 $\mu$l of fractions 99 through 107 of the early eluting peaks and fractions 227 through 235 of the late eluting peaks. Panels A and C are silver stained, while B and D are autoradiographs of the same gels. Lanes 1–9 (fractions 99–107) are from the early eluting peaks while lanes 10–18 (fractions 227–235) are from the late eluting peaks. Molecular weights (kD) are as indicated. As seen in FIG. 14, the 20 kD protein appears first and predominates in fractions 99–102. The 22L kD protein predominates in fractions 103–107, although there is significant contamination with the 20 kD protein. The 22U kD protein elutes much later and is seen in fractions 229–235.

Trypsin Digestion

A second purification was done for the purposes of trypsin digestion and the acquisition of internal sequences of the three proteins. The ES products of 63,980 larvae were used. A sub-population of 10,000 had been metabolically labeled with Translabel™ from 48 to 144 hr. The ES products were concentrated to 140 $\mu$l as above and filtered through a 0.45 $\mu$m Ultrafree filter (Millipore), followed by a filter wash of 350 $\mu$l Buffer A. The final volume of 490 $\mu$l contained 0.5 $\mu$g/$\mu$l protein with an [$^{35}$S] incorporation of 5,100 cpm/$\mu$l. Cation exchange HPLC was used to separate the concentrated ES products as described for the first purification. The void peak from this was re-injected in two batches separated by one min and the fractions were collected as before. This re-injection was to collect as much of the three proteins as possible at this first step.

FIG. 15 shows the two chromatograms of the second separation of larval ES by cation exchange chromatography. Approximately 250 $\mu$g were injected and the adsorbed proteins were eluted with a step gradient at 5 min as shown in the top chromatogram. The void peak was collected, reinjected and separated again as shown in the bottom chromatogram.

Fractions 23–25 of the first cation exchange run were injected onto the narrow bore C$_4$ column described for the first purification followed by fractions 23–25 from the second run 3 min later. The flow rate was 0.2 ml/min at 88.9% Buffer E (0.1% TFA in Milli-Q water), 11.1% Buffer F (0.085% TFA, 90% CH$_3$CN in Milli-Q water). A gradient to 72.2% Buffer F over 55 min was initiated at 10 min. Fractions of 1 min (200 $\mu$l) were collected from 3 through 83 min. C$_4$ fractions 35 and 36 representing the early eluting 20 kD and 22L kD proteins, respectively, were injected individually onto a C$_{18}$ reverse phase 0.21×25 cm, 5 $\mu$m particle size column (Vydac 218TP52) to try to separate the two proteins further. The flow rate was 0.2 ml/min at 11.1% Buffer F, 88.9% Buffer E with a gradient to 83.3% Buffer F over 65 min. One minute fractions were collected from 3 through 83 min.

FIG. 16 shows the chromatograms from the three runs. X axes are minutes. Y axes are absorbance units. The eluted proteins from the cation exchange shown in FIG. 15 were separated on a C$_4$ reverse phase column as shown in the upper chromatogram. The inset is an enlargement of the late eluting 22U kD area and also represents fractions 55 and 56 which were subjected to trypsin digestion. The early eluting peaks were separated further on a C$_{18}$ reverse phase column as shown in the bottom two chromatograms. The regions marked by dotted lines were subjected to trypsin digestion.

Larval ES fractions from reverse phase chromatography were dried in a Speedvac® (Savant Instruments, Inc., Farmingdale, N.Y.) and dissolved in 30 $\mu$l 0.1M Tris, 1% SDS, pH 7.5. Five microliters of 0.1M DTT, 0.1M Tris, 1% SDS pH 7.5 were added. The tubes were sparged with argon, heated to 95° C. for 3 min and incubated in the dark at room temperature for 2 hr. The denatured and reduced proteins were alkylated to allow detection of cysteine residues by the addition of 20 $\mu$l of 0.1M 4-vinyl pyridine, 0.1M Tris, 1% SDS pH 7.5. The tubes were sparged with argon and incubated in the dark at room temperature for 1.5 hr. After alkylation, the proteins were precipitated by the addition of 1 ml of 4° C. acetone:acetic acid:triethyl amine:water (85:5:5:5) and incubated at room temperature for 30 min followed by −20° C. for 2 hours. Proteins were pelleted by centrifugation at 12,000 g for 10 min at 4° C. The precipitation procedure was repeated once and the resultant precipitates washed with 1 ml of ethanol at −20° C. The precipitates were resuspended in 100 µl of 50 mM $NH_4HCO_3$, pH 7.8. The alkylated proteins were digested by the addition of 3.62 µl of 0.1 µg/µl Promega sequencing grade trypsin (Promega Corp., Madison, Wis.). The digestion reactions were incubated under argon at 37° C. Another 3.62 µl of trypsin was added at 3.5 hr and the digestion continued overnight. After being digested overnight it was noted that small portions of the pellets of the 20 kD and 22L kD proteins were still visible. Digestion reactions were filtered through a 0.45 µm Ultrafree filter (Millipore) and the filter washed with 110 µl 0.06% TFA, the final volume being 217 µl. Peptides derived from tryptic digests were separated by $C_{18}$ reverse phase chromatography using a 0.21×25 cm, 5 µm particle size column (Vydac 218TP52) by a procedure based on Stone et al., in Matsudaira, P. T. (ed.). A Practical Guide to Protein and Peptide Purification for Microsequencing pp. 31–47 (1989). Buffer G consisted of 0.06% TFA in Milli-Q water and Buffer H consisted of 0.052% TFA, 80% $CH_3CN$ in Milli-Q water. Detection of peptides was at 214 nm. The flow rate was 0.17 ml/min and the column was equilibrated with 2% Buffer H, 98% Buffer G. The peptides were eluted using a complex gradient consisting of 2% H for 5 min, increasing to 37.5% H over 60 min, then increasing to minutes 75% H over 30 minutes and finally increasing to 98% H over 15 min. Thirty sec (85 µl) fractions were collected.

The chromatograms of the digests of all three proteins are shown in FIG. 17. As seen from FIG. 17, the tryptic map of the 22U kD protein is completely different from those of the 20 kD and 22L kD proteins.

Immunoblotting

A third purification was conducted for the purposes of immunoblotting with immune sera to assess the possible immunological relevance of these molecules and to compare to the radioimmunoprecipitation previously described (Frank and Grieve (1992) supra). The ES products of 69,300 larvae were used. The ES products were concentrated to 100 µl and subjected to cation exchange chromatography as described for the second purification of larval ES proteins.

Fractions 22–25 of the first cation exchange run were injected onto the narrow bore $C_4$ column described for the first purification followed by fractions 22–25 from the second run 5 min later. The flow rate was 0.2 ml/min at 11.1% Buffer F, 88.9% Buffer E. The proteins were eluted with a complex gradient differing from the gradient described above. At 10 min a gradient to 33.4% F over 40 min was initiated, then increased to 66.7% F over 30 min and finally increased to 100% F over 5 min. Fractions of 1 min (200 µl) were collected from 30 through 95.3 min (fraction 18 was only 0.3 minutes in an attempt to separate the early peaks).

Figure 18:
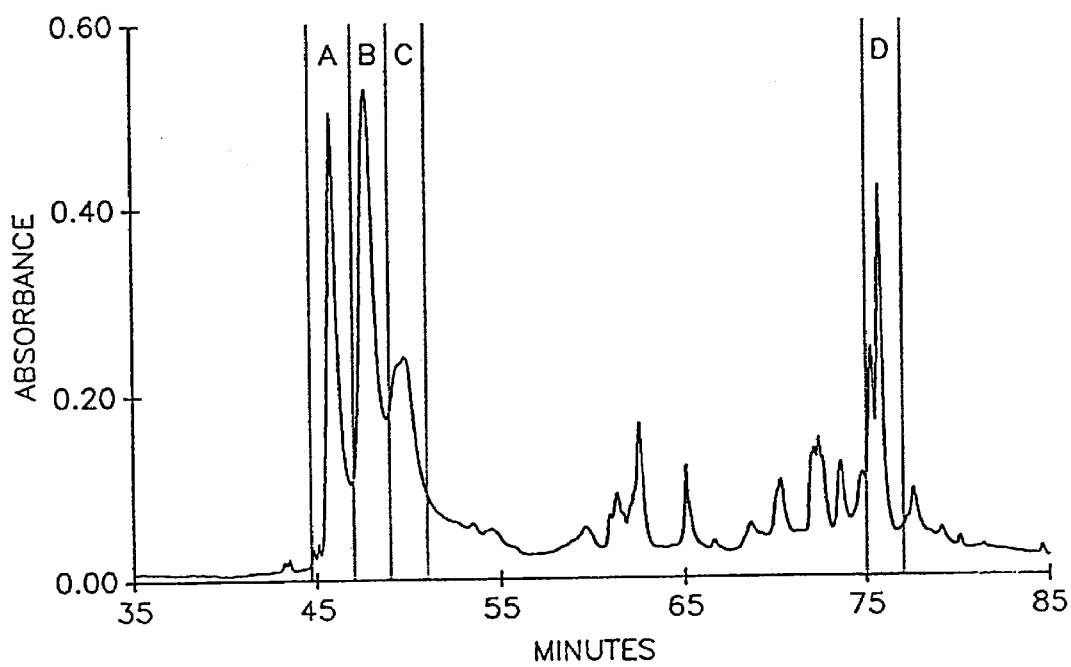
FIG. 18 shows the chromatograms for $C_4$ reverse phase separation of larval ES proteins after cation exchange chromatography.

FIG. 18 shows the chromatogram. The demarcated areas labeled A–D are the fractions that were combined and evaluated by SDS-PAGE. Fractions A–D were dried in a Speedvac® and dissolved in 10.5, 16.4, 9.7 and 7.2 µl of Milli-Q water, respectively. The different volumes were calculated according to peak areas.

FIG. 19 is a Coomassie stained gel of 1 µl each of fractions A–D. Lane A is comprised mostly of the 20 kD protein, lane B demonstrates both the 20 kD and 22L kD proteins and lane C shows an enrichment of the 22L kD protein. Lane D is the 22U kD protein.

Immunoblots of 1 µl per lane of fractions A, C and D were performed. The sera used was the same immune dog sera and infected non-immune dog sera generated from chemically abbreviated infections as described for the radioimmunoprecipitations. In addition, sera from a dog which had been repeatedly infected with D. immitis for over eight years was used. SDS-PAGE was conducted as described by Frank and Grieve (1992), supra. Immunoblotting was conducted essentially as previously described (Grieve, R. B. et al., J Immunol (1992) 148:2511–2515). Serum was diluted to 1/250 in 5% nonfat milk in TBS and incubated with the nitrocellulose overnight at 4° C. Goat anti-dog IgG heavy and light chain conjugated to alkaline phosphatase (Kirkegaard & Perry Laboratories, Gaithersburg, Md.) was diluted to 1/2500 in 5% nonfat milk in TBS and incubated with the nitrocellulose for 2 hr at room temperature. The substrate system, NBT/BCIP, was added and developed according to manufacturer's instructions (GIBCO BRL, Life Technologies, Gaithersburg, Md.).

FIG. 20 shows the results and demonstrates that the 20 kD and 22L kD protein are uniquely recognized by the immune dog serum and not the others. The lanes marked 20, 22L and 22U are the same as lanes A, C and D, respectively, shown in FIG. 19. Sera used were from dogs immune to infection with D. immitis (Immune), their infected non-immune controls (Infected Control) and a repeatedly infected dog (Chronic Infected). Molecular weights (kD) are indicated on the right. The 22U kD protein was only faintly recognized by the immune dog sera, but neither of the others. A high molecular weight contaminant of the 22U kD fraction was recognized by the immune dog serum and to a much lesser extent the infected non-immune control serum. These bands were not evident by Coomassie staining.

Electroblotting for N-Terminal Amino Acid Sequencing

The procedure as used was originally described by Matsudaira, J Bio Chem (1987) 262:10035–10038, and outlined by LeGendre and Matsudaira, "A Practical Guide to Protein and Peptide Purification for Microsequencing", Matsudaira, P. T. (ed.), pp. 49–69 (1989). The proteins (5.5 µl of fraction A and 4.7 µl of fraction C) were separated by SDS-PAGE as described (Frank and Grieve (1992) supra) except that 0.1M DTT was used as the reducing agent in the SDS-PAGE sample buffer instead of 2-ME. Prior to electroblotting the gel was soaked 5 min in transfer buffer (10 mM CAPS, 0.5 mM DTT, 10% methanol, pH 11). The PVDF Protein Sequencing Membrane, 0.2 µm (Bio-Rad Laboratories), was soaked 5 sec in methanol, 5 min in Milli-Q water and 5 min in transfer buffer. Electroblotting was conducted in a Mini Trans-Blot Cell (Bio-Rad laboratories) in 4° C. transfer buffer at 0.5 amps for 10 min. The membrane was subsequently washed 5 min in Milli-Q water and stained 1 min (0.1% Coomassie brilliant blue R250, 40% methanol, 1% acetic acid). Destaining consisted of two 5 min washes in 50% methanol followed by two 5 min washes in Milli-Q water. The membrane was allowed to air dry. Bands representing the 20 kD protein from fraction A and the 22L kD protein from fraction C were cut from the blot and subjected to N-terminal sequencing. The 20 kD protein yielded sequence consistent with a previous attempt not included, while the 22L kD protein was determined to be N-terminally blocked.

Amino Acid Sequencing

The starred peaks in FIG. 17 represent peptides submitted for sequencing. All sequencing was conducted at Macromolecular Resources, Department of Biochemistry, Colorado State University, Fort Collins, Colo. Proteins and peptides recovered by reverse phase chromatography were concentrated to 50 µl or less using a Speedvac® and frozen at −20° C. until sequencing. Proteins attached to PVDF membranes were maintained at −20° C. until sequencing. N-terminal sequencing was accomplished by Edman degradation (Edman, *Ann New York Acad Sci* (1960) 88:602–610, in an ABI Model 473A Protein/Peptide Sequencer System (Applied Biosystems, Inc., Foster City, Calif.) using pulsed liquid chemistry and on line microgradient PTH amino acid analysis (Hewick et. al., *J Bio Chem* (1981) 256:7990–7997; Geisow and Aitken in Findlay, J. B. C. and M. J. Geisow (ed.). Protein Sequencing: A Practical Approach pp. 85–98, 1989). The sequences obtained for each are shown in FIG. 21 (SEQ ID NOS:1 through 20. Samples were obtained by reverse phase HPLC or from electroblots onto PVDF membranes. Either the whole protein was submitted for N-terminal sequence or a tryptic peptide eluting at the indicated time was submitted. The most likely sequence obtained is shown in bold; secondary sequences are shown underneath; [−] indicates no designation. The last peptide shown was obtained from adult female *D. immitis*, all other submissions were from larval ES. There was much similarity in the sequences obtained from the peptides of the 20 kD and 22L kD proteins.

Molecular Weight Determination

Tris-tricine SDS-PAGE was done according to the method of Schagger and von Jagow, *Analyt Biochem* (1987) 166:368–379. This Tris-tricine system has been reported to give more accurate estimates of molecular weights for other proteins (Patton et al., *Analyt Biochem* (1991) 197:25–33). The remaining 10 µl of the combined fractions 19 and 20 (lane B in FIG. 19) from the third purification of the 20 and 22 kD proteins described in Section 3 were dried in a Speedvac®, dissolved in 25 µl tricine sample buffer (4% SDS, 12% glycerol, 50 mM Tris, 2% 2-ME, 0.1% Serva blue G, pH 6.8) and reduced at 40° C. for 30 min. The proteins were separated on a 16.5% resolving gel with a 1 cm 10% spacer gel and a 0.5 cm 4% stacking gel in a Bio-Rad Minigel apparatus (Bio-Rad Laboratories, Richmond, Calif.). Gel dimensions were 7×8×0.075 cm and electrophoresis was performed at 30 V for 20 min, 100 V for 1 hr and 125 V for 45 min. The gel was fixed 30 min (50% methanol, 10% acetic acid), stained 1 hr (0.025 Serva blue G, 10% acetic acid) and destained in 10% acetic acid. Molecular weight standards used were SDS-PAGE Standards, Low Range (Bio-Rad Laboratories) and MW-SDS-17S (Sigma Chemical Co., St. Louis, Mo.).

FIG. 22 shows the resulting Coomassie-stained gel. The 20 and 22L kD proteins resolve as 16.1 and 18.8 kD by reducing Tris-tricine SDS-PAGE. This same sample electrophoresed on 1) a second Tris-tricine gel resulted in molecular weights of 15.3 and 17.7 kD, and 2) a Tris-glycine gel resulted in molecular weights of 21.9 and 23.2 kD (FIG. 19, lane B). Molecular weight standards are shown in the outside lanes and labeled with their respective sizes (kD).

Stage-specific digestions

Twenty-eight adult female *D. immitis* that had been stored at −70° C. were washed 3 times with PBS, comminuted and homogenized with a glass/teflon homogenizer in 40 mM NaCl, 7.5 mM potassium phosphate pH 6.0, 1 mM EDTA, 1 mM PMSF, 2 mM DTT, 80 ug/ml leupeptin, 80 ug/ml pepstatin and 1 mg/ml TAME. The homogenate was sonicated for a total of 1 min using a 418 probe attached to a W-380 sonicator (Heat System-Ultrasonics, Inc., Farmington, N.Y.), centrifuged at 5,000 g for 10 min and the supernate was collected.

Twenty four adult male *D. immitis* that had been stored at −70° C. were washed 3 times with TBS (50 mM Tris, 150 mM NaCl pH 8.0), frozen in liquid nitrogen and ground to a fine powder with a mortar and pestle. This powder was homogenized in 40 mM NaCl, 20 mM Tris pH 7.2, 1 mM EDTA, 1 mM PMSF, 5 ug/ml leupeptin, 5 ug/ml pepstatin and 1 mg/ml TAME. The homogenate was centrifuged at 10,000 g for 20 min and the supernate was collected.

The resultant supernatant materials of both male and female worms were further concentrated and the buffer was exchanged to 20 mM Tris, 1 mM EDTA ph 7.2 using Centriprep-10 and Centricon-10 (Amicon). All steps described were conducted at 4° C. or on ice.

Similar purification procedures as described for larval ES were conducted on both adult male and female somatic soluble extracts to determine if any of the three proteins could be found to disprove stage specificity. A total of 9.4 mg of adult male extract in 1.4 ml was separated in two runs on the same cation exchange column used above employing a 5 min gradient instead of the 0.1 min gradient used for larval ES; 0.5 min (250 µl) fractions were collected. Adult female proteins were subsequently separated by a CM Memsep 1000 membrane cation exchange cartridge (Millipore). Approximately 60 mg of protein in 8 ml were injected in ten 800 µl portions over 10 min. The flow rate was 2 ml/min and the cartridge was washed for 15 min prior to initiating a gradient to 100% Buffer B over 5 min. Fractions were collected at 0.25 min (500 µl) intervals. Fractions from the eluted proteins of adult male and female extracts were evaluated by SDS-PAGE and those containing bands of the appropriate molecular weight were subjected to separation by $C_4$ reverse phase chromatography.

Four fractions from the adult male cation exchange elution were injected onto a $C_4$ reverse phase 0.46×15 cm, 10 µm particle size column (Vydac 214TP10415) at one minute intervals, and in a second run three fractions from the adult female cation exchange elution were likewise injected onto the column. The initial conditions were a flow rate of 0.8 ml/min at 11.1% Buffer F, 88.9% Buffer E. A gradient to 44.4% F over 30 min was started at 5 min, followed by an increase to 66.7% F over 40 min and finally an increase to 100% F over 5 min. Fractions were collected at 0.5 min (400 µl) intervals. FIG. 23 shows the resulting chromatograms. The demarcated areas indicate regions where individual fractions were evaluated by SDS-PAGE and where fractions were combined and subjected to trypsin digestion. A protein consistent with the 22U kD protein was found in this region and was the only protein stained with Coomassie brilliant blue, while some very minor contaminants were seen upon subsequent silver staining (not shown). The 20 kD and 22L kD proteins would elute between approximately 19.8 and 22.8 min and were not seen. The combined fractions were dried in a Speedvac® and dissolved in 100 µl of 0.1M Tris, pH 7.5. The adult male 22U kD protein had a protein concentration of 1.6 µg/µl (159 µg total) while the adult female 22U kD protein was 1.1 µg/µl (111 µg total).

Trypsin digestions were conducted on 20 µg of the adult male and 15 µg of the adult female 22U kD proteins as described for the larval ES proteins except for slight variations in volumes and time. The proteins were dissolved in 50 µl 0.1M Tris, 1% SDS, pH 7.5. Ten microliters of 0.1M DTT, 0.1M Tris, 1% SDS, pH 7.5 was added, the tubes sparged with argon, heated to 95° C. for 3 min and incubated in the dark at room temperature for 2 hr. The denatured and reduced proteins were alkylated by the addition of 40 µl of 0.1M 4-vinyl pyridine, 0.1M Tris, 1% SDS, pH 7.5. The tubes were sparged with argon and incubated in the dark at room temperature for 2 hr. After alkylation, the proteins were precipitated by the same procedure as described for the larval ES digests. The proteins were dissolved in 25 µl TFA, dried in a Speedvac®, dissolved in 25 µl of 50 mM NH$_4$HCO$_3$, pH 7.8 and dried again. These extra steps were used to fully dissolve the precipitated proteins and subsequently remove all traces of TFA. The alkylated proteins were dissolved in 100 µl of 50 mM NH$_4$HCO$_3$ pH 7.8 and digested by the addition of 7.25 µl of 0.1 µg/µl Promega sequencing grade trypsin (Promega Corp.). The digestion reactions were incubated under argon for 18 hours at 37° C. The peptides were separated under the same conditions as the digest of the larval ES 22U kD protein described above. FIG. 24 shows the trypsin maps of the 22U kD proteins from larval ES, adult female and adult male sources. The maps were virtually identical. The starred peaks of the larval ES and adult female chromatograms were submitted for N-terminal sequencing and determined to be the same (FIG. 21). It appears the 22U kD protein is also found in adult *D. immitis*, while there is no clear evidence to suggest the presence of either the 20 kD protein or the 22L kD protein in adult somatic soluble preparations.

EXAMPLE 8

Molecular Cloning of the 22/20.5 kD Protein Isolated From Larval *Dirofilaria Immitis*

Oligomeric DNA primers and probes were made by DNA Express, Department of Biochemistry, Colorado State University. Synthesis was done using an ABI model 392 DNA/RNA synthesizer using cyano-ethyl-phosphoramidite chemistry. Products were purified using low pressure reverse phase chromatography.

Probes were 3'-end labeled by tailing with [$^{32}$P]-deoxycytidine (Collins and Hunsaker, *Analyt Biochem* (1985) 151:211–224, 1985). Terminal deoxynucleotidyl transferase (Promega Corp., Madison, Wis.) was used according to manufacturers instructions. Reactions were in 50 µl and consisted of 10 µl 5× reaction buffer (Promega), 5 µl 1 µM probe, 4 µl [α-$^{32}$P]dCTP (800 Ci/mmole, 10 mCi/ml, Du Pont NEN®, Boston, Mass.) and 25 U terminal transferase. Reactions were incubated 1 hr at 37° C. followed by 10 min at 70° C. Labeled probe was precipitated by the addition of 20 µg glycogen, 120 µl 10M ammonium acetate, 129.5 µl water, 750 µl ice cold ethanol and incubating on ice 30 min followed by centrifugation at 12,000 g for 20 min. The pellet was washed with 750 µl ice cold 80% ethanol, centrifuged again, the supernatant solution was removed and the pellet was air dried. Labeled probes were dissolved in 1 ml hybridization solution and 2 µl counted in scintillation fluid with a Beckman model LS 1801 liquid scintillation counter (Beckman Instruments, Inc., Irvine, Calif.).

A 48 hour L3 cDNA library constructed from poly A+ selected RNA using the ZAP-cDNA® Synthesis Kit (Stratagene, La Jolla, Calif.) and the Uni-ZAP XR vector (Stratagene) was screened. The final library contained 4.88·10$^6$ plaque forming units (pfu)/µl with 96.4% recombinants. Library plating and plaque lifts were essentially done according to manufacturer's instructions (Stratagene) using XL1-Blue *Escherichia coli*. Nytran 0.45 µm 137 mm membranes (Schleicher and Schuell, Keene, N.H.) pre-soaked in 2×SSC (1×=150 mM NaCl, 15 mM sodium citrate, pH 7.0) were used for plaque lifts. Duplicate lifts were done; the first for 2 min and the second for 4 min. Membranes were soaked 2 min in denaturant (1.5M NaCl, 0.5M NaOH), 5 min in neutralizer (1.5M NaCl, 0.5M Tris, pH 8.0), 30 sec in 0.2M Tris pH 7.5, 2×SSC and briefly blotted dry. The DNA was crosslinked to the membranes using a Stratalinker® UV Crosslinker (Stratagene). All membranes were soaked 4 hr at 37° C. in 50 ml prehybridization solution consisting of 5×SSPE (1×=150 mM NaCl, 10 mM NaH$_2$PO$_4$.H$_2$O, 1 mM EDTA.Na$_2$, pH 7.4), 10×Denhardt's reagent (1×=0.02% Ficoll 400, 0.02% polyvinylpyrrolidone, 0.02% bovine serum albumin fraction V), 1% sarkosyl, 0.1 mg/ml denatured salmon sperm DNA and 1000 pmoles pd(C)$_{10}$ oligodeoxycytidylic acid (Pharmacia LKB Biotechnology, Piscataway, N.J.). Membranes were rinsed briefly in Milli-Q water and hybridized for 18 hr at 37° C. in 50 ml of 5×SSPE, 1% sarkosyl, 1000 pmoles pd(C)$_{10}$ and 5 pmoles labeled GRF6 probe (approximately 1.5×10$^6$ cpm/ml). This probe was synthesized based on the amino acid sequence EACYDQ obtained from the 32 and 35 min tryptic peptides of the 20 and 22L kD proteins, respectively, described and shown in FIG. 21. The DNA sequence of GRF6 was 5'GAA GCI TGC TAT GAT CAA 3', where I is inosine which is capable of base pairing with all four bases. The wobble base selection for glutamic acid (E), cysteine (C), tyrosine (Y), aspartic acid (D) and glutamine (Q) was based on codon usage for two *D. immitis* proteins previously reported (GenBank accession numbers M29733 and M82811). Washes were 3 min each in 500 ml. Membranes were washed three times in 5×SSPE, 1% sarkosyl at room temperature followed by one wash each in 1×SSPE, 0.1% SDS at room temperature, 37° C., 42° C. and 45° C. Membranes were exposed to film after the 37° C., 42° C. and 45° C. wash. X-OMAT AR film (Eastman Kodak Co., Rochester, N.Y.) and Lightning Plus intensifying screens (Du Pont, Wilmington, Del.) were used, and exposure was at −70° C. for 14–18 hr.

Of the 102,000 plaques screened, approximately 252 (0.25%) hybridized to the probe. Sixteen plugs containing positive plaques were removed and 5 of these were plaque purified. Positive plaques to be purified were cored from the plate and placed in 1 ml SM buffer (100 mM NaCl, 8 mM MgSO$_4$.7H$_2$O, 50 mM Tris pH 7.5, 0.01% gelatin) with 2–3 drops of chloroform, vortexed and incubated at room temperature 1 hr. Subsequent rounds of plaque lifts, hybridization, washes and exposure to film were conducted as described above, except only room temperature and 43° C. final washes (1×SSPE, 0.1% SDS) were used. A total of 3 rounds of purification were performed using 10 µl of either 1:100 or 1:200 dilutions of the picked plaques.

Plasmids pBluescript SK(−) with the cloned inserts were excised and recircularized from the positive Uni-ZAP XR vectors which were plaque purified using the procedure described in the manufacturer's instructions (Statagene). One colony from each positive clone was selected and subjected to plasmid preparation.

Plasmid minipreparations were based on the alkaline lysis method described by Birnboim and Doly, *Nuc Acids Res* (1979) 7:1513–1523, and Ish-Horowicz and Burke, *Nuc Acids Res* (1981) 9:2989–2998, and modified by Sambrook, Fritsch and Maniatis, Molecular Cloning: A Laboratory Manual (2nd ed. 1989). The final pellet was dissolved in 32 µl TE and the OD$_{260}$ determined to quantitate the DNA recovery.

Insert sizes were determined by digestion of plasmids with the restriction endonucleases EcoRI (New England BioLabs, Beverly, Mass.) and XhoI (Stratagene). Digestions were conducted in 10 µl 1× Stratagene #7 digestion buffer containing 6.7 units each enzyme, 0.5 µl plasmid DNA and incubated 30 min at 37° C. The digests were electrophoresed in a 1% Nusieve GTG (FMC Bioproducts, Rockland, Me.), 1% Seakem LE (FMC Bioproducts), 0.5×TBE (1×=90 mM Tris, 90 mM boric acid, 2 mM EDTA), 0.5 µg/ml ethidium bromide gel at 7.5 V/cm. DNA was visualized with ultraviolet irradiation at 300 nm. Insert sizes of the five were determined by first order regression. The insert sizes were estimated to be 334 bp (clone 1), 442 bp (clone 2), 603 bp (clone 3), 589 bp (clone 4) and 442 bp (clone 5), 32 bp of which were vector sequence.

DNA Sequencing of Clones

DNA sequencing was done by the dideoxy chain termination method described by Sanger, Nicklen and Coulson, *Proc Nat Acad Sci USA* (1977) 74:5463–5467, using the Sequenase® version 2.0 DNA Sequencing Kit (United States Biochemical, Cleveland, Ohio) and the manufacturer's instructions. Plasmid DNA (5 µg) was used as the template. Primers for sequencing consisted of the upstream SK primer (5' CGC TCT AGA ACT AGT GGA TC 3') (SEQ ID NO:24) and the downstream T7 primer (5'AAT ACG ACT CAC TAT AG 3') (SEQ ID NO:25) which hybridized to the vector 27 bp and 48 bp from the actual insert sequence, respectively. Other primers used were the sense oligomer GRF6 used for screening the library (274–291 bp of clone 4) and the antisense oligomer GRF13 (5' TAT GCA CCA CGA TTG TGG 3') (SEQ ID NO:26) synthesized after sequencing the entire clone 4 sense strand so as to complete the second strand sequence. A model S2 sequencing gel electrophoresis apparatus (Gibco BRL, Gaithersburg, Md.) was used with wedged spacers (0.4 to 1.2 mm) and a sharktooth comb. Gels were 6% acrylamide, 0.3% bis-acrylamide, 8M urea, 1×TBE, and they were polymerized with 0.1% ammonium persulfate and 0.1% TEMED. Pre-electrophoresis at 65 watts was conducted for 30 min prior to loading the samples. Samples (4.5 µl) were loaded and electrophoresed at 65 watts. Gels were fixed 1 hr in 5% methanol, 5% acetic acid, lifted from the glass plate with Whatman 3 MM Chr paper (Whatman, Maidstone, England), covered with plastic wrap and dried under vacuum at 80° C. for 1 hr. Gels were exposed to X-OMAT AR film (Kodak) at −70° C.

Figure 25:
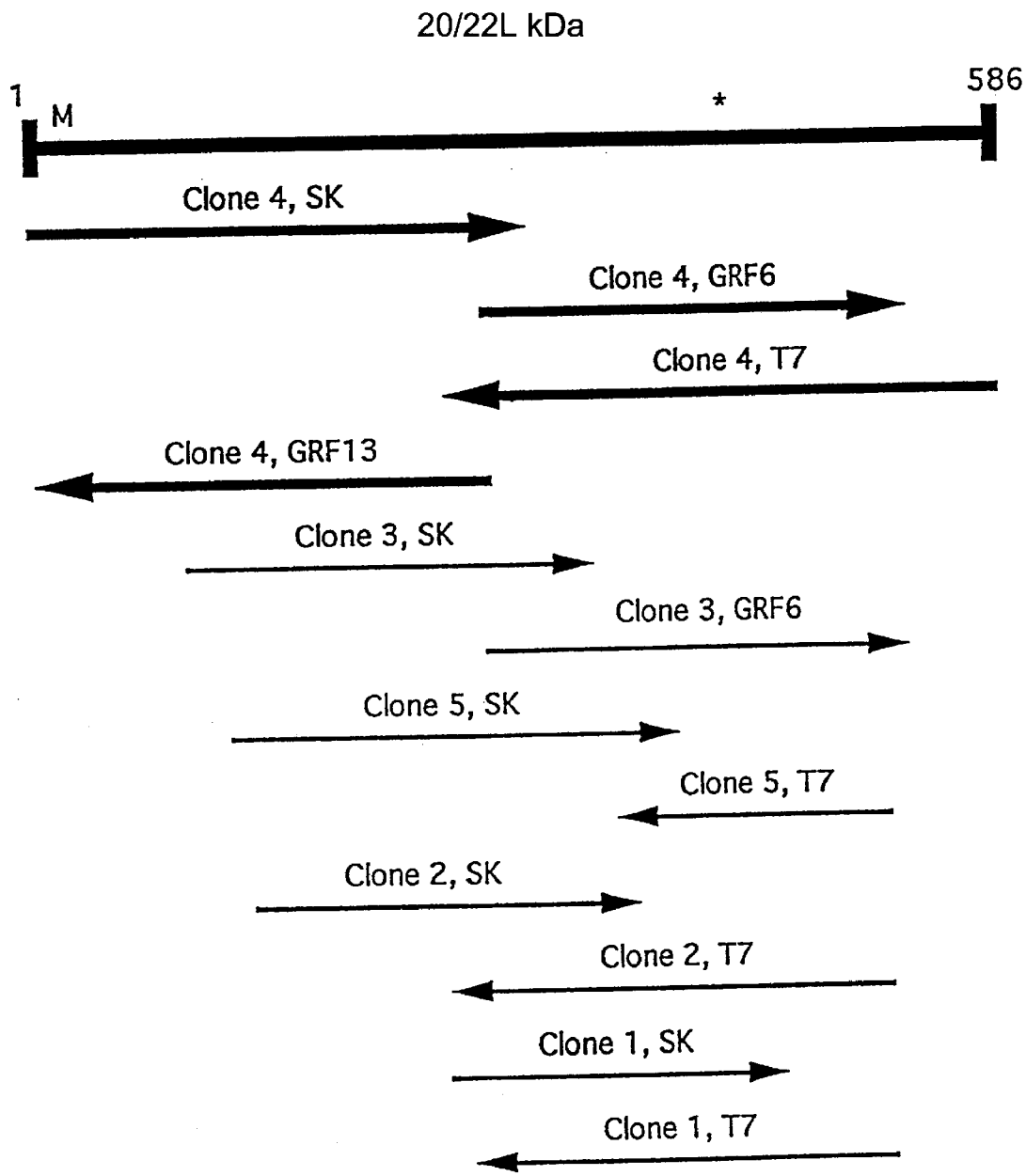
FIG. 25 displays the strategy used for the sequencing of cDNA clones of the 20/22L kD proteins.

Partial DNA sequence was determined for clones 1, 2, 3 and 5 and the full double strand sequence of the protein coding region was determined for clone 4. FIG. 25 shows the sequencing strategy used for the sequencing of cDNA clones of the 20/22L kD proteins. The 586 bp insert of clone 4 with the position of the first methionine (M) and stop codon (*) is shown on top. The direction of sequencing, the clone sequenced and the primer used are shown underneath. The full double strand sequencing strategy of the coding region of clone 4 is shown by the large arrows. All five clones were comprised of the same DNA sequences terminating at varying regions at the 5' end of the coding strand, with the exception that clone 2, base 24 was A while all others were G (base 173 of clone 4). This difference coded for a histidine instead of an arginine found in the other clones.

FIG. 26 (SEQ ID NO:21 and SEQ ID NO:22) shows the entire sequence of clone 4 with the deduced amino acid sequence. The start methionine and termination codon are in bold. The position of the base substitution coding for a histidine in clone 2 is shown in parentheses below the sequence. Regions corresponding to synthetic oligomeric DNA probes/primers and their direction are underlined (>=sense; <=antisense). Amino acids are in single letter code. *=termination codon.

Northern Blotting

RNA was purified based on the method of Chomczynski and Sacci, *Analyt Biochem* (1987) 162:156–159. Larval RNA was extracted from 6,100 L3 directly from mosquitoes (0 hr L3), 18,400 48 hr L3 and 6,800 6 day L4. Larvae were harvested and cultured in NI with 20% Seru-Max™ as described (Frank and Grieve (1992) supra) except that 0 hr L3 were collected into room temperature NI without serum proteins. Larvae were settled by gravity either at room temperature (0 hr L3) or 37° C. (48 hr L3, 6 day L4), the media removed to 50 µl (0 hr L3, 6 day L4) or to 100 µl (48 hr L3) and 0.5 ml (0 hr L3, 6 day L4) or 1 ml (48 hr L3) 37° C. GT/2-ME (4M guanidinium thiocyanate, 25 mM sodium citrate pH 7.0, 1.5% sarkosyl, 0.5M 2-ME) was added. The larvae were vortexed 1 min, snap frozen in liquid nitrogen and stored at −70° C. The larvae were thawed at 37° C. and vortexed 1 min. To the disrupted larvae 0.1 volume 2M sodium acetate, pH 4.0, was added and mixed, 1 volume water saturated phenol added and mixed followed by 0.2 volume chloroform:isopentyl alcohol (49:1) and vigorous shaking for 20 sec. The mixture was incubated on ice for 15 min, centrifuged at 10,000 g for 20 min at 4° C., and the upper aqueous phase was removed to a separate tube. RNA was precipitated by the addition of an equal volume of ice cold isopropanol, incubating at −20° C. for 1 hr and centrifugation at 10,000 g (48 hr L3) or 12,000 g (0 hr L3, 6 day L4) for 30 min at 40° C. RNA was dissolved in 500 µl GT/2-ME, transferred to a new 1.5 ml tube and precipitated as described above with 500 µl isopropanol and 12,000 g centrifugation. The pellet was washed with 500 µl −20° C. 70% ethanol, centrifuged at 12,000 g for 10 min at 4° C. and air dried. The RNA was dissolved in 0.5% SDS (0 hr L3, 6 day L4) or water (48 hr L4) and quantitated by $OD_{260}$ UV spectroscopy.

Adult female RNA was prepared similarly after the worms were ground to a fine powder in liquid nitrogen. Poly A+ RNA was purified from the total RNA with oligo(dT) cellulose using the RiboSep Mini mRNA Isolation Kit (Collaborative Research, Inc., Bedford, Mass.) and quantitated by $OD_{260}$ UV spectroscopy.

RNA was electrophoresed through formaldehyde gels and transferred to Nytran membranes (Schleicher and Schuell) essentially as described (Sambrook, Fritsch and Maniatis, Molecular cloning: A Laboratory Manual, 2nd ed. 1989) with minor modifications (Fourney et al., *Focus* (1988) 10(1):5–6). Gels were composed of 1.2% Seakem GTG agarose (FMC Bioproducts), 1×MOPS buffer (20 mM MOPS, 5 mM sodium citrate, 1 mM EDTA, pH 7.0), 0.66M formaldehyde. RNA was diluted to 4.5 µl with water and 20 µl sample denaturing buffer was added (50% formamide, 2M formaldehyde, 1×MOPS buffer, 6.7% glycerol, 0.05% bromphenol blue). Samples were heated at 65° C. for 10 min, quenched in ice water and 1 µl of a 1 mg/ml ethidium bromide solution was added. Ten micrograms of larval RNA and 1.8 µg adult female poly A+ RNA were loaded onto the gel and electrophoresed at 3 V/cm for 5.5 hr. An RNA ladder from 0.16 to 1.77 kilobases (Gibco BRL) was used as a size standard. RNA was visualized by UV irradiation at 300 nm and photographed.

RNA was partially hydrolyzed by soaking in 500 ml 1×SSC, 50 mM NaOH 15 min. The gel was then washed twice in 300 ml 10×SSC for 20 min each. Capillary transfer to Nytran membranes (Schleicher and Schuell) was performed with 1×SSC for 13 hr. The membrane was rinsed for 1 min in 2×SSC, excess moisture was removed and the RNA crosslinked to the membrane using a Stratalinker® UV Crosslinker. An initial hybridization procedure resulted in excessive non-specific binding of probe which had to be stripped by boiling the membrane for 20 min in 10 mM Tris, 10 mM EDTA, 0.5% SDS, pH 8.5. The membrane was then exposed to X-OMAT AR film (Eastman Kodak Co.) and Lightning Plus intensifying screens (Du Pont) at −70° C. for 12 hours. Following this, pre-hybridization was conducted for 4 hr at room temperature in 0.2 ml/cm² 5×SSPE, 1% sarkosyl, 9.5×Denhardt's, 0.1 mg/ml denatured salmon sperm DNA, 500 pmoles pd(C)$_{10}$, 50% formamide. The membrane was washed briefly 5 times with Milli-Q water and then hybridized 52 hr in 0.2 ml/cm² 5×SSPE, 1% sarkosyl, 500 pmoles pd(C)$_{10}$, 50% formamide, 5×10⁵ cpm/ml labeled GRF10. GRF 10 was an anti-sense oligomeric DNA corresponding to bases 21–43 of clone 4. The membrane was washed three times at 42° C. in 300 ml 5×SSPE, 1% sarkosyl for 1, 2 and 3 min. The final wash was conducted at 60° C. in 300 ml 1×SSPE, 0.1% SDS for 3 min. The membrane was then exposed to X-OMAT AR film (Eastman Kodak Co.) and Lightning Plus intensifying screens (Du Pont) for 47 hr at −70° C.

A strong signal was seen in the 48 hr L3 lane and a weaker signal was seen in the 6 day L4 lane. FIG. 27 shows the Northern blot analysis of transcripts of the 20/22L kD protein. Total RNA of 0 hr L3, 48 hr L3, 6 day L4 and poly A+ RNA from adult females (Ad F) were probed with GRF 10, an antisense DNA probe corresponding to bases 21–43 of clone 4 (A). The arrow indicates an approximately 720–730 base transcript seen in 48 hr L3 and 6 day L4. RNA size standards were located as shown on the right. Residual signal from a prior hybridization is shown in panel B, and indicates no prior hybridization in the 700 base region. No hybridization was seen to 0 hr L3 or adult female RNA.

Although only 1.8 μg of RNA was loaded in the adult female lane, presumably this contained considerably more message than the 10 μg of larval total RNA per lane due to the poly A+ selection. The finding of a relative abundance of message in 48 hr L3, less in 6 day L4 and none in 0 hr L3, adults and, presumably, microfilariae, substantiates the pulse-chase metabolic labeling patterns described (Frank and Grieve, *J Parasit* (1992) 77:950–956) and the apparent lack of these molecules while purifying the 22U kD protein from adults.

Sequence analysis

MacVector™ version 3.5 sequence analysis software (International Biotechnologies, Inc., New Haven, Conn.) was used for amino acid translations, protein molecular weight and isoelectric point calculations, and hydrophilicity calculations.

Figure 28:
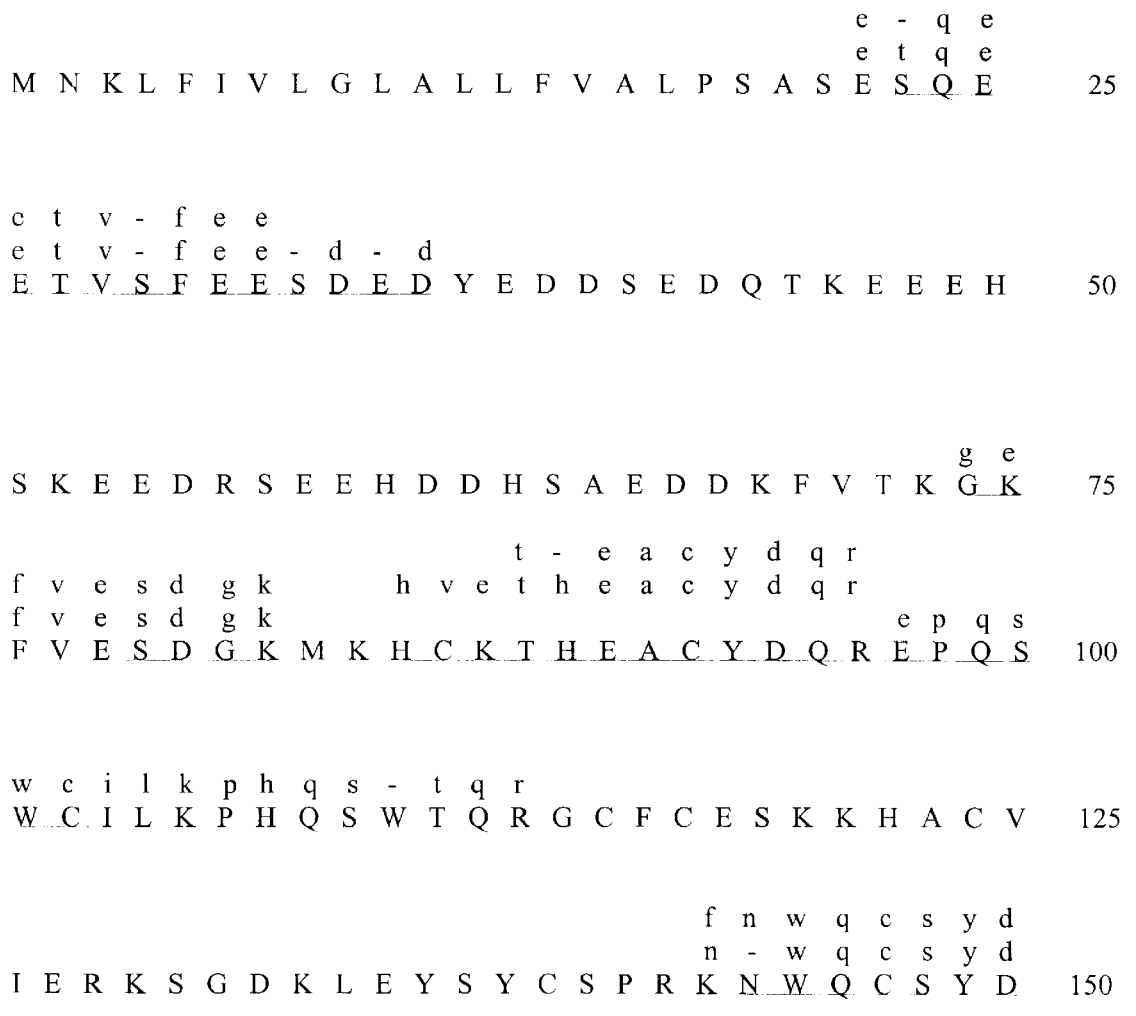

FIG. 28 (SEQ ID NO:23) is the amino acid sequence starting with the methionine coded by bases 7–9 and ending with the aspartic acid coded by bases 454–456 of clone 4. The sequence is shown in single letter code (upper case). Regions corresponding to amino acid sequences determined from peptides are underlined, and the sequences obtained (lower case) are above. The N-terminal sequence obtained for the 20 kD protein is shown in bold.

FIG. 29 shows a hydrophilicity plot of the proposed amino acid sequence. Hydrophilicity (A) was calculated for the entire sequence of FIG. 28 based on the method of Kyte and Doolittle, *J Mol Biol* (1982) 157:105–132, with a window size of 7 amino acids. Molecular weights, isoelectric points (pI) and amino acid compositions of the entire sequence (B, 22L kD) and the proposed cleavage product beginning at the glutamic acid at position 22 (C, 20 kD) are shown.

The encoded protein is very hydrophilic with the exception of the N-terminus. The N-terminus of the 20 kD protein is encoded starting at amino acid 22. The 20 and 22L kD protein differ only by a 21 amino acid hydrophobic leader sequence that is cleaved. The calculated molecular weight of this 21 amino acid segment is 2.2 kD. This explains both the similar chromatographic behavior and the similar immunological reactivity of the two molecules. The calculated molecular weight and pI of the entire proposed protein are 17,527.7 and 4.58, respectively, while those for the cleavage product would be 15,328.1 and 4.52, respectively (FIG. 29). These figures are rather far from the 22 and 20 kD calculated from routine Tris-glycine SDS-PAGE under reducing conditions. These molecular weights are in the range calculated from Tris-tricine SDS-PAGE. The amino acid compositions of the two proteins are also shown in FIG. 29.

The calculated isoelectric points were 4.52 and 4.58 for the 15.3 and 17.5 kD (20 and 22L kD) proteins, respectively. Original estimates for the 20 and 22 kD proteins (Frank and Grieve (1992) supra) were that the 20 kD protein was acidic while the 22 kD protein was basic. This was prior to determining the presence of two proteins in the 22 kD region. It appeared that the prominently labeled basic protein was the 22U kD protein that was not cloned, and that both the 22L and 20 kD proteins were in the more acidic smear.

EXAMPLE 12

Immunization of Dogs

Recombinant or native larval peptides are used to immunize dogs for the purpose of obtaining specifically reactive blood components. Recombinant antigens are administered to dogs with or without adjuvant by the subcutaneous, intramuscular, intradermal or intravenous routes. Following single or multiple immunization, blood is collected from dogs by routine venipuncture. Serum is collected from coagulated blood and used directly or stored frozen prior to use. Leukocytes are collected from anticoagulant-treated blood by density gradient centrifugation and used directly or stored by freezing at 1° C./minute with storage in liquid nitrogen.

What is claimed is:

1. An isolated protein isolatable from the L3 or L4 larval stage of D. immitis, said protein having amino acid sequence ESQEETVSF EESDEDYEDD SEDQTKEEEH SKEEDRSEEH DDHSAEDDKF VTKGKFVESD GKMKHCKTHE ACYDQREPQS WCILKPHQSW TQRGCFCESK KHACVIERKS GDKLEYSYCS PRKNWQCSYD (SEQ ID NO:27).

* * * * *

UNITED STATES PATENT AND TRADEMARK OFFICE
CERTIFICATE OF CORRECTION

PATENT NO. : 5,804,200
DATED : September 8, 1998
INVENTOR(S) : Grieve et al.

Figure 5B:
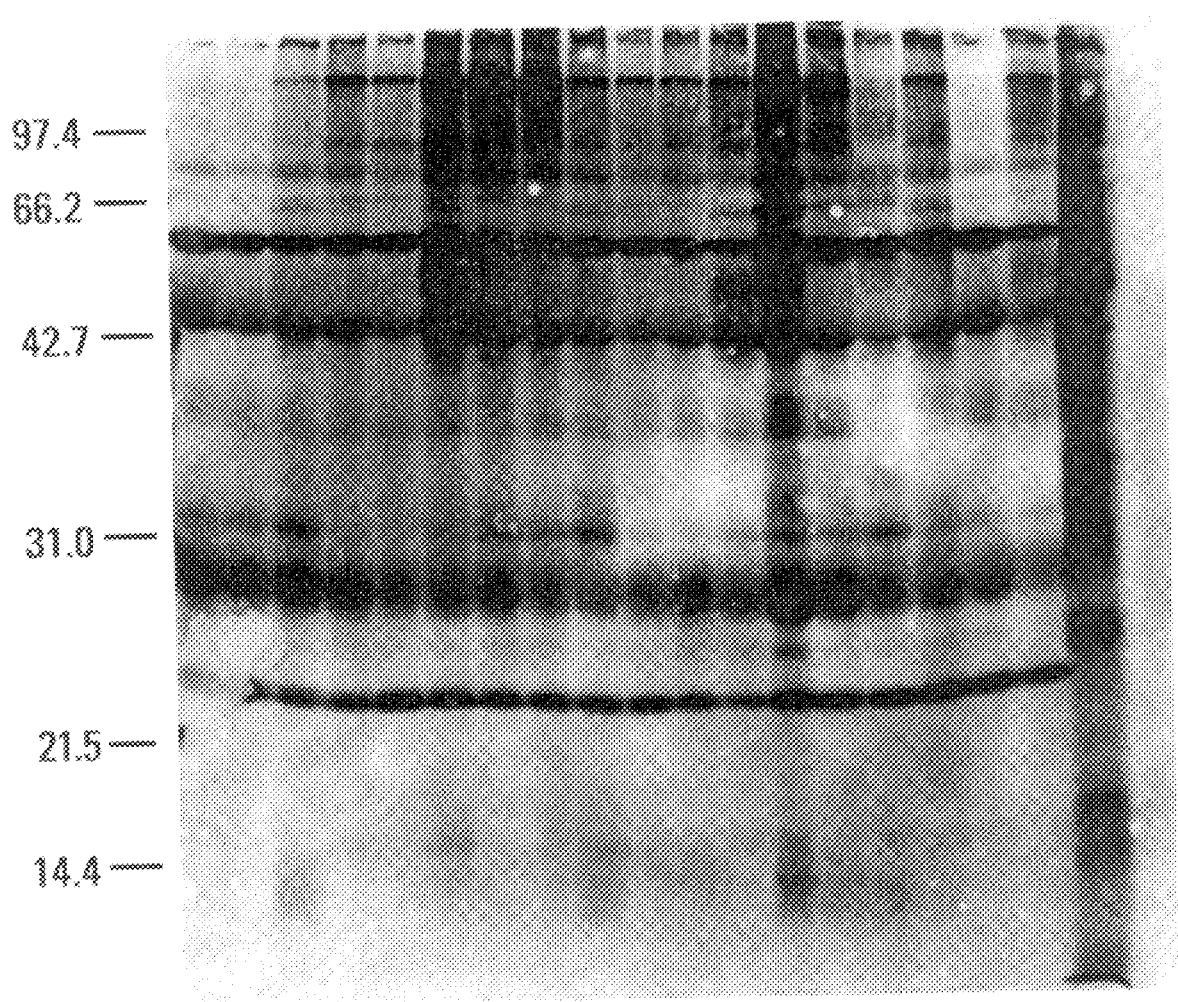
Figure 13A:
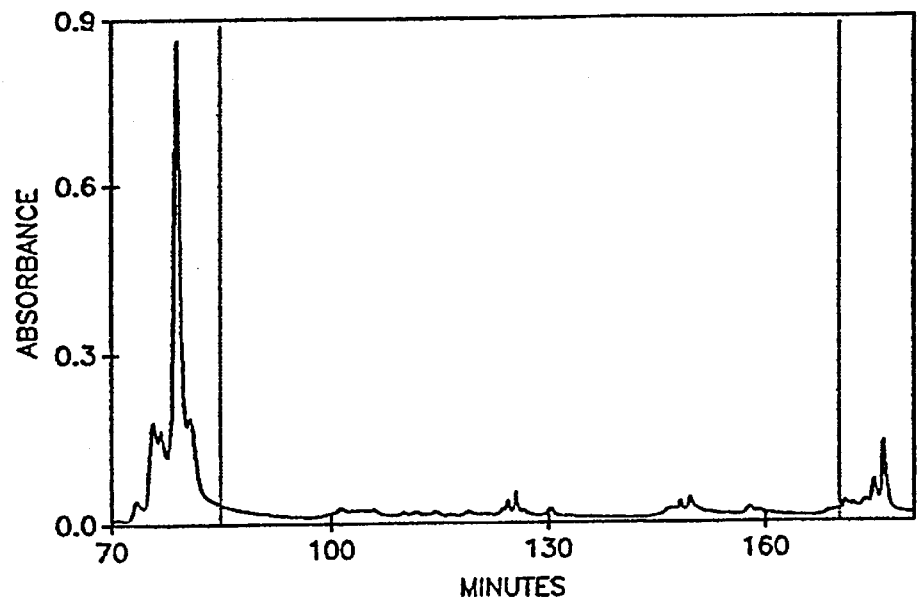
FIG. 13 shows the results of $C_4$ reverse phase separation of larval ES proteins eluted from the cation exchange column shown in FIG. 11.
Figure 13B:
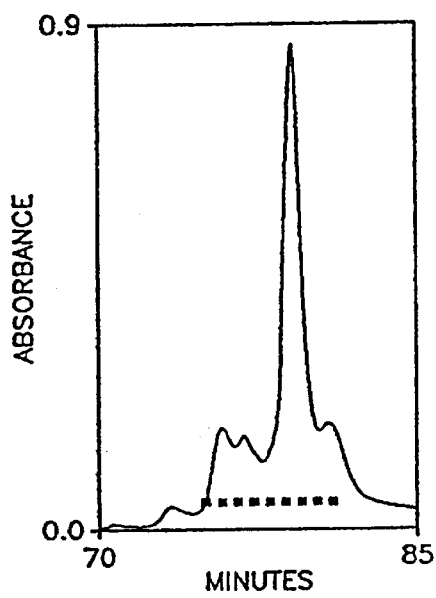
Figure 13C:
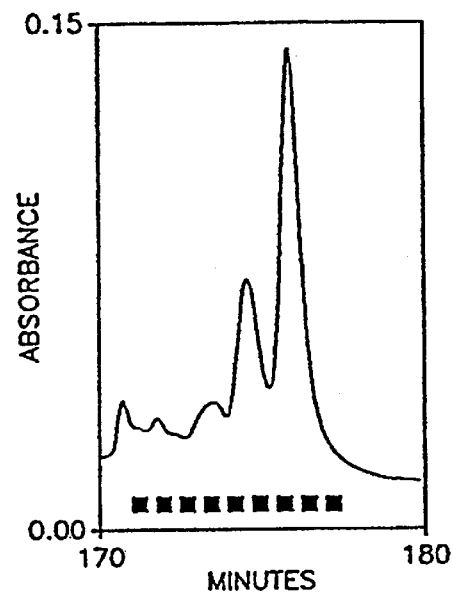

It is certified that error appears in the above-identified patent and that said Letters Patent is hereby corrected as shown below:

In column 5, line 28, please delete the phrase "Figure 1 shows", and insert therefor the phrase: --Figs. 1A-B show--.
In column 5, line 31, please delete the phrase "Figure 2 shows", and insert therefor the phrase: --Figs. 2A-E show--.
In column 5, line 34, please delete the phrase "Figure 3 shows", and insert therefor the phrase: --Figs. 3A-B show--.
In column 5, line 40, please delete the phrase "Figure 4 shows", and insert therefor the phrase: --Figs. 4A-B show--.
In column 5, line 41, please delete the phrase "Figure 3", and insert therefor the phrase: --Figs. 3A-B--.
In column 5, line 44, please delete the phrase "Figure 5 shows", and insert therefor the phrase: --Figs. 5A-B show--.
In column 5, lines 44-45, please delete the phrase "Figure 3", and insert therefor the phrase: --Figs. 3A-B--.
In column 5, line 52, please delete the phrase "Figure 7 shows", and insert therefor the phrase: --Figs. 7A-F show--.
In column 5, line 62, please delete the phrase "Figure 10 shows", and insert therefor the phrase: --Figs. 10A-B show--.
In column 6, line 3, please delete the phrase "Figure 13 shows", and insert therefor the phrase: --Figs. 13A-C show--.
In column 6, line 6, please delete the phrase "Figure 14 shows", and insert therefor the phrase: --Figs. 14A-D show--.

UNITED STATES PATENT AND TRADEMARK OFFICE
CERTIFICATE OF CORRECTION

PATENT NO. : 5,804,200
DATED : September 8, 1998
INVENTOR(S) : Grieve et al.

Figure 15A:
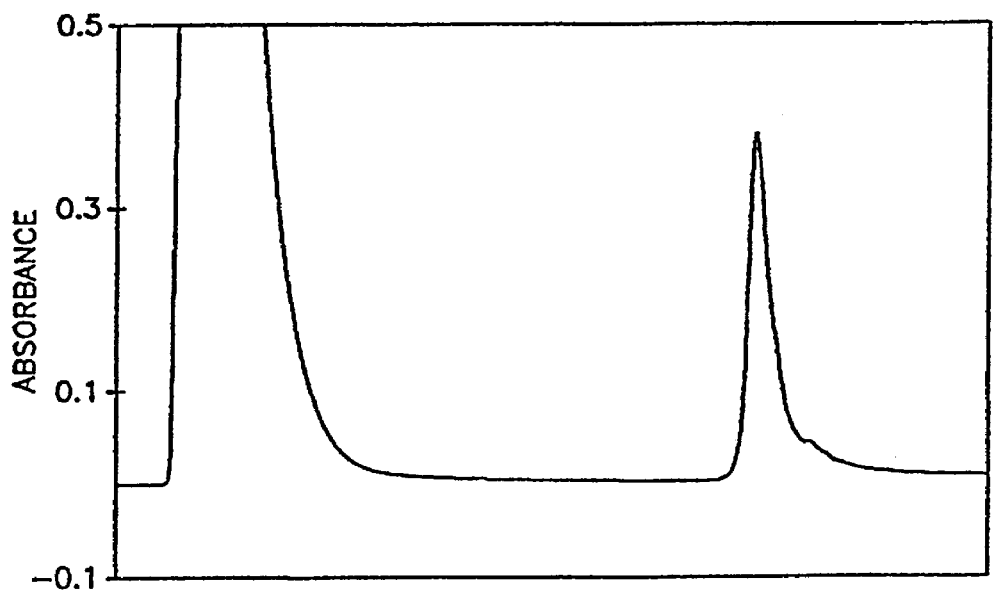
FIG. 15 shows the chromatograms of the second separation of larval ES by cation exchange chromatography.
Figure 15B:
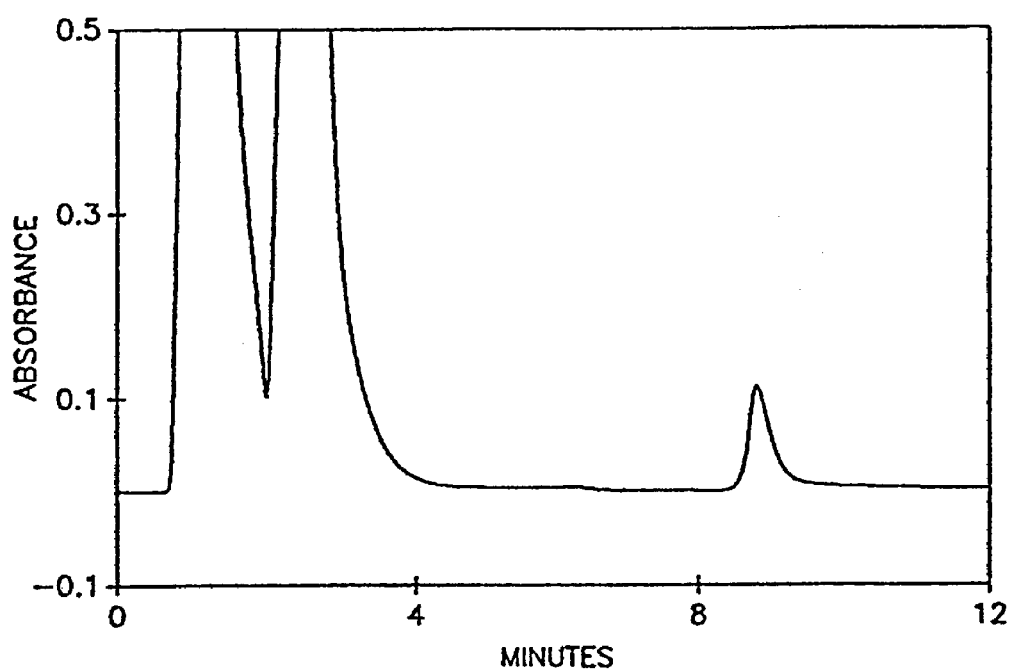
Figure 16A:
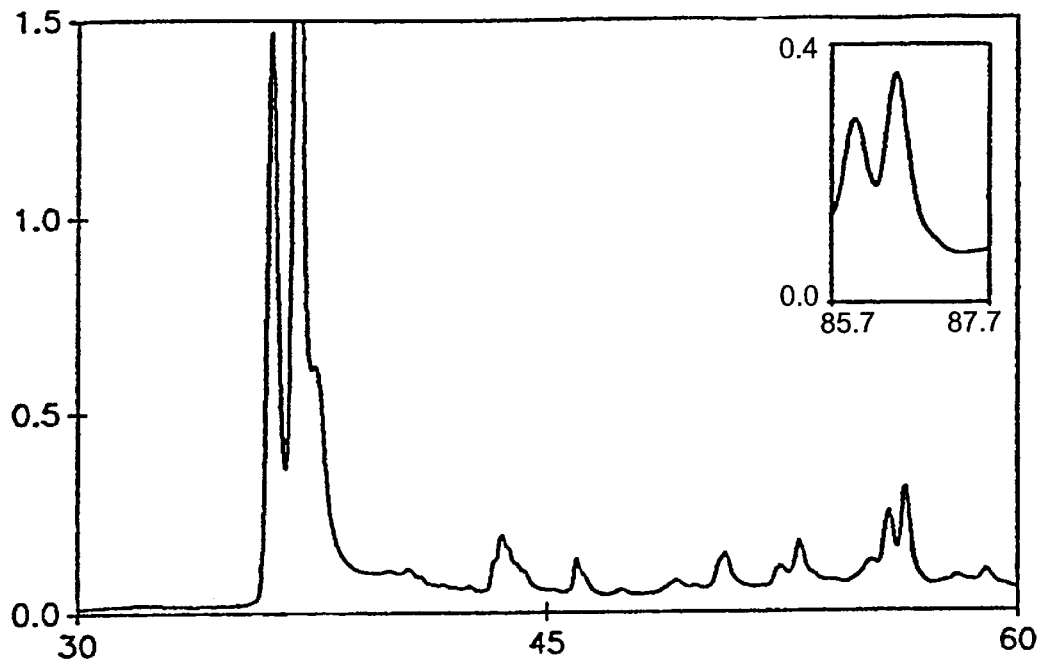
FIG. 16 shows the results for reverse phase chromatography of larval ES proteins after separation by cation exchange chromatography, as shown in FIG. 15.
Figure 16B:
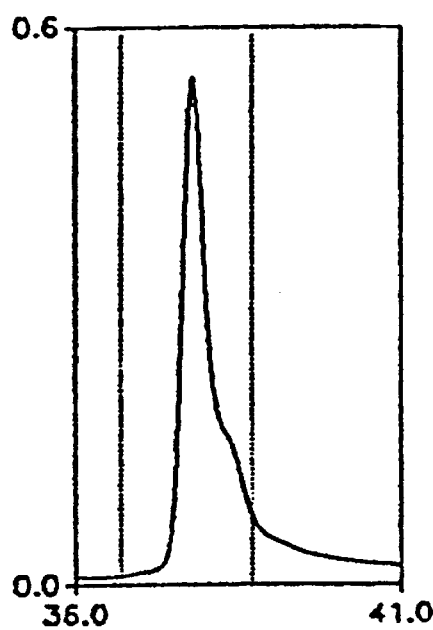
Figure 16C:
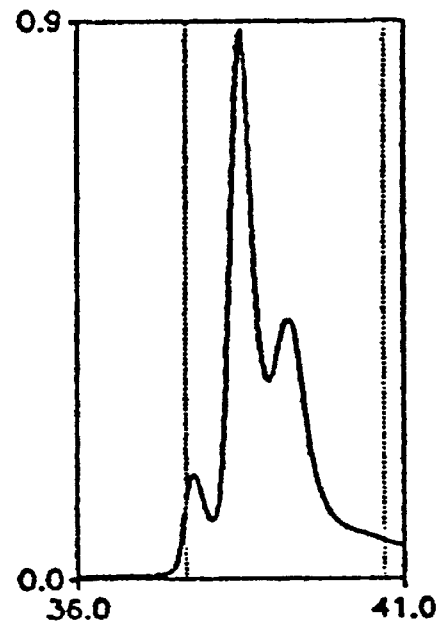
Figure 17A:
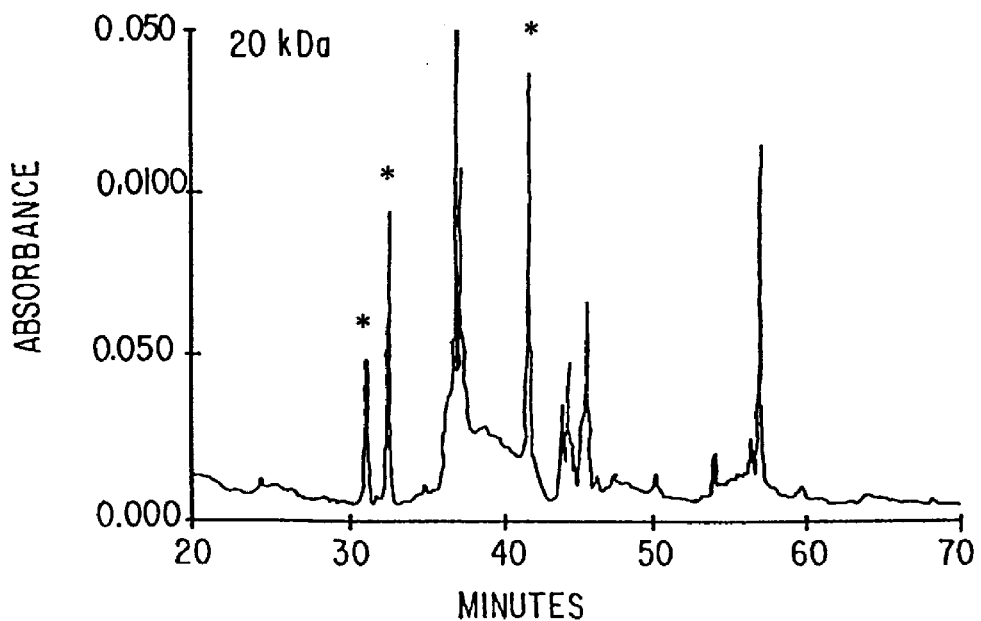
FIG. 17 shows the results of $C_{18}$ reverse phase chromatography of trypsin digests of the 20, 22L and 22U kD proteins purified by cation exchange and reverse phase chromatography as shown in FIGS. 15 and 16.
Figure 17B:
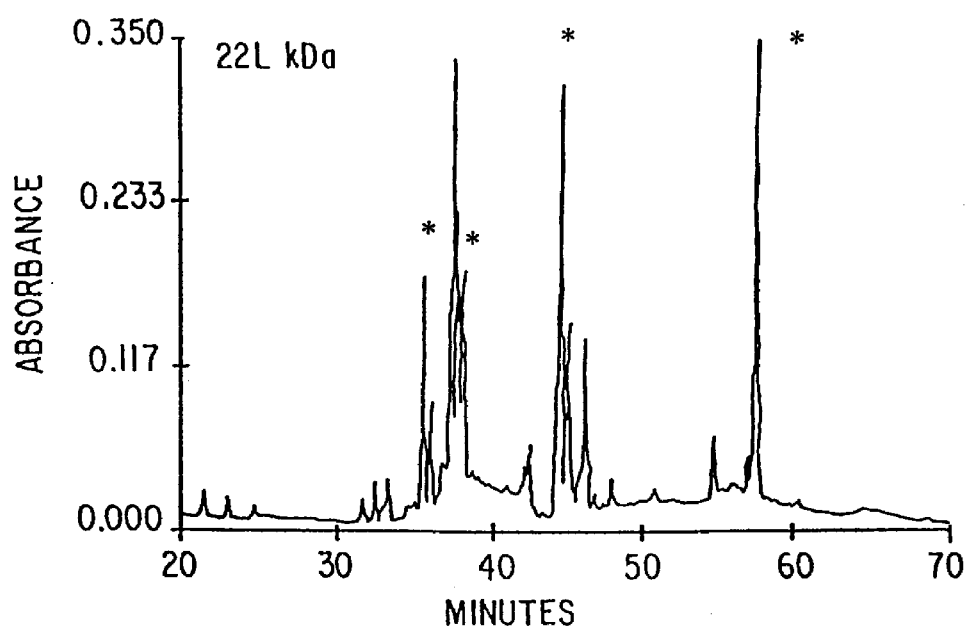
Figure 17C:
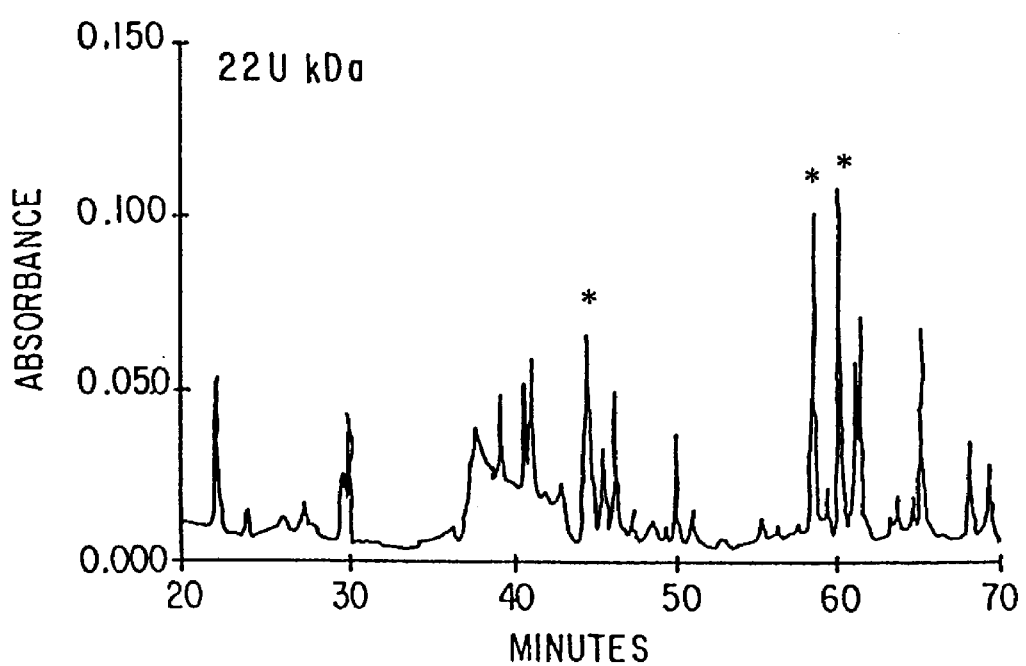
Figure 23A:
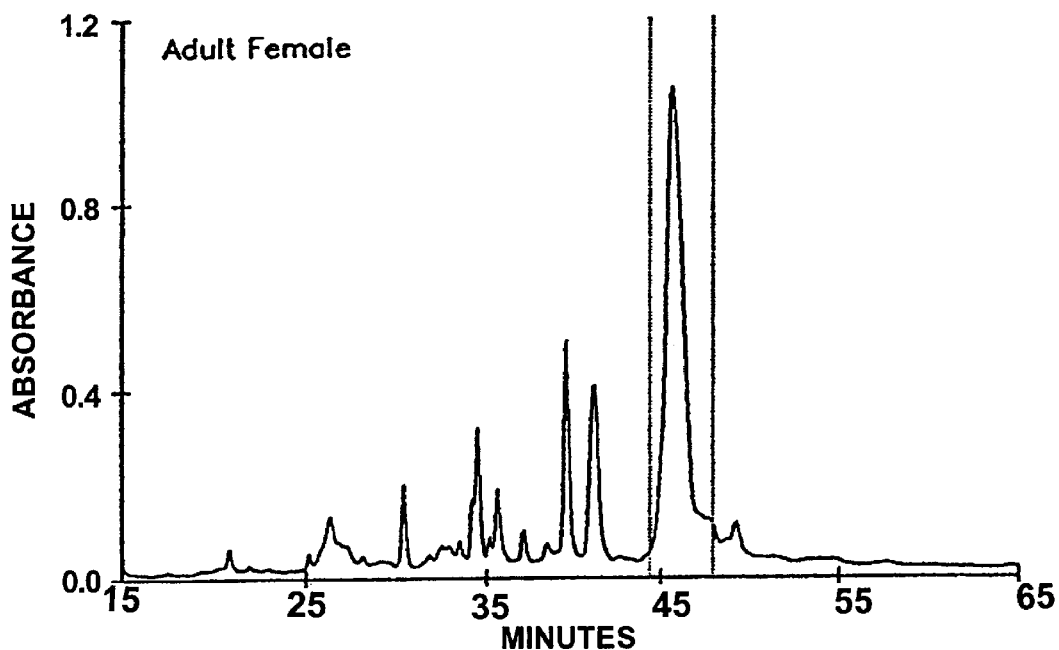
FIG. 23 shows chromatograms for $C_4$ reverse phase separations of proteins from adult male and female D. immitis.
Figure 23B:
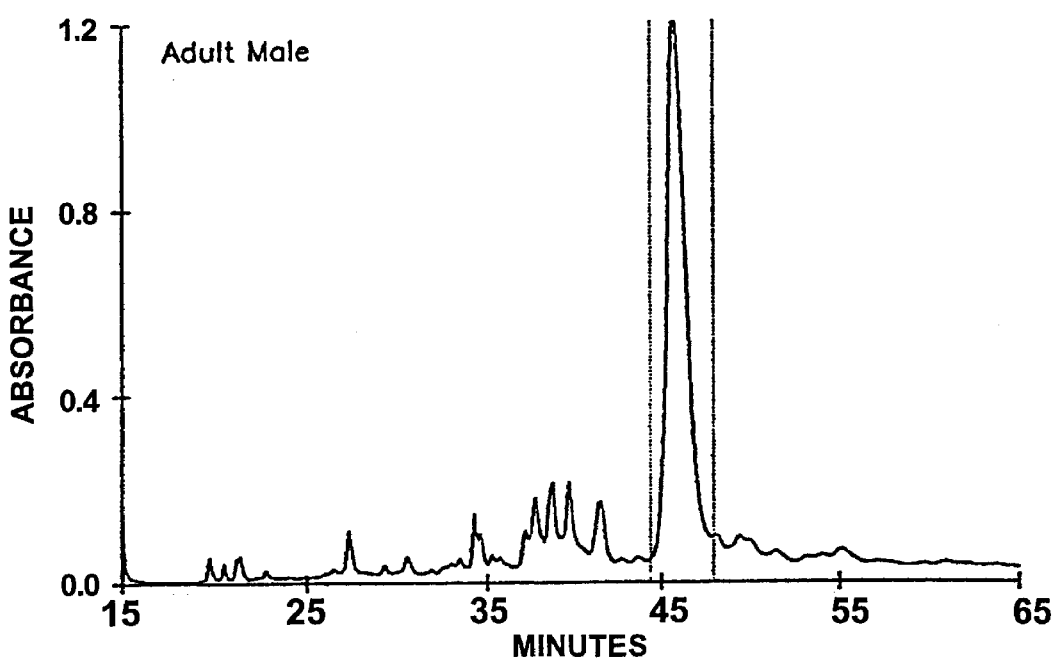

It is certified that error appears in the above-identified patent and that said Letters Patent is hereby corrected as shown below:

In column 6, line 7, please delete the phrase "Figure 13", and insert therefor the phrase: --Figs. 13A-B--.
In column 6, line 12, please delete the phrase "Figure 15 shows", and insert therefor the phrase: --Figs. 15A-B show--.
In column 6, line 14, please delete the phrase "Figure 16 shows", and insert therefor the phrase: --Figs. 16A-C show--.
In column 6, line 16, please delete the phrase "Figure 15", and insert therefor the phrase: --Figs. 15A-B--.
In column 6, line 17, please delete the phrase "Figure 17 shows", and insert therefor the phrase: --Figs. 17A-C show--.
In column 6, line 20, please delete the phrase "Figures 15 and 16", and insert therefor the phrase: --Figs. 15A-B, and Figs. 16A-B--.
In column 6, line 24, please delete the phrase "Figure 19 shows", and insert therefor the phrase: --Figs. 19A-D show--.
In column 6, line 27, please delete the phrase "Figure 20 shows", and insert therefor the phrase: --Figs. 20A-C show--.
In column 6, line 34, please delete the phrase "Figure 23 shows", and insert therefor the phrase: --Figs. 23A-B show--.

UNITED STATES PATENT AND TRADEMARK OFFICE
CERTIFICATE OF CORRECTION

PATENT NO. : 5,804,200
DATED : September 8, 1998
INVENTOR(S) : Grieve et al.

Figure 24A:
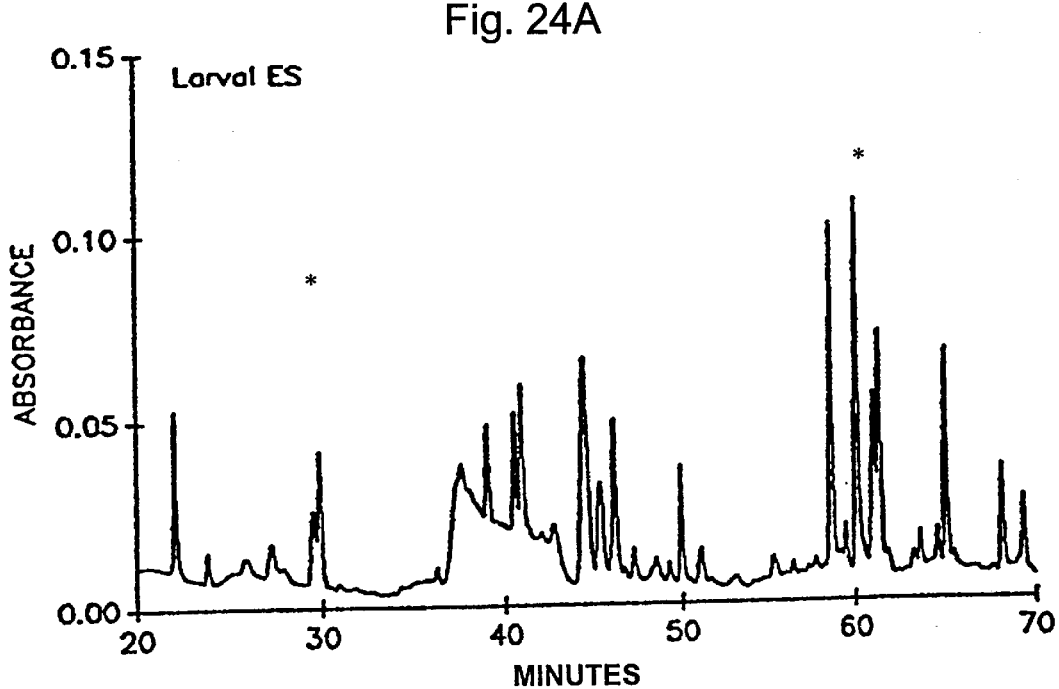
FIG. 24 shows trypsin digests of the 22U kD proteins of larval ES, adult females and adult males separated by $C_{18}$ reverse phase chromatography.
Figure 24B:
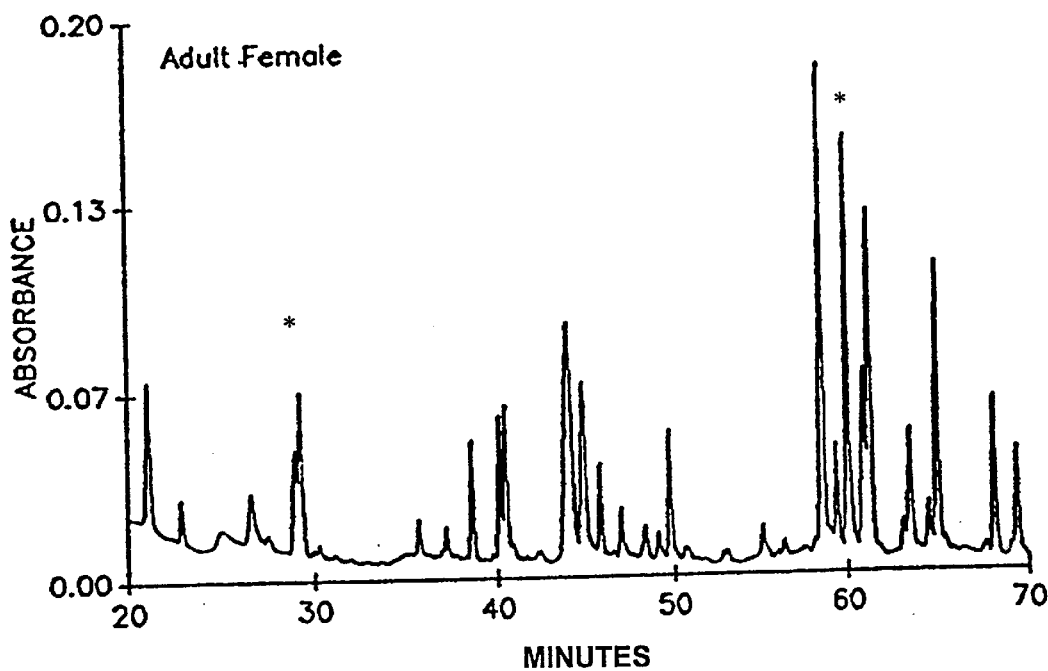
Figure 24C:
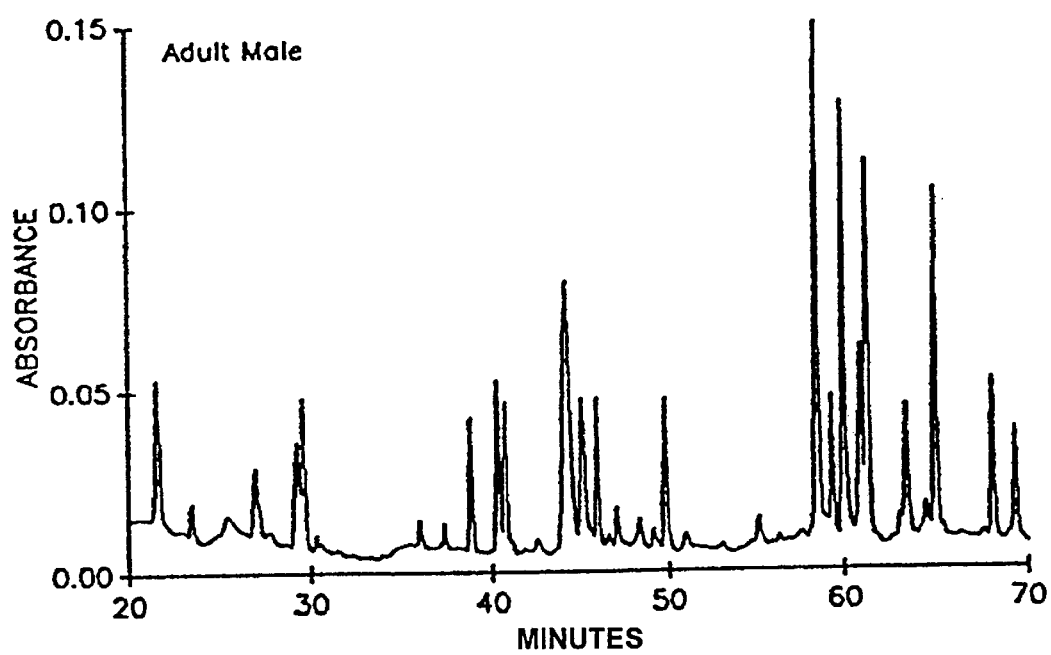

It is certified that error appears in the above-identified patent and that said Letters Patent is hereby corrected as shown below:

In column 6, line 37, please delete the phrase "Figure 24 shows", and insert therefor the phrase: --Figs. 24A-C show--.
In column 17, line 17, please delete the phrase "Figure 1", and insert therefor the phrase: --Figs. 1A-D--.
In column 17, lines 18, please delete the phrase "Figure 1", and insert therefor the phrase: --Figs. 1A-D--.
In column 17, line 29, please delete the phrase "Figure 2", and insert therefor the phrase: --Figs. 2A-E--.
In column 17, line 46, please delete the phrase "Figures 3, 4 and 5", and insert therefor the phrase: --Figs. 3A-B, 4A-B and 5A-B--.
In column 17, line 46, please delete the phrase "Figure 3", and insert therefor the phrase: --Figs. 3A-B--.
In column 17, line 55, please delete the phrase "Figure 4", and insert therefor the phrase: --Figs. 4A-B--.
In column 17, line 58, please delete the phrase "Figure 5 shows", and insert therefor the phrase: --Figs. 5A-B show--.
In column 17, line 66, please delete the phrase "Figure 3", and insert therefor the phrase: --Fig. 3A--.
In column 19, line 39, please delete the phrase "Figure 7 shows", and insert therefor the phrase: --Figs. 7A-F show--.
In column 19, line 46, please delete the phrase "Figure 8 shows", and insert therefor the phrase: --Figs. 8A-F show--.

UNITED STATES PATENT AND TRADEMARK OFFICE
CERTIFICATE OF CORRECTION

PATENT NO. : 5,804,200
DATED : September 8, 1998
INVENTOR(S) : Grieve et al.

It is certified that error appears in the above-identified patent and that said Letters Patent is hereby corrected as shown below:

In column 20, line 34, please delete the phrase "Figure 10", and insert therefor the phrase: --Figs. 10A-B--.

In column 20, line 38, please delete the phrase "group A in Figure 8", and insert therefor the phrase: --shown in Fig. 8A--.

In column 20, line 43, please delete the phrase "Figure 8", and insert therefor the phrase: --Figs. 8A-F--.

In column 21, line 52, please delete the phrase "Figure 13 is", and insert therefor the phrase: --Figs. 13A-C are--.

In column 21, line 60, please delete the phrase "A and C", and insert therefor the phrase: --Figs. 14A-C--.

In column 21, line 61, please delete the phrase "B and D", and insert therefor the phrase: --Figs. 14B-D--.

In column 21, line 65, please delete the phrase "Figure 14", and insert therefor the phrase: --Figs. 14A-D--.

In column 22, line 20, please delete the phrase "Figure 15 shows", and insert therefor the phrase: --Figs. 15A-B show--.

In column 22, line 24, please delete the phrase "the top chromatogram", and insert therefor the phrase: --Fig. 15A--.

In column 22, line 25-26, please delete the phrase "the bottom chromatogram", and insert therefor the phrase: --Fig. 15B--.

UNITED STATES PATENT AND TRADEMARK OFFICE
CERTIFICATE OF CORRECTION

PATENT NO. : 5,804,200
DATED : September 8, 1998
INVENTOR(S) : Grieve et al.

It is certified that error appears in the above-identified patent and that said Letters Patent is hereby corrected as shown below:

In column 22, line 43, please delete the phrase "Figure 16 shows", and insert therefor the phrase: --Figs. 16A-C show--.
In column 22, line 45, please delete the phrase "Figure 15", and insert therefor the phrase: --Figs. 15A-B--.
In column 22, line 47, please delete the phrase "the upper chromatogram", and insert therefor the phrase: --Fig. 16A--.
In column 22, line 51, please delete the phrase "the bottom two chromatograms", and insert therefor the phrase: --Figs. 16B-C--.
In column 23, line 31, please delete both occurrences of the phrase "Figure 17", and insert for each the phrase: --Figs. 17A-C--.
In column 23, at lines 61-65, please delete the paragraph beginning with "Figure 19" and ending with "22U kD protein.", and insert therefor the following paragraph:

--Figs. 19A-D show a Coomassie stained gel of 1 $\mu$l each of fractions A-D. Fig. 19A is comprised mostly of the 20 kD protein, Fig. 19B demonstrates both the 20 kD and 22L kD proteins and Fig. 19C shows an enrichment of the 22L kD protein. Fig. 19D is the 22U kD protein.--

UNITED STATES PATENT AND TRADEMARK OFFICE
CERTIFICATE OF CORRECTION

PATENT NO. : 5,804,200
DATED : September 8, 1998
INVENTOR(S) : Grieve et al.

Figure 27A:
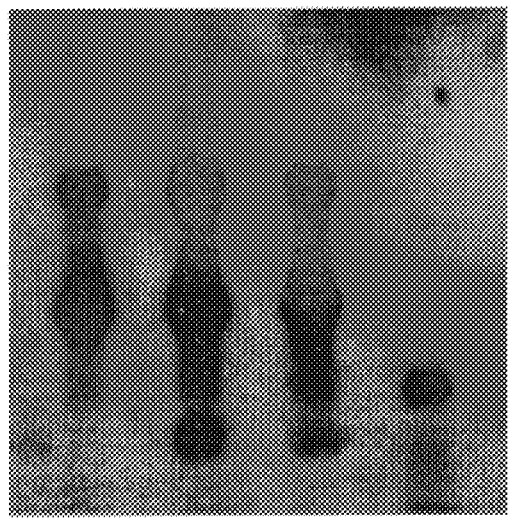
FIG. 27A–B shows Northern blot analysis of transcripts of the 20/22L kD protein.
Figure 27B:
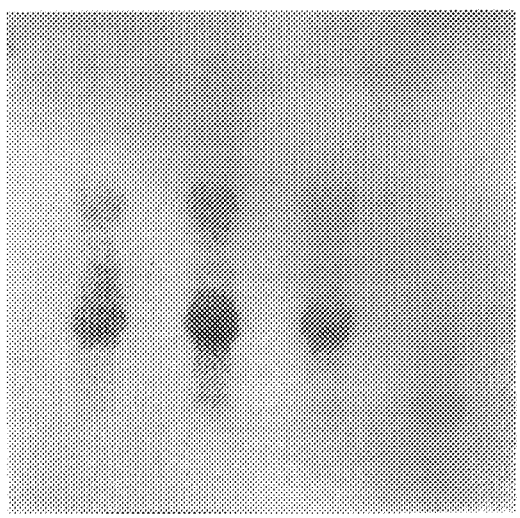

It is certified that error appears in the above-identified patent and that said Letters Patent is hereby corrected as shown below:

In column 24, line 18, please delete the phrase "Figure 20 shows", and insert therefor the phrase: --Figs. 20A-C show--.
In column 24, line 22, please delete the phrase "Figure 19", and insert therefor the phrase: --Figs. 19A-D--.
In column 24, line 64, please delete the phrase "Figure 17", and insert therefor the phrase: --Figs. 17A-C--.
In column 25, line 31, please delete the phrase "(lane B in Figure 19)", and insert therefor the phrase: --(Fig. 19B)--.
In column 25, line 52-53, please delete the phrase "(Figure 19, lane B)", and insert therefor the phrase: --(Fig. 19B)--.
In column 26, line 41, please delete the phrase "Figure 23 shows", and insert therefor the phrase: --Figs. 23A-B show--.
In column 27, line 12, please delete the phrase "Figure 24 shows", and insert therefor the phrase: --Figs. 24A-C show--.
In column 31, line 16, please delete the phrase "Figure 27 shows", and insert therefor the phrase: --Figs. 27A-B show--.
In column 31, line 21, please delete the phrase "(A)", and insert therefor the phrase: --(Fig. 27A)--.
In column 31, line 24, please delete the phrase "panel B", and insert therefor the phrase: --Fig. 27B--.

UNITED STATES PATENT AND TRADEMARK OFFICE
CERTIFICATE OF CORRECTION

PATENT NO. : 5,804,200
DATED : September 8, 1998
INVENTOR(S) : Grieve et al.

Figure 29A:
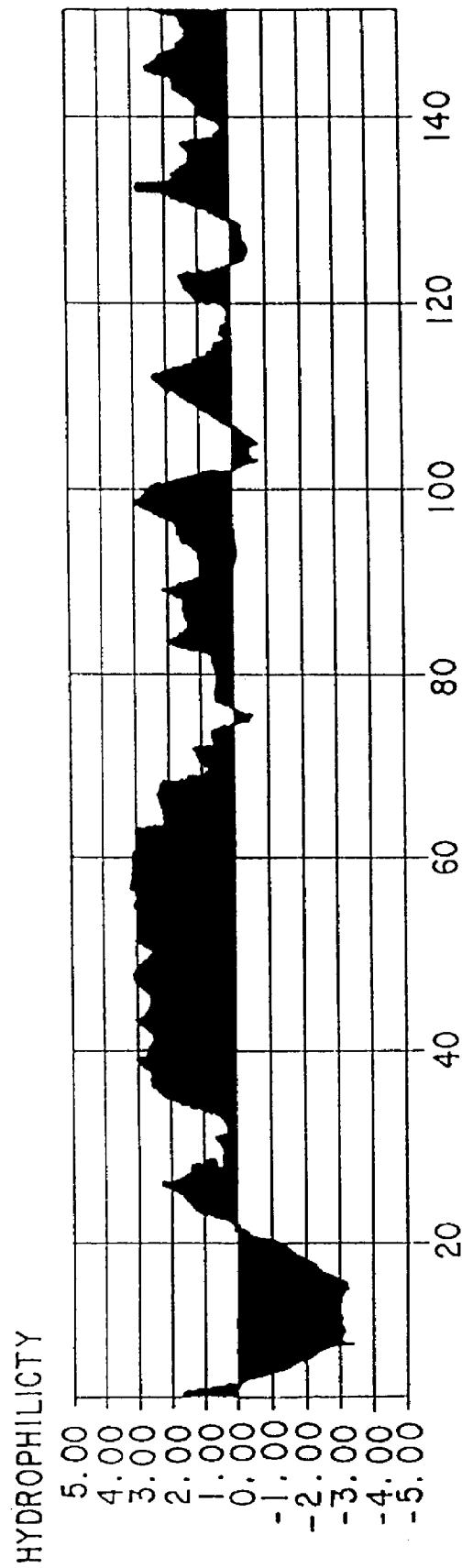

It is certified that error appears in the above-identified patent and that said Letters Patent is hereby corrected as shown below:

In column 32, line 1, please delete the phrase "Figure 29 shows", and insert therefor the phrase: --Fig. 29A shows--.
In column 32, line 2, please delete the phrase "(A)", and insert therefor the phrase: --(Fig. 27A)--.
In column 32, line 7, please delete the phrase "(B, 22L kD)", and insert therefor the phrase: --(Fig. 29B, 22L kD)--.
In column 32, line 8, please delete the phrase "(C, 20 kD)", and insert therefor the phrase: --(Fig. 29C, 20 kD)--.
In column 32, line 20, please delete the phrase "(Figure 29)", and insert therefor the phrase: --(Figs. 29B-C)--.
In column 32, line 25, please delete the phrase "Figure 29 ", and insert therefor the phrase: --Figs. 29B-C--.

Signed and Sealed this

Twenty-second Day of August, 2000

Attest:

Q. TODD DICKINSON

Attesting Officer          Director of Patents and Trademarks